(12) United States Patent
Fu

(10) Patent No.: US 7,151,109 B2
(45) Date of Patent: Dec. 19, 2006

(54) PYRAZOLO[1,5-A]PYRIDINE DERIVATIVES AND THEIR USE AS NEUROTRANSMITTER MODULATORS

(75) Inventor: Jian-Min Fu, Kalamazoo, MI (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 0 days.

(21) Appl. No.: 10/387,159

(22) Filed: Mar. 12, 2003

(65) Prior Publication Data

US 2004/0002511 A1 Jan. 1, 2004

Related U.S. Application Data

(60) Provisional application No. 60/363,766, filed on Mar. 13, 2002, provisional application No. 60/380,576, filed on May 14, 2002, provisional application No. 60/403,547, filed on Aug. 14, 2002.

(51) Int. Cl.
*A61K 31/44* (2006.01)
(52) U.S. Cl. ........................ 514/300; 546/121
(58) Field of Classification Search ................ 546/121; 514/300
See application file for complete search history.

(56) References Cited

U.S. PATENT DOCUMENTS

| 5,525,480 A * | 6/1996 | Zimmermann et al. ........ 435/18 |
| 6,043,260 A | 3/2000 | Chen et al. .................. 514/348 |
| 6,589,947 B1 | 7/2003 | Hamanaka et al. ......... 514/348 |

FOREIGN PATENT DOCUMENTS

| EP | 0433855 A2 | 12/1990 |
| EP | 433855 * | 6/1991 |
| FR | 2822689 A1 | 3/2001 |
| FR | 2822690 A1 | 3/2001 |
| FR | 2822691 | 3/2001 |
| FR | 2822692 A1 | 3/2001 |
| JP | 61097285 | 5/1986 |
| JP | 11265079 | 9/1999 |
| JP | 11265080 | 9/1999 |
| WO | WO 99/01454 | 1/1999 |
| WO | WO 00/39127 | 7/2000 |
| WO | WO 00/59907 | 10/2000 |
| WO | WO 00/59908 | 10/2000 |
| WO | WO 01/35917 * | 5/2001 |
| WO | WO 01/35917 A1 | 5/2001 |
| WO | WO 01/87889 A1 | 11/2001 |
| WO | WO 02/088121 | 1/2002 |
| WO | WO 02/076416 A1 | 10/2002 |

OTHER PUBLICATIONS

Molina et al. Synthetic Comunications 1987, 17(16): 1929-37.*
Hori et al. Heterocycles 1986, 24(9): 2563-70.*
Molina et al. Synthesis 1983, 12: 1021-2.*
Arques et al. Synthesis 1981, 11: 910-12.*
Gewald et al. Journal fuer Praktische Chmie (Liepzig) 1975, 317(4): 561-6.*
Duerr et al. Justus Liebigs Annalen der Chemie 1974, 7: 1140-9.*
Duerr et al. Chemische Berichte 1974, 107(6): 2027-36.*
Luber et al. Bioorganic & Medicinal Chemistry Letters 2002 12(4): 633-636.*
He et al. J. Med. Chem. 2000, 43:449-456.*
Chorvat et al. J Med. Chem. 2000, 42: 833-848.*
Kehne,J et al, Non-peptidic CRF1 receptor antagonists for the treatment of anxiety, depression and stress disorders, PMID: 12769601.*
Reul, JMHM et al, Corticotropin-releasing factor receptors 1 and 2 in anxiety and depression, Neurosciences, Current Opin. Pharmacology, 2002, 2:23-33.*
Abarca B. et al., Chemical Abstracts, 1991, 115:23.
Arato M. et al., Biol. Psychiatry, 1989, 25:355.
Arques A. et al., Chemical Abstracts, 1982, 96:5.
Banki C.M. et al., Am. J. Psychiatry, 1987, 144:873.
Berridge, C. W. and A.J. Dunn, Regul. Peptides, 1986, 16:83.
Berridge, C. W. and A. J. Dunn, Horm. Behav., 1987, 21:393.
Berridg, C.W. and A. J. Dunn, Brain Research Reviews, 1990, 15:71.
Blalock, Physiological Reviews, 1989, 69:1.
Britton D. R. et al., Life Sci., 1982, 31:363.
Britton, K. T. , et al., Psychopharmacology, 1985, 86:170.
Britton, K. T. , Psychopharmacology, 1988, 94:306.
De Souza, E.B., Hosp. Practice, 1988, 23:59.
De Souza, E. B. et al., J. Neurosci., 1985, 5:3189.
Duerr H. et al., Chemical Abstracts, 1974, 81:23, p. 522.
Duerr H. et al., Chemical Abstracts, 1974, 81:11, p. 465.
Duerr H. et al., Chemical Abstracts, 1974, 81:11, p. 391.
Duerr H. et al., Chemical Abstracts, 1972, 77:21.
Elghandour A.H.H. et al., Chemical Abstracts, 1989, 110:21.
France et al., Biol. Psychiatry, 1988, 28:86.
Gewald K. et al., Chemical Abstracts, 1975, 83:23.

(Continued)

*Primary Examiner*—Amelia A. Owens
(74) *Attorney, Agent, or Firm*—Austin Zhang; Robert Young; Charles W. Ashbrook

(57) ABSTRACT

The present invention relates to novel pyrazolo[1,5-a]pyridine derivatives of general formula I:

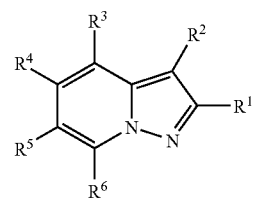

Formula I that bind with high affinity to $CRF_1$ receptors, including human $CRF_1$ receptors. This invention also relates to methods of using the compounds of the invention to treat a disorder or condition, the treatment of which can be effected or facilitated by antagonizing a CRF receptor, such as CNS disorders or diseases, particularly anxiety disorders, and depression and stress related disorders.

10 Claims, No Drawings

OTHER PUBLICATIONS

Gold, P. W. et al., Am. J. Psychiatry, 1984, 141:619.
Gold, P. W. et al., New Engl. J. Med., 1986, 314:1129.
Grigoriadis, et al., Neuropsychopharmacology, 1989, 2:53.
Holsboer F. et al., Psychoneuroendocrinology, 1984, 9:147.
Hori M. et al., Chemical Abstracts, 1987, 106:25.
Köckritz P. et al., J. Heterocyclic Chem., 1994, 31, 1157.
Koob G. F. et al., CRC Press, 1990, p. 221.
Koob G. F., Persp. Behav. Med., 1985, 2:39.
Löber S. et al., Bioorganic & Medicinal Chem. Letters, 2002, p. 633-636.
Molina P. et al., Chemical Abstracts, 1984, 100:15.
Molina P. et al., J. Heterocyclic Chem., 1984, 21, 685.
Morley, J.E. et al., Life Sci., 1987, 41:527.
Nemeroff, et al., Science, 1984, 226:1342.
Nemeroff C.B., et al., Arch. Gen Psychiatry, 1988, 45:577.
Rivier J. et al., Proc. Natl. Acad. Sci (USA), 1983, 80:4851.
Sapolsky, R. M., Arch. Gen. Psychiatry, 1989, 46:1047 (Abstract only).
Swerdlow N. R. et al., Psychopharmacology, 1986, 88:147.
Tamura Y. et al., J. Heterocyclic Chem., 1973, 10, pp. 447-450.
Vale W. et al, Science, 1981, 213:1394.
Vale W. et al, Rec. Prog. Horm. Res., 1983, 39:245.

* cited by examiner

PYRAZOLO[1,5-A]PYRIDINE DERIVATIVES AND THEIR USE AS NEUROTRANSMITTER MODULATORS

CROSS-REFERENCE TO OTHER APPLICATIONS

This application claims the benefit of U.S. Provisional Application Ser. No. 60/363,766 filed on Mar. 13, 2002, U.S. Provisional Application Ser. No. 60/380,576 filed on May 14, 2002, and U.S. Provisional Application Ser. No. 60/403,547 filed on Aug. 14, 2002.

FIELD OF THE INVENTION

The present invention relates generally to compounds that bind to CRF receptors and particularly to pyrazolo[1,5-a]pyridine derivatives useful as $CRF_1$ receptor antagonists, and to the use thereof as a treatment for disorders that are associated with CRF or $CRF_1$ receptors.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response in the immune system to physiological, psychological, and immunological stressors [J. E. Blalock, *Physiological Reviews* 69:1 (1989); J. E. Morley, *Life Sci.* 41:527 (1987)].

There is evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for a review, see: E. B. De Souze, *Hosp. Practice* 23:59 (1988)].

Anxiety disorders are a group of diseases, recognized in the art, that includes phobic disorders, anxiety states, posttraumatic stress disorder and atypical anxiety disorders [The Merck Manual of Diagnosis and Therapy, 16$^{th}$ edition (1992)]. Emotional stress is often a precipitating factor in anxiety disorders, and such disorders generally respond to medications that lower response to stress.

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders, and is known to produce anxiogenic effects in animals. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn, *Regul. Peptides* 16:83 (1986)]. Preliminary studies using the putative CRF receptor antagonist α-helical ovine CRF (9-41) in a variety of behavioral paradigms demonstrates that the antagonist produces "anxiolytic-like" effects that are qualitatively similar to the benzodiazepines [C. W. Berridge and A. J. Dunn, *Horm. Behav.* 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist Ro 15-1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)]. The mechanisms and sites of action through which conventional anxiolytics and antidepressants produce their therapeutic effects remain to be elucidated. Preliminary studies, examining the effects of a $CRF_1$ receptor antagonist peptide (α-helical $CRF_{9-41}$) in a variety of behavioral paradigms, have demonstrated that the $CRF_1$ antagonist produces "anxiolytic-like" effects qualitatively similar to the benzodiazepines [for a review, see: G. F. Koob and K. T. Britton, In: *Corticotrbpin-Releasing Factor: Basic and Clinical Studies of a Neuropeptide*, E. B. De Souza and C. B. Nemeroff eds., CRC Press p. 221 (1990)].

The use of CRF, antagonists for the treatment of Syndrome X has also been described in U.S. patent application Ser. No. 09/696,822, filed Oct. 26, 2000, and European Patent Application No. 003094414, filed Oct. 26, 2000, which are also incorporated in their entireties herein by reference. Methods for using $CRF_1$ antagonists to treat congestive heart failure are described in U.S. Ser. No. 09/248,073, filed Feb. 10, 1999, now U.S. Pat. No. 6,043,260 (Mar. 28, 2000) which is also incorporated herein in its entirety by reference.

CRF is known to have a broad extrahypothalmic distribution in the CNS, contributing therein to a wide spectrum of autonomic behavioral and physiological effects [see, e.g., Vale et al., 1983; Koob, 1985; and E. B. De Souze et al., 1985]. For example, CRF concentrations are significantly increased in the cerebral spinal fluid of patients afflicted with affective disorder or major depression [see, e.g., Nemeroff et al., 1984; Banki et al., 1987; France et al., 1988; Arato et al., 1989]. Moreover, excessive levels of CRF are known to produce anxiogenic effects in animal models [see, e.g., Britton et al., 1982; Berridge and Dunn, 1986 and 1987], and $CRF_1$ antagonists are known to produce anxiolytic effects; accordingly, therapeutically effective amounts of compounds provided herein are, for example, determined by assessing the anxiolytic effects of varying amounts of the compounds in such animal models.

WO 99/01454, WO 00/39127, WO 00/59907, WO 00/59908 and WO 02/088121 disclose various compounds that can bind with high affinity and high selectivity to $CRF_1$ receptors. The compounds are useful for treating CNS-related disorders particularly affective disorders and diseases, and acute and chronic neurological disorders and diseases.

It is an object of the invention to provide novel pyrazolo [1,5-a]pyridine derivatives, which are $CRF_1$ receptor antagonists.

It is another object of the invention to provide novel compounds as treatment of disorders or conditions that are associated with CRF or $CRF_1$ receptors, such as anxiety disorders, depression, and stress related disorders.

It is another object of the invention to provide a method of treating disorders or conditions that are associated with CRF or $CRF_1$ receptors, such as anxiety disorders, depression, and stress related disorders.

It is yet another object of the invention to provide a pharmaceutical composition useful for treating disorders or conditions that are associated with CRF or $CRF_1$ receptors, such as anxiety disorders, depression, and stress related disorders.

There are other objects of the invention which will be evident or apparent from the description of the invention in the specification of the application.

SUMMARY OF THE INVENTION

In one aspect, the present invention provides a compound of general formula I:

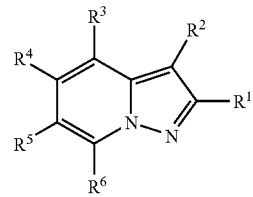

Formula I a stereoisomer thereof, a pharmaceutically acceptable salt thereof, a derivative thereof, or a prodrug thereof, wherein:

$R^1$ is selected from —H, —$NR^7R^8$, —$OR^7$, —$S(O)_mR^7$, —$C(O)R^7$, —$C(S)R^7$, —$C(O)OR^7$, —$C(S)OR^7$, —$C(O)NR^7R^8$, —$C(S)NR^7R^8$, alkyl, substituted alkyl, cycloalkyl, substituted cycloalkyl, heterocycloalkyl, and substituted heterocycloalkyl;

$R^2$ is selected from —$NR^7R^8$, —$OR^7$, —$S(O)_mR^7$, —$C(O)R^7$, —$C(S)R^7$, —$C(O)OR^7$, —$C(S)OR^7$, $C(O)NR^7R^8$, —$C(S)NR^7R^8$, alkyl, substituted alkyl, cycloalkyl, substituted cycloalkyl, heterocycloalkyl, substituted heterocycloalkyl, Ar, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, —NHC(O)alkyl, —NHC(S)alkyl, —NHC(O)aryl, —NHC(S)aryl, —NHC(O)$OR^7$, —NHC(O)$SR^7$, —NHC(S)$OR^7$, —NHC(O)$NR^7R^8$, —NHC(S)$NR^7R^8$, —NHS(O)$_n$alkyl, —NHS(O)$_n$aryl, —NHS(O)$_n$ $NR^7R^8$,

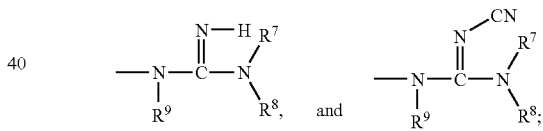

$R^3$, $R^4$ and $R^5$ can be the same or different and are independently selected from —H, alkyl, substituted alkyl, cycloalkyl, substituted cycloalkyl, heterocycloalkyl, substituted heterocycloalkyl, Ar, halogen, —$NR^9R^{10}$, —$OR^9$, —$S(O)_mR^9$, —$C(O)R^9$, —$C(S)R^9$, —$C(O)OR^9$, —$C(S)OR^9$, —$C(O)NR^9R^{10}$, and —$C(S)NR^9R^{10}$;

$R^6$ is selected from Ar, —OAr, —$S(O)_mAr$, —N(H)Ar, and —$NR^{11}R^{12}$;

$R^7$ and $R^8$ (1) can be the same or different and are independently selected from —H, alkyl, substituted alkyl, cycloalkyl, substituted cycloalkyl, Ar, or (2) when both $R^7$ and $R^8$ are alkyls and attached to a nitrogen, may form, along with the nitrogen, a 3–8 membered mono heterocyclic ring, which may be optionally substituted with 1 to 3 substituents selected from halogen, —$R^9$, —$OR^9$, —$S(O)_mR^9$, —$NR^9R^{10}$, —$C(O)R^9$, —$C(S)R^9$, —CN, —$C(O)NR^9R^{10}$, —$C(S)NR^9R^{10}$, —$NR^9C(O)R^{10}$, —$NR^9C(S)R^{10}$, —$S(O)_n NR^9R^{10}$, —$NR^9S(O)_nR^{10}$, —$NO_2$, —$C(O)OR^9$ and —$C(S)OR^9$, or (3) when $R^7$ and $R^8$ are attached to a nitrogen and $R^7$ is alkyl and $R^8$ is either cycloalkyl or Ar, form a 7–12 membered bicyclic heterocyclic ring, which may be optionally substituted with 1 to 3 substituents selected from halogen, —R$^9$, —OR$^9$, —S(O)$_m$R$^9$, —NR$^9$R$^{10}$, —C(O)R$^9$, —C(S)R$^9$, —CN, —C(O)NR$^9$R$^{10}$, —C(S)NR$^9$R$^{10}$, —NR$^9$C(O)R$^{10}$, —NR$^9$C(S)R$^{10}$, —S(O)—NR$^9$R$^{10}$, —NR$^9$S(O)$_n$R$^{10}$, —NO$_2$, —C(O)OR$^9$ and —C(S)OR$^9$;

R$^9$ and R$^{10}$ can be the same or different and are independently selected from—H, alkyl, substituted alkyl, cycloalkyl, substituted cycloalkyl, and Ar;

R$^{11}$ and R$^{12}$ (1) can be the same or different and are independently selected from H, alkyl, substituted alkyl, cycloalkyl, substituted cycloalkyl, heterocycloalkyl, substituted heterocycloalkyl, Ar, or (2) can form a 5- or 6-membered monocylic or a 8–10-membered bicyclic heteroaryl ring system, which may optionally contain, in addition to the nitrogen, an additional heteroatom selected from N, S, and O, and which may optionally have an oxo substituent on the ring and also may be optionally substituted with 1 to 3 substituents selected from halogen, —R$^9$, —OR$^9$, —S(O)$_m$R$^9$, —NR$^9$R$^{10}$, —C(O)R$^9$, —C(S)R$^9$, —CN, —C(O)NR$^9$R$^{10}$, —C(S)NR$^9$R$^{10}$, —NR$^9$C(O)R$^{10}$, —NR$^9$C(S)R$^{10}$, —S(O)$_n$NR$^9$R$^{10}$, —NR$^9$S(O)$_n$R$^{10}$, —NO$_2$, —C(O)OR$^9$ and —C(S)OR$^9$;

m is 0, 1 or 2; and
n is 1 or 2.

In another aspect, the present invention provides a pharmaceutical composition comprising a compound of Formula I, a stereoisomer thereof, a pharmaceutically acceptable salt thereof, or a prodrug thereof, or a pharmaceutically acceptable salt of the prodrug thereof. The compositions can be prepared in any suitable forms such as tablets, pills, powders, lozenges, sachets, cachets, elixirs, suspensions, emulsions, solutions, syrups, aerosols, and ointments.

The compounds of the inventions are CRF$_1$ receptor antagonists and are useful for treating disorders or conditions associated with CRF or CRF$_1$ receptors, including human CRF1 receptors.

Thus, in another aspect, the present invention provides a method of antagonizing CRF$_1$ receptors in a warm-blooded animal, comprising administering to the animal a compound of the invention at amount effective to antagonize CRF$_1$ receptors.

In still another aspect, the present invention provides a method for screening for ligands for CRF$_1$ receptors, which method comprises: a) carrying out a competitive binding assay with CRF$_1$ receptors, a compound of formula I which is labelled with a detectable label, and a candidate ligand; and b) determining the ability of said candidate ligand to displace said labelled compound.

In still another aspect, the present invention provides a method for detecting CRF receptors in a tissue comprising: a) contacting a compound of formula I, which is labelled with a detectable label, with a tissue, under conditions that permit binding of the compound to the tissue; and b) detecting the labelled compound bound to the tissue.

In yet another aspect, the present invention provides a method of inhibiting the binding of CRF to CRF$_1$ receptors, comprising contacting a compound of the invention with a solution comprising cells expressing the CRF$_1$ receptor, wherein the compound is present in the solution at a concentration sufficient to inhibit the binding of CRF to the CRF$_1$ receptor.

In yet a further aspect the present invention provides a method of treating a disorder, in warm-blooded animal, the treatment of which disorder can be effected or faciliated by antagonizing CRF$_1$ receptors, which method comprises administration to a patient in need thereof an effective amount of a compound of formula (I). In a particular embodiment the invention provides a method for the treatment of disorders that manifests hypersecretion of CRF. Examples of disorders that can be treated with the compounds of the invention include generalized anxiety disorder; social anxiety disorder; anxiety; obsessive-compulsive disorder; anxiety with co-morbid depressive illness; panic disorder; and mood disorders such as depression, including major depression, single episode depression, recurrent depression, child abuse induced depression, and postpartum depression. It is preferred that the warm-blooded animal is a mammal, and more preferred that the animal is a human.

In addition, a method of inhibiting the binding of CRF to the CRF$_1$ receptor, which method comprises contacting, in the presence of CRF, a solution comprising a compound of formula I with cells expressing the CRF$_1$ receptor, wherein the compound is present in the solution at a concentration sufficient to reduce levels of CRF binding to IMR$^{32}$ cells in vitro is provided.

DETAILED DESCRIPTION OF THE INVENTION

In the first aspect, the present invention provides a compound of general formula I:

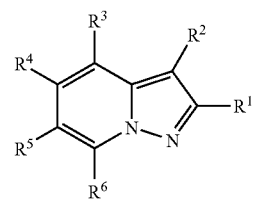

Formula I a stereoisomer thereof, a pharmaceutically acceptable salt thereof, a derivative thereof, or a prodrug thereof, wherein:

R$^1$ is selected from —H, —NR$^7$R$^8$, —OR$^7$, —S(O)$_m$R$^7$, —C(O)R$^7$, —C(S)R$^7$, —C(O)OR$^7$, —C(S)OR$^7$, —C(O)NR$^7$R$^8$, —C(S)NR$^7$R$^8$, alkyl, substituted alkyl, cycloalkyl, substituted cycloalkyl, heterocycloalkyl, and substituted heterocycloalkyl;

R$^2$ is selected from —NR$^7$R$^8$, —OR$^7$, —S(O),R$^7$, —C(O)R$^7$, —C(S)R$^7$, —C(O)OR$^7$, —C(S)OR$^7$, —C(O)NR$^7$R$^8$—C(S)C(S)NR$^7$R$^8$, alkyl, substituted alkyl, cycloalkyl, substituted cycloalkyl, heterocycloalkyl, substituted heterocycloalkyl, Ar, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, —NHC(O)alkyl, —NHC(S)alkyl, —NHC(O)aryl, —NHC(S)aryl, —NHC(O)OR$^7$, —NHC(O)SR$^7$, —NHC(S)OR$^7$, —NHC(O)NR$^7$R$^8$, —NHC(S)NR$^7$R$^8$, —NHS(O)$_n$alkyl, —NHS(O)$_n$aryl, —NHS(O)$_n$ NR$^7$R$^8$,

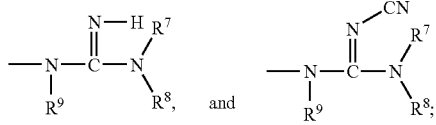

R³, R⁴ and R⁵ can be the same or different and are independently selected from —H, alkyl, substituted alkyl, cycloalkyl, substituted cycloalkyl, heterocycloalkyl, substituted heterocycloalkyl, Ar, halogen, —NR⁹R¹⁰, —OR⁹, —S(O)$_m$R⁹, —C(O)R⁹, —C(S)R⁹, —C(O)OR⁹, —C(S)OR⁹, —C(O)NR⁹R¹⁰, and —C(S)NR⁹R¹⁰;

R⁶ is selected from Ar, —OAr, —S(O)$_m$Ar, —N(H)Ar, and —NR¹¹R¹²;

R⁷ and R⁸ (1) can be the same or different and are independently selected from —H, alkyl, substituted alkyl, cycloalkyl, substituted cycloalkyl, Ar, or (2) when both R⁷ and R⁸ are alkyls and attached to a nitrogen, may form, along with the nitrogen, a 3–8 membered mono heterocyclic ring, which may be optionally substituted with 1 to 3 substituents selected from halogen, —R⁹, —OR⁹, —S(O)$_m$R⁹, —NR⁹R¹⁰, —C(O)R⁹, —C(S)R⁹, —CN, —C(O)NR⁹R¹⁰, —C(S)NR⁹R¹⁰, —NR⁹C(O)R¹⁰, —NR⁹C(S)R¹⁰, —S(O)$_n$NR⁹R¹⁰, —NR⁹S(O)$_n$R¹⁰, —NO₂, C(O)OR⁹ and —C(S)OR⁹, or (3) when R⁷ and R⁸ are attached to a nitrogen and R⁷ is alkyl and R⁸ is either cycloalkyl or Ar, form a 7–12 membered bicyclic heterocyclic ring, which may be optionally substituted with 1 to 3 substituents selected from halogen, —R⁹, OR⁹, —SR⁹, —NR⁹R¹⁰, —C(O)R⁹, —C(S)R⁹, —CN, —C(O)NR⁹R¹⁰, —C(S)NR⁹R¹⁰, —NR⁹C(O)R¹⁰, —NR⁹C(S)R¹⁰, —S(O)$_n$NR⁹R¹⁰, —NR⁹S(O)$_n$R¹⁰, —NO₂, —C(O)OR⁹ and —C(S)OR⁹;

R⁹ and R¹⁰ can be the same or different and are independently selected from —H, alkyl, substituted alkyl, cycloalkyl, substituted cycloalkyl, and Ar;

R¹¹ and R¹² (1) can be the same or different and are independently selected from H, alkyl, substituted alkyl, cycloalkyl, substituted cycloalkyl, heterocycloalkyl, substituted heterocycloalkyl, Ar, or (2) can form a 5- or 6-membered monocylic or a 8–10-membered bicyclic heteroaryl ring system, which may optionally contain, in addition to the nitrogen, an additional heteroatom selected from N, S, and O, and which may optionally have an oxo substituent on the ring and also may be optionally substituted with 1 to 3 substituents selected from halogen, —R⁹, —OR⁹, —S(O)$_m$R⁹, —NR⁹R¹⁰, —C(O)R⁹, —C(S)R⁹, —CN, —C(O)NR⁹R¹⁰, —C(S)NR⁹R¹⁰, —NR⁹C(O)R¹⁰, —NR⁹C(S)R¹⁰, —S(O)$_n$NR⁹R¹⁰, —NR⁹S(O)$_n$R¹⁰, —NO₂, —C(O)OR⁹ and —C(S)OR⁹; illustrative examples of the heteroaromatic ring systems that can be formed from R¹¹ and R¹² together with the nitrogen to which they are attached being:

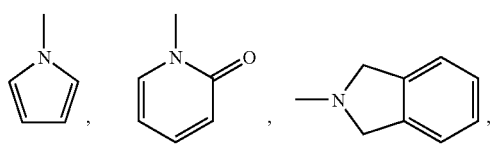

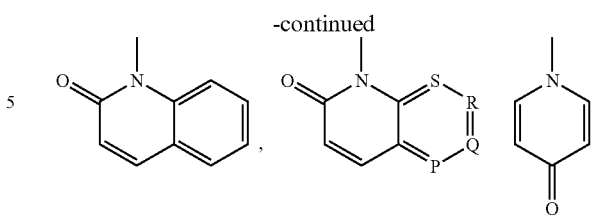

-continued where one of P, Q, R, S is N and the others represent C.

m is 0, 1 or 2; and n is 1 or 2.

Preferably, the present invention provide a compound of formula I above, or a stereoisomer thereof, a pharmaceutically acceptable salt thereof, a derivative thereof, or a prodrug thereof, wherein in formula I:

R¹ is selected from alkyl, substituted alkyl, cycloalkyl, substituted cycloalkyl, —NR⁷R⁸, —OR⁷, and —S(O)$_m$R⁷;

R² is selected from alkyl, substituted alkyl, cycloalkyl, substituted cycloalkyl, heterocycloalkyl, substituted heterocycloalkyl, Ar, —NHC(O)alkyl, —NHC(S)alkyl, —NHC(O)aryl, —NHC(S)aryl, —NHC(O)OR⁷, —NHC(O)SR⁷, —NHC(S)OR⁷, —NHC(O)NR⁷R⁸, —NHC(S)NR⁷R⁸, —NHS(O)$_n$alkyl, —NHS(O)$_n$aryl, —NHS(O)$_n$NR⁷R⁸,

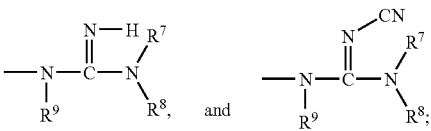

R³, R⁴, and R⁵ can be the same or different and are independently selected from —H, alkyl, substituted alkyl, halogen, and Ar; and R⁶ is selected from Ar, —OAr, and —NR¹¹R¹².

More preferably, the present invention provide a compound of formula I, a stereoisomer thereof, a pharmaceutically acceptable salt thereof, a derivative thereof, or a prodrug thereof, wherein in formula I, R¹ is selected from alkyl, substituted alkyl, —NR⁷R⁸, —OR⁷, and —S(O)$_m$R⁷;

R² is selected from alkyl, substituted alkyl, cycloalkyl, substituted cycloalkyl, heterocycloalkyl, substituted heterocycloalkyl, and Ar;

R³, R⁴, and R⁵ can be the same or different and are independently selected from —H, alkyl, substituted alkyl, and halogen; and R⁶ is selected from Ar and —NR¹¹R¹².

Further preferably, the present invention provide a compound of formula I, a stereoisomer thereof, a pharmaceutically acceptable salt thereof, a derivative thereof, or a prodrug thereof, wherein in formula I, R¹ is selected from alkyl and substituted alkyl;

R² is selected from alkyl, substituted alkyl, cycloalkyl, substituted cycloalkyl, heterocycloalkyl, substituted heterocycloalkyl, and Ar;

R³, R⁴, and R⁵ each is selected from —H, alkyl, and substituted alkyl; and

R⁶ is selected from Ar and —NR¹¹R¹².

Following are examples of particular compounds of the invention, with each compound being identified both by a chemical name and a structural formula immediately below the chemical name:

7-(2,4-Dichlorophenyl)-N,N-diethylpyrazolo[1,5-a]pyridin-3-amine

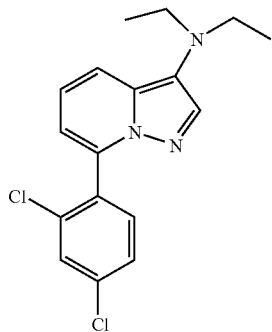

7-(2,4-Dichlorophenyl)-N,N-dipropylpyrazolo[1,5-a]pyridin-3-amine

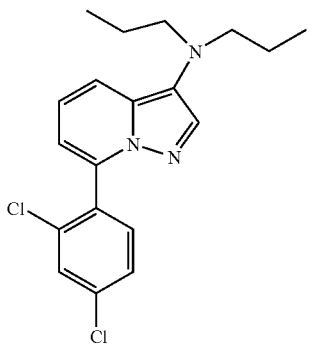

N-(Cyclopropylmethyl)-N-ethyl-7-(2,4-dichlorophenyl)pyrazolo[1,5-a]pyridin-3-amine

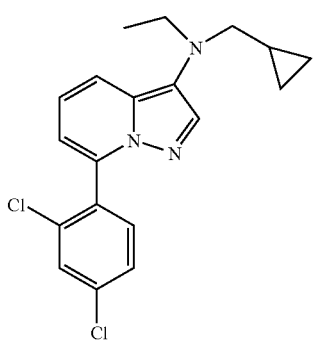

7-(2,4-Dichlorophenyl)-N,N-diethyl-2-methylpyrazolo[1,5-a]pyridin-3-amine

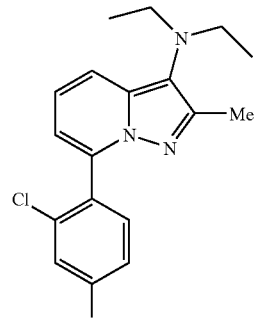

7-(2,4-Dichlorophenyl)-2-methyl-N,N-dipropylpyrazolo[1,5-a]pyridin-3-amine

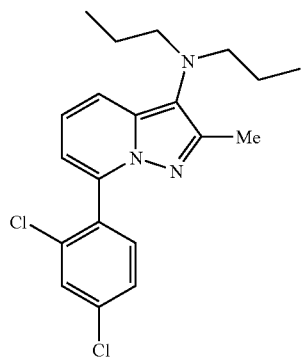

7-(2,4-Dichlorophenyl)-N,N,2-triethylpyrazolo[1,5-a]pyridin-3-amine

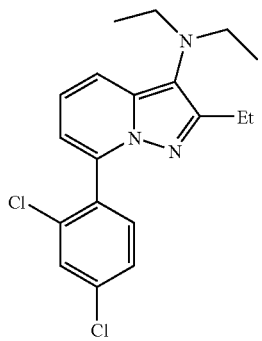

7-(2-Methyl-4-chlorophenyl)-N,N,2-triethylpyrazolo[1,5-a]pyridin-3-amine

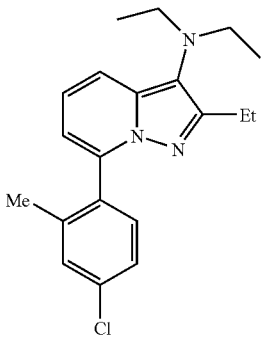

7-(2-Chloro-4-trifluoromethylphenyl)-N,N,2-triethylpyrazolo[1,5-a]pyridin-3-amine

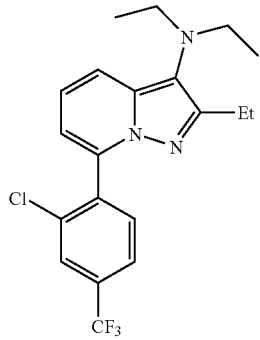

7-(2,4,6-Trimethylphenyl)-N,N,2-triethylpyrazolo[1,5-a]pyridin-3-amine

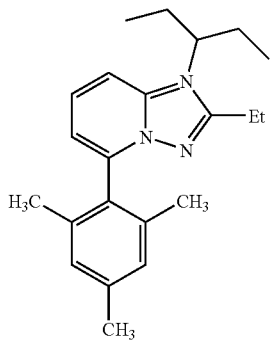

7-(2,4-Dichlorophenyl)-2-ethyl-N,N-dipropylpyrazolo[1,5-a]pyridin-3-amine

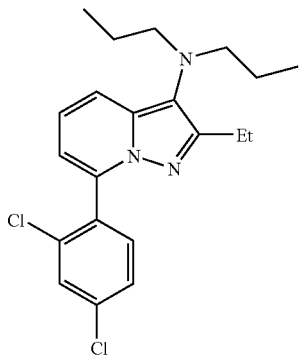

7-(2,4-Dichlorophenyl)-2-ethyl-N,N-dipropylpyrazolo[1,5-a]pyridin-3-amine maleic acid salt

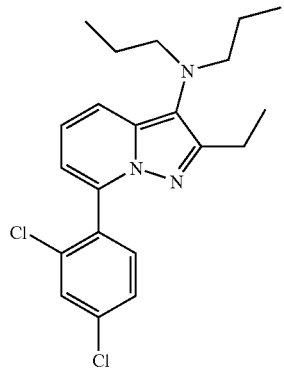

2-Ethyl-7-(4-methoxy-2-methylphenyl)-N,N-dipropylpyrazolo[1,5-a]pyridin-3-amine

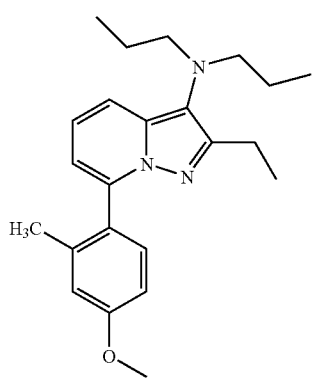

7-(2-Chloro-4-methoxyphenyl)-2-ethyl-N,N-dipropylpyrazolo[1,5-a]pyridin-3-amine

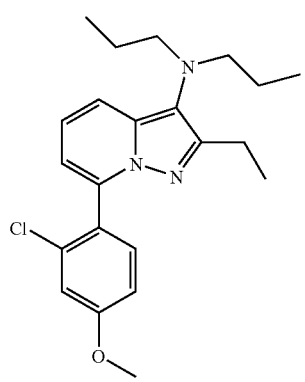

7-[4-(Dimethylamino)-2-(trifluoromethyl)phenyl]-2-ethyl-N,N-dipropylpyrazolo[1,5-a]pyridin-3-amine

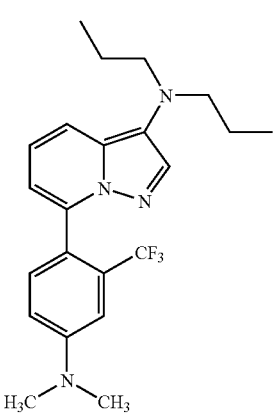

13

2-Ethyl-7-(2-methoxy-4,6-dimethylphenyl)-N,N-dipropylpyrazolo[1,5-a]pyridin-3-amine

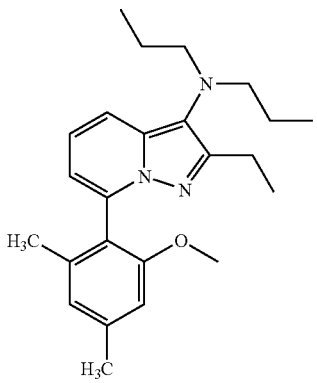

7-[2-Chloro-4-(dimethylamino)phenyl]-2-ethyl-N,N-dipropylpyrazolo[1,5-a]pyridin-3-amine

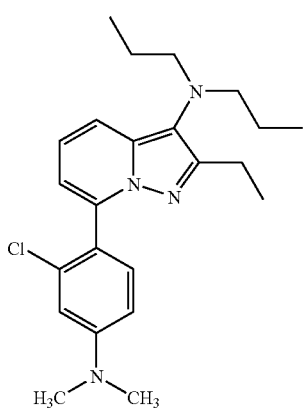

7-(2,4-Dimethoxyphenyl)-2-ethyl-N,N-dipropylpyrazolo[1,5-a]pyridin-3-amine

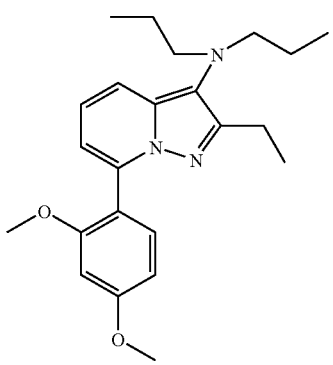

14

7-[6-(Dimethylamino)-4-methylpyridin-3-yl]-2-ethyl-N,N-dipropylpyrazolo[1,5-a]pyridin-3-amine

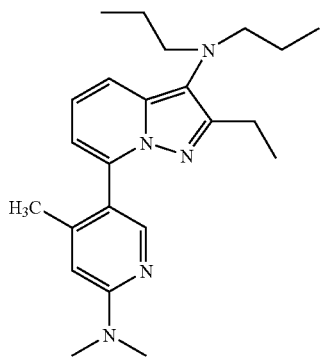

7-(2-Chloro-4-methoxyphenyl)-2-ethyl-N-(3-fluoropropyl)-N-(2-methoxyethyl)pyrazolo[1,5-a]pyridin-3-amine

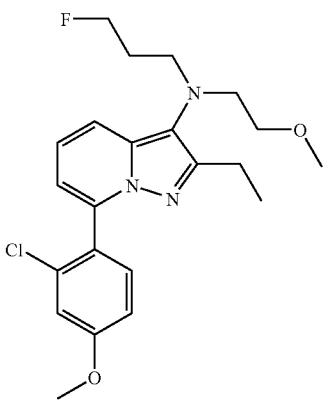

7-(2,4-Dimethoxyphenyl)-2-ethyl-N-(3-fluoropropyl)-N-(2-methoxyethyl)pyrazolo[1,5-a]pyridin-3-amine

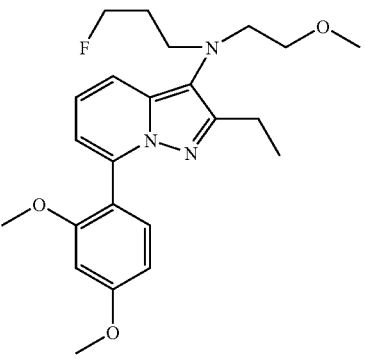

15

7-(2-Chloro-4-methoxyphenyl)-N,2-diethyl-N-(3-fluoropropyl)pyrazolo[1,5-a]pyridin-3-amine

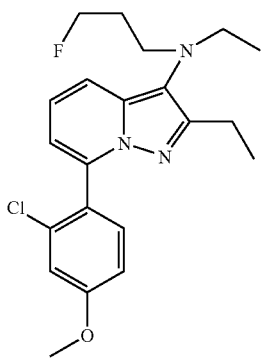

7-(2,4-Dimethoxyphenyl)-N,2-diethyl-N-(3-fluoropropyl)pyrazolo[1,5-a]pyridin-3-amine

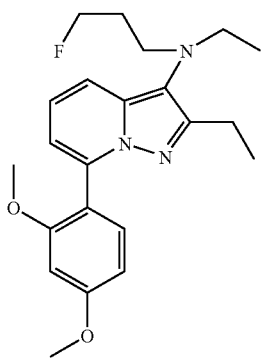

7-(2-Chloro-4-methoxyphenyl)-2-ethyl-N-(3-fluoropropyl)-N-methylpyrazolo[1,5-a]pyridin-3-amine

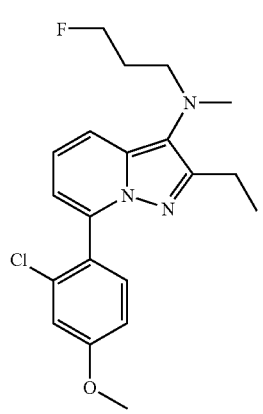

16

7-(2,4-Dimethoxyphenyl)-N,2-diethyl-N-(2-fluoroethyl)pyrazolo[1,5-a]pyridin-3-amine

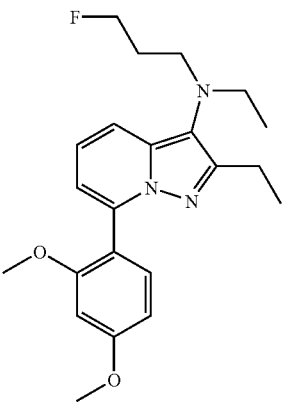

7-(2-Chloro-4-methoxyphenyl)-2-ethyl-N-(2-fluoroethyl)-N-(2-methoxyethyl)pyrazolo[1,5-a]pyridin-3-amine

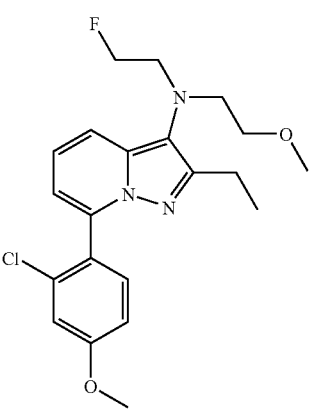

7-(2,4-Dimethoxyphenyl)-2-ethyl-N-(2-fluoroethyl)-N-(2-methoxyethyl)pyrazolo[1,5-a]pyridin-3-amine

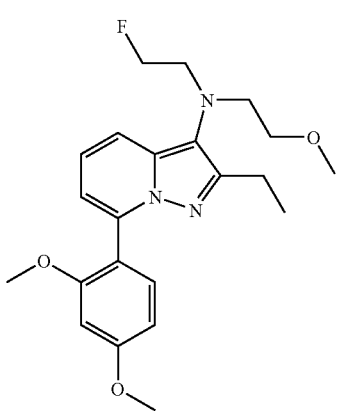

17

N-(Cyclopropylmethyl)-7-(2,4-dichlorophenyl)-N,2-diethylpyrazolo[1,5-a]pyridin-3-amine

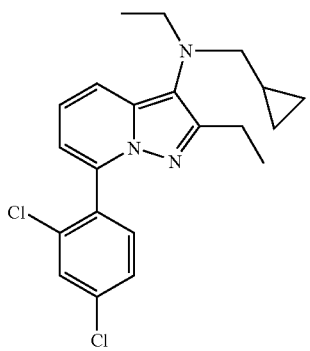

7-(2-Chloro-4-methoxyphenyl)-N-(cyclopropylmethyl)-N,2-diethylpyrazolo[1,5-a]pyridin-3-amine

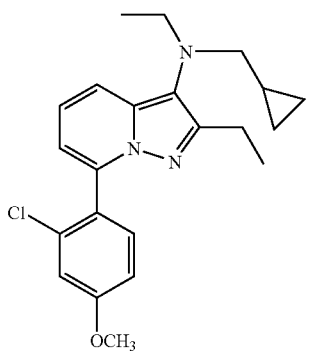

N-(Cyclopropylmethyl)-7-(2,4-dichlorophenyl)-2-ethyl-N-propopylpyrazolo[1,5-a]pyridin-3-amine

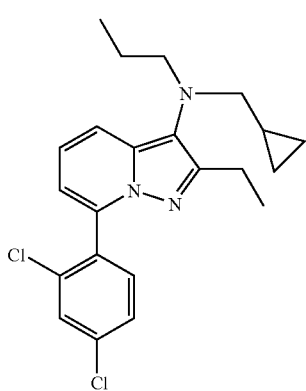

18

7-(2-Chloro-4-methoxyphenyl)-N-(cyclopropylmethyl)-2-ethyl-N-propylpyrazolo[1,5-a]pyridin-3-amine

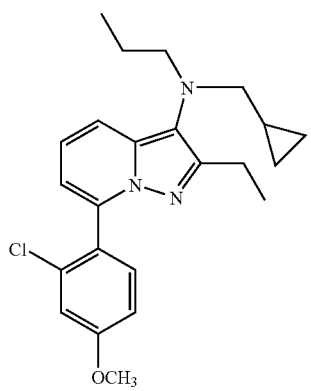

7-(2,4-Dichlorophenyl)-N-(1-ethylpropyl)-2-methylpyrazolo[1,5-a]pyridin-3-amine

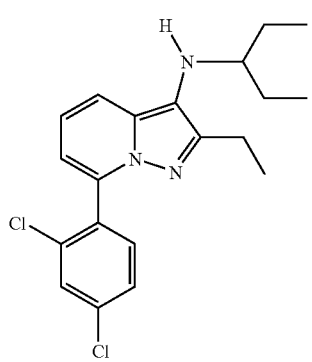

7-(2,4-Dichlorophenyl)-N-[2-methoxy-1-(methoxymethyl)ethyl]-2-methylpyrazolo[1,5-a]pyridin-3-amine

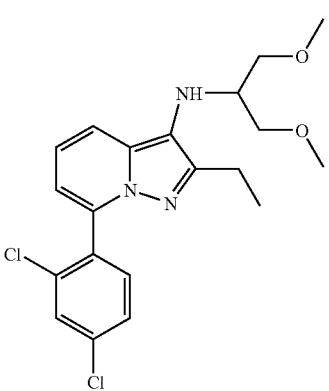

7-(2,4-Dichlorophenyl)-2-ethyl-N-(1-ethylpropyl)pyrazolo[1,5-a]pyridin-3-amine

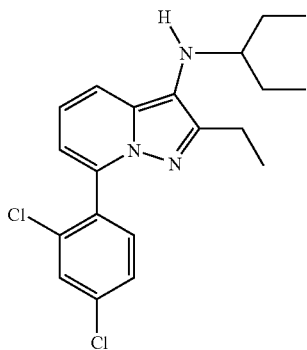

7-(2,4-Dichlorophenyl)-2-ethyl-N-[2-methoxy-1-(methoxymethyl)ethyl]pyrazolo[1,5-a]pyridin-3-amine

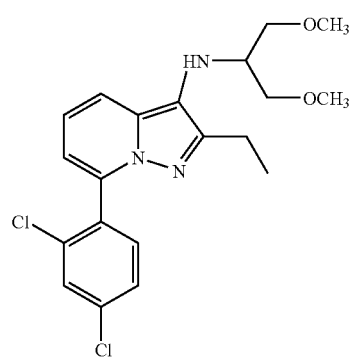

N-(sec-Butyl)-7-(2-chloro-4-methoxyphenyl)-2,6-dimethylpyrazolo[1,5-a]pyridin-3-amine

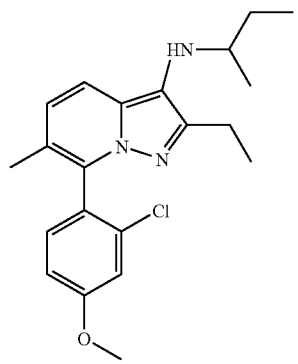

7-(2,4-Dichlorophenyl)-N-(-ethylpropyl)-2,6-dimethylpyrazolo[1,5-a]pyridin-3-amine

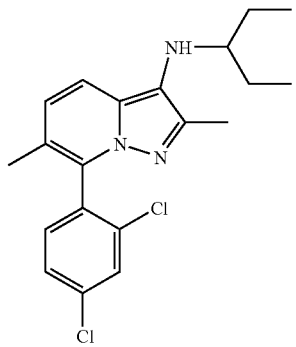

7-{[4-(Benzyloxy)pyridin-2-yl]oxy}-N,N-diethylpyrazolo[1,5-a]pyridin-3-amine

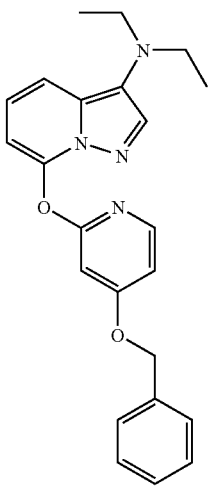

N,N-Diethyl-2-methyl-7-[(4-methylpyridin-2-yl)oxy]pyrazolo[1,5-a]pyridin-3-amine

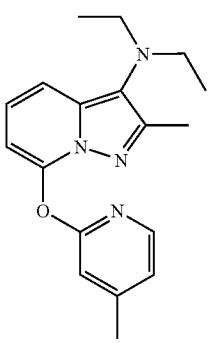

21

3-sec-Butyl-7-(2,4-dichlorophenyl)-2-ethylpyrazolo[1,5-a]pyridine

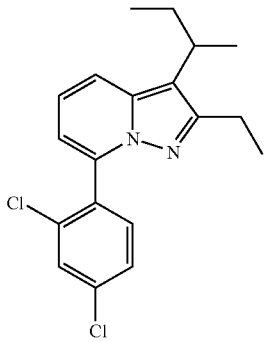

7-(2-Chloro-4-methoxyphenyl)-3-isopropyl-2-methylpyrazolo[1,5-a]pyridine

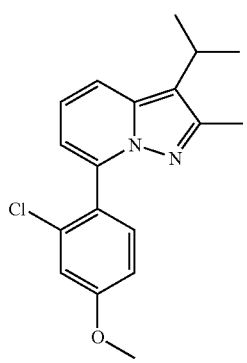

1-[7-(2,4-Dichlorophenyl)-2-methylpyrazolo[1,5-a]pyridin-3-yl]-1,2,3,6-tetrahydropyridine-4-carboxamide

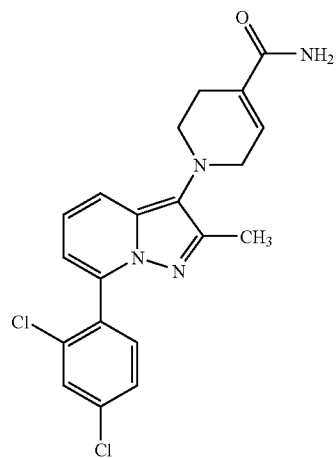

22

1-[7-(2-Chloro-4-methoxyphenyl)-2-methylpyrazolo[1,5-a]pyridin-3-yl]-1,2,3,6-tetrahydropyridine-4-carboxamide

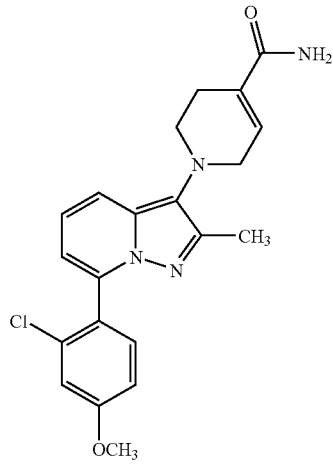

1-[7-(6-Methoxy-2-methylpyridin-3-yl)-2-methylpyrazolo[1,5-a]pyridin-3-yl]-1,2,3,6-tetrahydropyridine-4-carboxamide

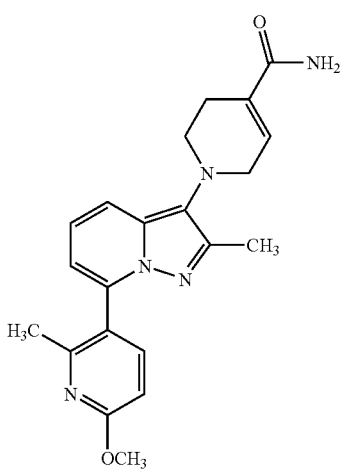

1-[7-(2,4-Dichlorophenyl)-2-ethylpyrazolo[1,5-a]pyridin-3-yl]-1,2,3,6-tetrahydropyridine-4-carboxamide

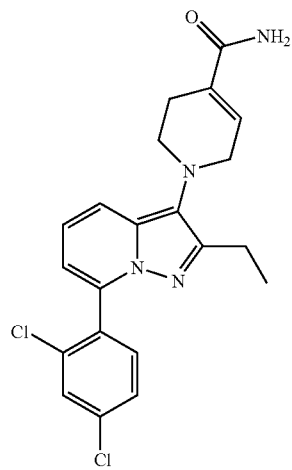

1-[7-(2-Chloro-4-methoxyphenyl)-2-ethylpyrazolo[1,5-a]pyridin-3-yl]-1,2,3,6-tetrahydropyridine-4-carboxamide

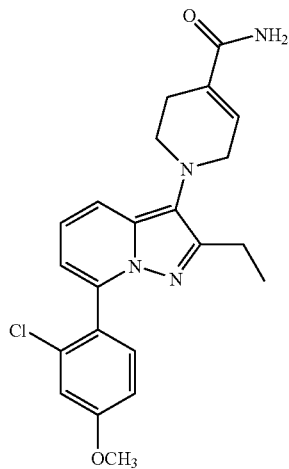

1-[7-(6-Methoxy-2-methylpyridin-3-yl)-2-ethylpyrazolo[1,5-a]pyridin-3-yl]-1,2,3,6-tetrahydropyridine-4-carboxamide

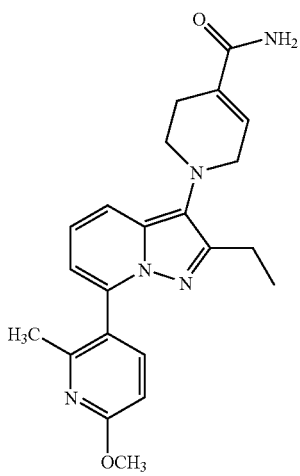

It should be understood that compounds provided herein can have one or more asymmetric centers or planes, and all chiral (enantiomeric and diastereomeric) and racemic forms of the compound are included in the present invention. Many geometric isomers of olefins, C=N double bonds, and the like can also be present in the compounds, and all such stable isomers are contemplated in the present invention.

Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by an asymmetric synthesis route enabling the preparation of enantiomerically enriched material. The present invention encompasses all possible tautomers of the compounds of formula (I).

Compounds of the invention can generally be prepared using the synthetic routes illustrated in the Charts A–H indicated below. Starting materials can be prepared by procedures described in these charts or by procedures that would be well known to one of ordinary skill in organic chemistry. The variables used in the charts are as defined below or as in the claims.

Preparation of compound of formula I, where $R^2=NR^7R^8$, is depicted in Chart A. The starting material A-1 is either available from a commercial source or can be prepared by adopting the known method described in the literature (see Tamura, Y. et al., *Synthesis* 1977, 1). The 1-aminopyridium salts A-1 can react with the alkyne esters A-2 in the presence of base such as potassium carbonate in an open reaction vessel to form the bicyclic pyrazolo[1,5-a]pyridine compounds A-3. The 3-position carboxylate group can be removed by treatment in a strong acidic media, for example, in refluxing 50% sulfuric acid (Lober, S. et al *J. Med. Chem.* 2001, 44, 2691). Nitration of A-4 gave the 3-nitro compounds A-5. The nitro group is reduced to the amino by a reduction method such as zinc/calcium chloride/aqEtOH to form A-6. Reductive amination with aldehydes thus provides the dialkylated amino products (A-7, $R^7=R^8=$alkyl) or with ketone leads to the formation of the secondary amines (A-7, one of $R^7$ and $R^8$ is H). The reductive amination is carried out in the presence of a reducing agent such as sodium cyanoborohydride (see for example Lane, C. F., "Sodium Cyanoborohydride—A Highly Selective Reducing Agent for Organic Functional Groups", *Synthesis,* 1975, 135). The 3-amino compound A-7 can be treated with a strong base such as n-BuLi in THF at −78° C. to form an anion, which can be quenched with an electrophile such as 1,2-diiodoethane to form the 7-iodo products A-8 (see Aboul-Fadl, T. et. al. *Synthesis* 2000, 1727). The iodo compounds can undergo a cross-coupling reaction with a metalloaryl reagents, for example, aryl boronic acids (see for example Miyaura, N.; et al *Chem. Rev.* 1995, 95, 2457), aryl stannanes (see for example Mitchell, T. N. *Synthesis* 1992, 803), or aryl Grignards (see for example Miller, J. A. *Tetrahedron Lett.* 1998, 39, 7275), to provide the final products A-9.

CHART A

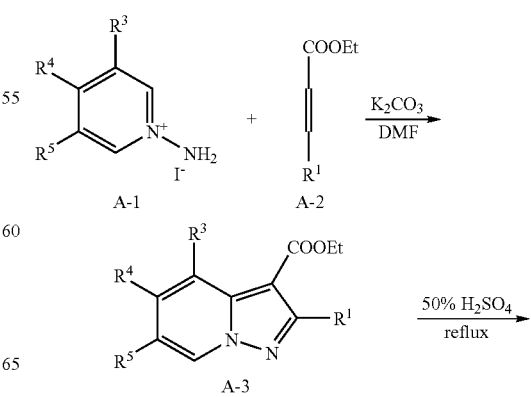

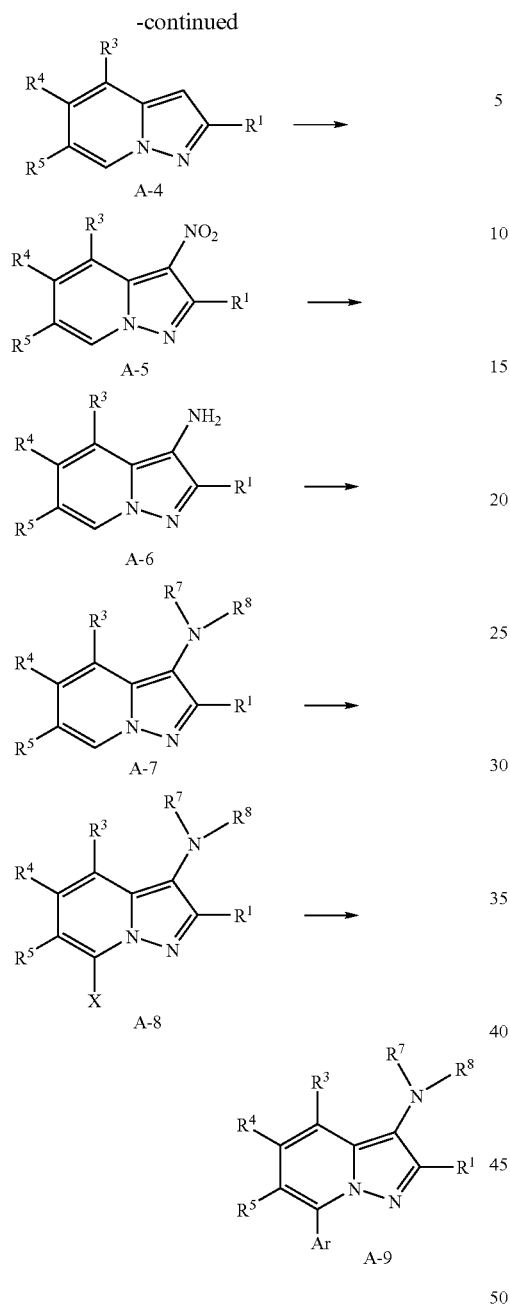

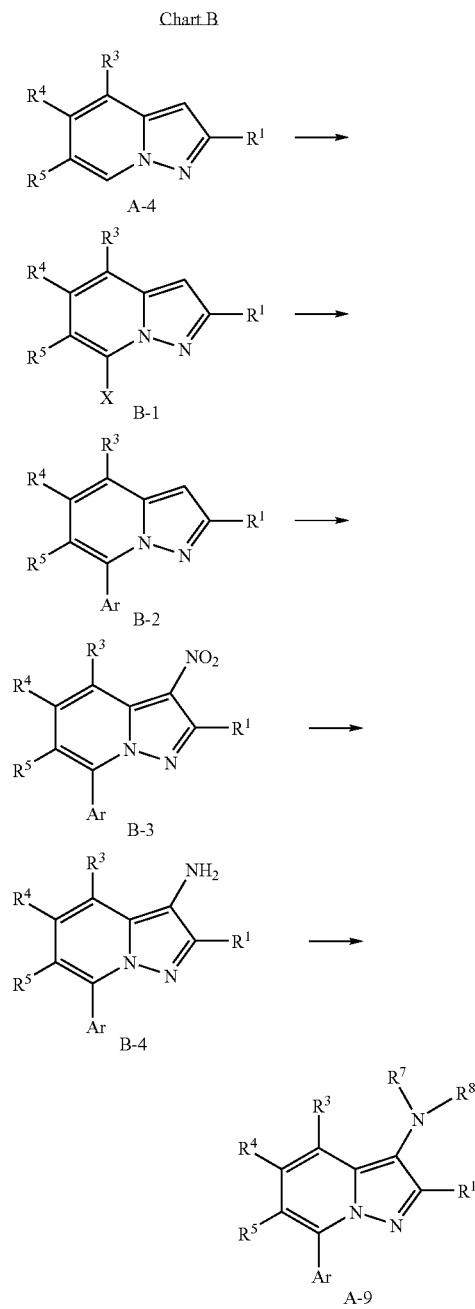

Alternatively, see Chart B, the bicyclic compounds A-4 can be lithiated with, for example, butyllithium, to generate an anion, which can be quenched with an electrophile such as 1,2-diiodoethane to form the products B-1. The iodo compounds can undergo a cross-coupling reaction with a metalloaryl reagents, for example, aryl boronic acids to provide the 7-aryl pyrazolo[1,5-a]pyridine compounds B-2. General nitration reaction provides the 3-nitro compounds B-3. The nitro group can be reduced to the amino by the method of zinc/calcium chloride/aqEtOH. The amino compounds B-4 can react with aldehyde in the presence of a reducing agent such as sodium cyanoborohydride to form the tertiary amines, or with ketones to form the secondary amines of A-9.

Alternatively, see Chart C, the 3-amino pyrazolo[1,5-a]pyridine compounds A-6 can be converted with acyl chloride reagents in the presence of a base such as triethylamine to amides C-1. Treatment of C-1 with a strong base such as sodium hydride followed by reaction with an electrophile such as alkyl halides provides the tertiary amides C-2, which can be reduced to the tertiary amines A-7 ($R^8$=$CH_2W$) by reducing agent such as lithium aluminum hydride, or borane-dimethyl sulfide complex. In certain cases, lithium aluminum hydride reaction leads to deacetylation, whereas the tertiary amine products A-7 can be still obtained by treating the deacetylated products with a base such as potassium carbonate and alkyl halides. Formation of the final products A-9 can be accomplished from A-7 as similarly as shown in Chart A.

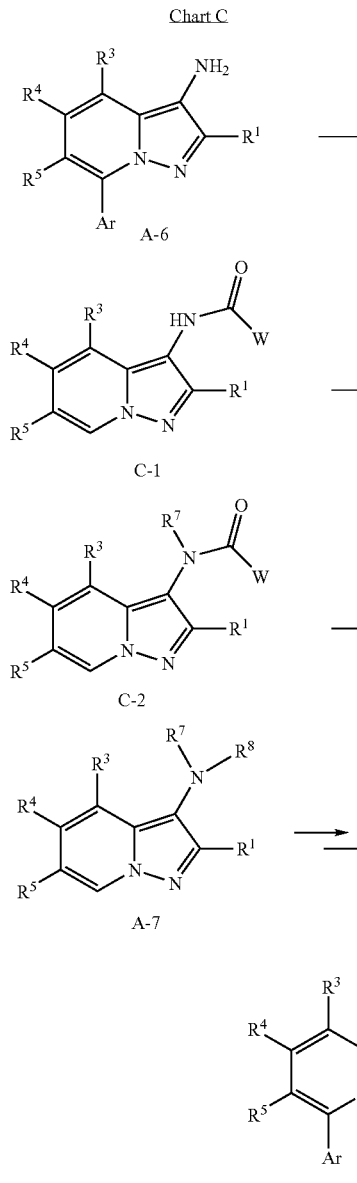

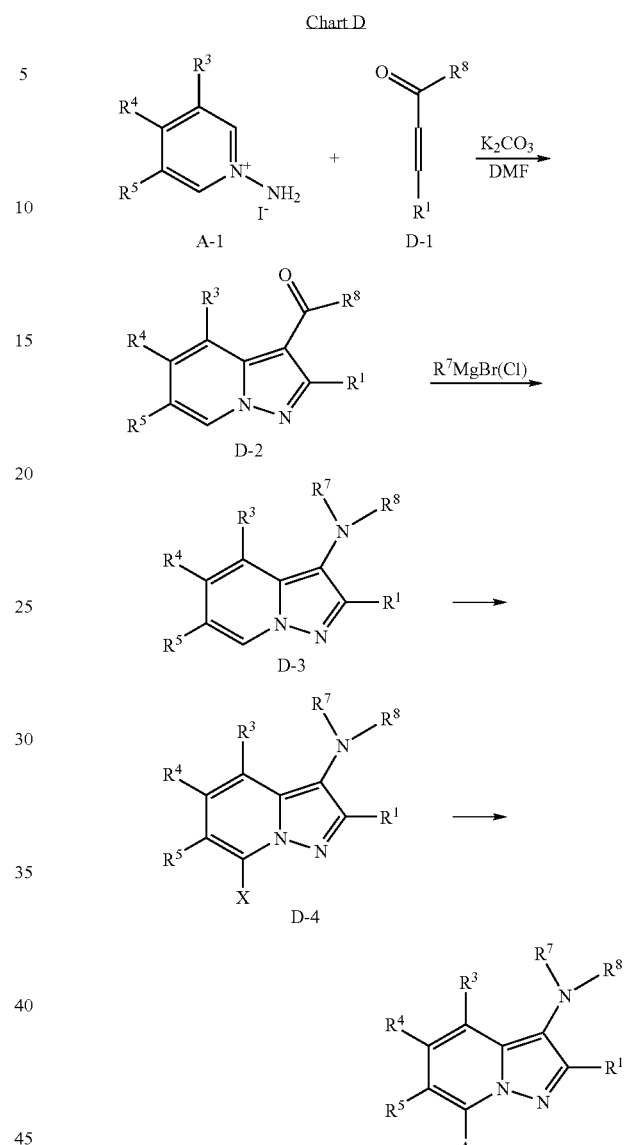

Chart D outlines the synthesis of compounds of formula I, where $R^2$ is alkyl. The bicyclic pyrazolo[1,5-a]pyridine intermediates D-2 can be synthesized from the reaction of A-1 and an alkyne ketone D-1 in the presences of a base such as potassium carbonate. Reaction of D-2 with a Grignard reagent can form an olefin intermediate, which can be reduced to the saturated compound D-3 with, for example, cyclohexene in the presence of palladium on carbon and aluminum chloride, or triethylsilane in the presence of trifluoroacetic acid. Similarly as shown in Chart A, intermediates D-3 can be converted to the halogen compounds D-4 and subsequently transformed to the targets D-5.

Alternatively, see Chart E, for the compounds of formula I having substitutents on the pyridine ring, where at least one of $R^3$, $R^4$ and $R^5$ is not H, the aromatic ring can be introduced onto the pyridine template E-1 by carrying out a cross coupling reaction of 2-halopyridines E-1 with a metalloaryl reagent such as aryl boronic acid to form the 2-aryl pyridines E-2. The pyridium salts E-3 can be prepared from E-2 by reacting with an aminating reagent such as O-mesitylenesulfonylhydroxylamine which is generated in situ from ethyl O-mesitylsulfonylacetohydroxamate. Cycloaddition of E-3 with the alkyne reagent A-2 leads to the formation of pyrazolo[1,5-a]pyridine compounds E-4. After hydrolysis, the carboxylic acid intermediates E-5 can undergo Curtius-Schmidt rearrangement by reaction with an azide reagent such as diphenylphosphoryl azide to form the 3-amino pyrazolo[1,5-a]pyridine compounds B-4.

Chart E

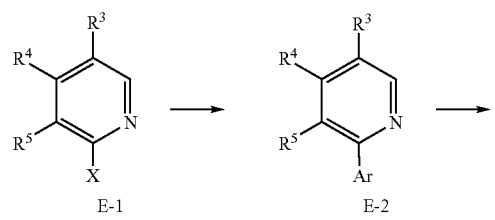

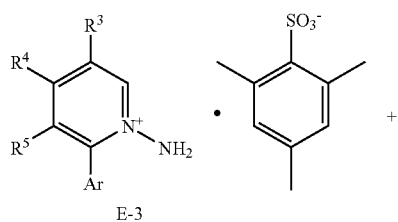

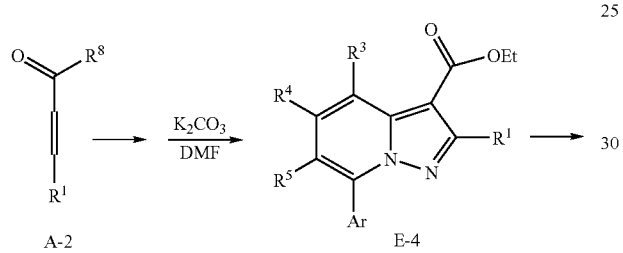

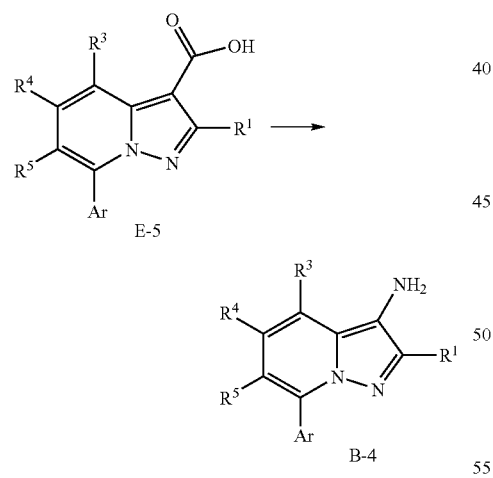

Chart F illustrates the synthesis of compounds of formula T. The products F-2 can be prepared from the halogenated intermediates F-1 by reaction with an aryl hydroxy compound in the presence of a metal promoting agent such as palladium or copper reagents and base such as potassium carbonate (see Sugahara, M. et al *Chem. Pharm. Bull.* 1997, 45, 719 and Marcoux, J.-F. et al *J. Am. Chem. Soc.* 1997, 119, 10539 and Aranyos, A. et al *J. Am. Chem. Soc.* 1999, 121, 4369).

Chart F

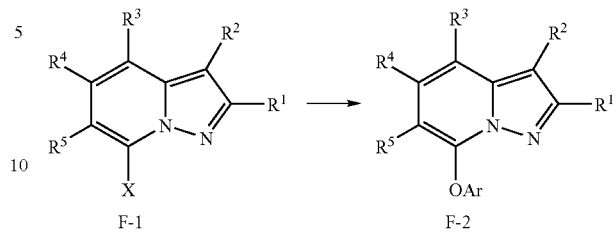

Chart G illustrates the synthesis of compounds of formula I where $R^6$ is pyridone and linked at the nitrogen. Intermediates A-7 (U=H) can be treated with a strong base such as butyllithium and the generated anion can react with tosyl azide (see Reed, J. N. et al *Tetrahedron Lett.* 1983, 24, 3795) to provide the 7-amino pyrazolo[1,5-a]pyridine compounds G-1. Alternatively, intermediates A-8 (U=halogen) can react with benzophenone imine under the catalysis of palladium to form the 7-amino pyrazolo[1,5-a]pyridine compounds G-1 (see Wolfe, J. P. et al *Tetrahedron Lett.* 1997, 38, 6367). The amino compounds G-1 can react with a 2-pyrone to produce the pyridone compound G-2 (see Wiley, R. H. et al *J. Am. Chem. Soc.* 1956, 78, 2393).

Chart G

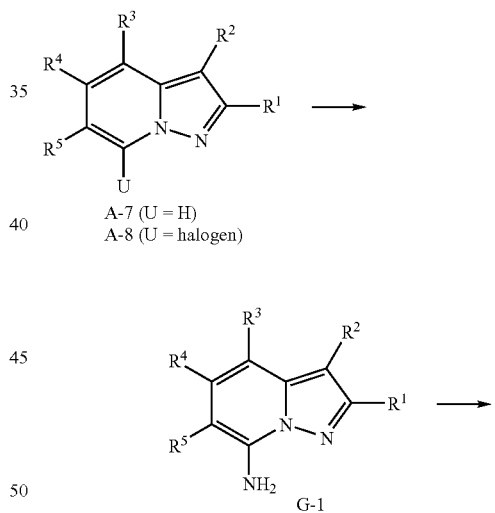

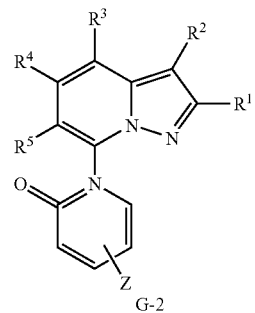

Compounds of formula I where $R^2$ is a cyclic amine and linked at nitrogen can be synthesized as illustrated in Chart H (see Nakazato, A. et al WO 0202549). The 3-amino pyrazolo[1,5-a]pyridine compounds B-4 can react with 1,5-dichloro-3-pentanone to form the piperidone products H-1. Reaction of H-1 with potassium cyanide provides the cyano compounds H-2, which can undergo acidic hydrolysis to produce the amides H-3. Introduction of $R^9$ and $R^{10}$ can be accomplished by treatment of H-3 with a strong base such as sodium hydride and an electrophile such as alkyl halides or palladium catalysis with aryl halides (see Kang, S.-K. et al Synlett 2002, 427).

Chart G

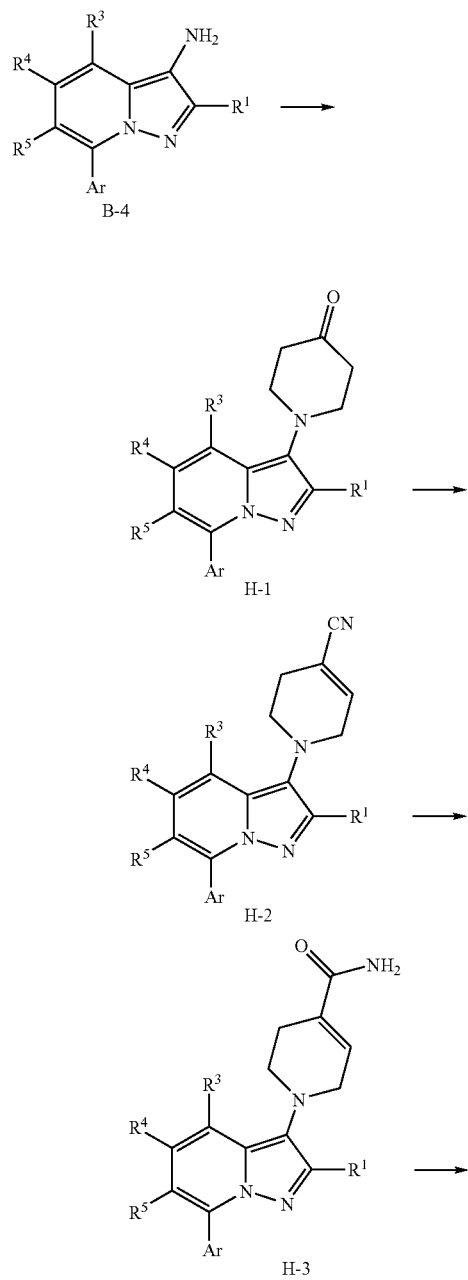

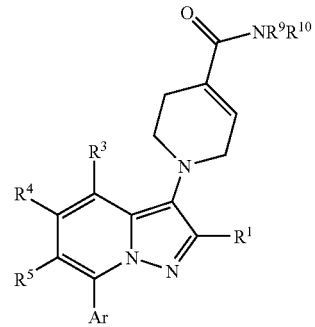

-continued

H-4

The present invention also encompasses pharmaceutically acceptable salts of compounds of formula I. Examples of pharmaceutically acceptable salts are salts prepared from inorganic acids or organic acids, such as inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, omithine, choline, N,N'-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like.

Pharmaceutically acceptable salts of the compounds of the invention can be prepared by conventional chemical methods. Generally, such salts are, for example, prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

In another aspect, the present invention provide a prodrug of a compound of formula I. The prodrug is prepared with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). See e.g. T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs include, but are not limited to, compounds derived from compounds of formula I wherein hydroxy, amine or sulfhydryl groups, if present, are bonded to any group that, when administered to the subject, cleaves to form the free hydroxyl, amino or sullhydryl group, respectively. Selected examples include, but are not limited to, biohydrolyzable amides and biohydrolyzable esters and biohydrolyzable carbamates, carbonates, acetate, formate and benzoate derivatives of alcohol and amine functional groups.

The prodrug can be readily prepared from the compounds of formula I using methods known in the art. See, e.g. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172–178, 949–982 (1995). For example, the compounds of formula I can be transformed into prodrugs by converting one or more of the hydroxy or carboxy groups into esters. For example, prodrugs of the compounds of formula I can be prepared by modifying functional groups present on the compound in such a way that the modifications are cleaved, either in routine manipulation or in vivo, to the parent compound.

The invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$, and $^{125}I$. Compounds of formula I that contain the aforementioned isotopes and/or other isotopes of other atoms are within the scope of the invention. Isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly useful in PET (positron emission tomography), and $^{125}I$ isotopes are particularly useful in SPECT (single photon emission computed tomography); all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, maybe preferred in some circumstances. Isotopically labeled compounds of formula I of this invention can generally be prepared by carrying out the synthetic procedures by substituting a isotopically labeled reagent for a non-isotopically labeled reagent.

Preferably compounds of the invention exhibit an $IC_{50}$ value for CRF binding of 1 micromolar or less, more preferably of 100 nanomolar or less and even more preferably of 10 nanomolar or less.

The compounds of formula I are antagonists at the CRF receptor and are useful in the treatment of anxiety disorders, depression and stress related disorders. The compounds are also useful in smoking cessation programs. The method of treatment involves administration to a mammal (e.g. a human) an effective amount of a compound of the invention. In particular, therapeutically effective amounts of the compounds of this invention are amounts effective to antagonize, or lower, levels of corticotropin releasing factor (CRF) in mammals, thereby alleviating in the mammals conditions characterized by abnormally high levels of CRF expression.

In another aspect, the present invention provides a pharmaceutical composition comprising a compound of formula I, a stereoisomer thereof, a pharmaceutically acceptable salt thereof, or a prodrug thereof, or a pharmaceutically acceptable salt of the prodrug thereof. In one embodiment, the pharmaceutical composition further comprises a pharmaceutically acceptable carrier, diluent, or excipient therefore. A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, $17^{th}$ ed., Mack Publishing Company, Easton, Pa., 1985, the contents of which are incorporated herein by reference.

These compounds of formula I may be administered orally, topically, parenterally, by inhalation or spray or rectally in dosage unit formulations containing conventional non-toxic pharmaceutically acceptable carriers, adjuvants and vehicles.

The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to methods known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and a delay material such as glyceryl monosterate or glyceryl disteatate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long aliphatic alcohols, for example heptadecaethyleneoxycetanol, or condensation products of ethylene oxide with partial esters derived from fatty acids and a hexital such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occuring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds of general formula I may also be administered in the form of suppositories for rectal administration of the drug. These compositions can be prepared by mixing the drug with a suitable non-irritating excipient, which is solid at ordinary temperatures but liquid at the rectal temperature and will therefore melt in the rectum to release the drug. Such materials are cocoa butter and polyethylene glycols.

The pharmaceutical compositions containing compounds of general formula I may be in a form suitable for parenteral use. The term "parenteral" as used herein includes subcutaneous injections, intravenous, intramuscular, intrasternal injection or infusion techniques.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable solution or suspension may be formulated in a non-toxic parentally acceptable diluent or solvent, for example as a solution in 1,3-butanediol. Among the acceptable vehicles and solvents that may be employed are water, Ringers's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms suitable for administration generally contain from about 1 mg to about 100 mg of active ingredient per unit. In these pharmaceutical compositions, the active ingredient will ordinarily be present in an amount of about 0.5 to 95% by weight based on the total weight of the composition. Examples of dosage forms for administration of the compounds of this invention includes the following: (1) Capsules. A large number of units capsules are prepared by filling standard two-piece hard gelatin capsules each with 100 mg of powdered active ingredient, 150 mg lactose, 50 mg cellulose, and 6 mg magnesium stearate; (2) Soft Gelatin Capsules. A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried; (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

In another aspect, the present invention provides a method of antagonizing $CRF_1$ receptors in a warm-blooded animal, comprising administering to the animal a compound of the invention at amount effective to antagonize $CRF_1$ receptors. The warm-blooded animal is preferably a mammal, and more preferably a human.

In another aspect, the present invention provides a method of treating a disorder in a warm-blooded animal, which disorder manifests hypersecretion of CRF, or the treatment of which disorder can be effected or facilitated by antagonizing $CRF_1$ receptors, comprising administering to the animal a therapeutically effective amount of a compound of the invention. The warm-blooded animal is preferably a mammal, and more preferably a human.

In another aspect, the present invention provides a method for screening for ligands for $CRF_1$ receptors, which method comprises: a) carrying out a competitive binding assay with $CRF_1$ receptors, a compound of formula I which is labelled with a detectable label, and a candidate ligand; and b) determining the ability of said candidate ligand to displace said labelled compound. One method for this assay is described in Example A.

In another aspect, the present invention provides a method for detecting CRF receptors in tissue comprising: a) contacting a compound of formula I, which is labelled with a detectable label, with a tissue, under conditions that permit binding of the compound to the tissue; and b) detecting the labelled compound bound to the tissue. Assay procedure for detecting receptors in tissues is well known in the art.

In another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the $CRF_1$ receptor. An example of the cell line that expresses the $CRF_1$ receptor and can be used in the in vitro assay is IMR32 cells known in the art.

In another aspect, the present invention provides an article of manufacture comprising: a) a packaging material; b) a pharmaceutical agent comprising a compound of the invention contained within said packaging material; and c) a label or package insert which indicates that said pharmaceutical agent can be used for treating a disorder described below.

Compounds of the invention are useful for treating various disorders in a mammal including social anxiety disorder; panic disorder; obsessive-compulsive disorder; anxiety with co-morbid depressive illness; affective disorder; anxiety; depression; irritable bowel syndrome; post-traumatic stress disorder; supranuclear palsy; immune suppression; gastrointestinal disease; anorexia nervosa or other feeding disorder; drug or alcohol withdrawal symptoms; substance abuse disorder (e.g., nicotine, cocaine, ethanol, opiates, or other drugs); inflammatory disorder; fertility problems; disorders the treatment of which can be effected or facilitated by antagonizing CRF, including but not limited to disorders induced or facilitated by CRF; a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); osteoporosis; psychosocial dwarfism and hypoglycemia.

Thus, in still another aspect, the present invention provides a method of treating a disorder described herein above, comprising administering to the mammal a therapeutically effective amount of a compound of the invention.

Particular disorders that can be treated by the method of the invention preferably include the following: generalized anxiety disorder; social anxiety disorder; anxiety; obsessive-compulsive disorder; anxiety with co-morbid depressive illness; panic disorder; mood disorders such as depression, including major depression, single episode depression, recurrent depression, child abuse induced depression, and postpartum depression; bipolar disorders; post-traumatic stress disorder; substance abuse disorder (e.g., nicotine, cocaine, ethanol, opiates, or other drugs); inflammatory disorders such as rheumatoid arthritis and osteoarthritis; gastrointestinal diseases such as irritable bowel syndrome, ulcers, Crohn's disease, spastic colon, diarrhea, and post operative ilius and colonic hypersensitivity associated by psychopathological disturbances or stress; inflammatory disorder; and skin disorders such as acne and psoriasis.

Particular disorders that can be treated by the method of the invention more preferably include the following: generalized anxiety disorder; social anxiety disorder; anxiety;

obsessive-compulsive disorder; anxiety with co-morbid depressive illness; panic disorder; and mood disorders such as depression, including major depression, single episode depression, recurrent depression, child abuse induced depression, and postpartum depression.

A compound of this invention can be administered to treat the above disorders or abnormalities by means that produce contact of the active agent with the agent's site of action in the body of a mammal, such as by oral or parenteral administration using appropriate dosage forms. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

Definitions and Conventions

The following definitions are used throughout the application, unless otherwise described.

The term "alkyl" means a straight or branched chain moiety having from 1–10 carbon atoms optionally containing one or more double or triple bonds;

The term "substituted alkyl" means an alkyl moiety having 1–3 substituents independently selected from halogen, $-OR^9$, $-S(O)_mR^9$, $-NR^9R^{10}$, $-C(O)R^9$, $-C(S)R^9$, $-CN$, $-C(O)NR^9R^{10}$, $-C(S)NR^9R^{10}$, $-NR^9C(O)R^{10}$, $-NR^9C(S)R^{10}$, $-S(O)_nNR^9R^{10}$, $-NR^9S(O)_nR^{10}$, $-NO_2$, $-COOR^9$, $-C(S)OR^9$, $-OC(O)R^9$, $-OC(S)R^9$, and Ar, provided that a halogen or halogens may not be the only substituent(s) on the alkyl group;

The term "cycloalkyl" means a monocyclic or bicyclic alkyl moiety, having from 3–10 carbon atoms optionally containing 1 to 2 double bonds provided that the moiety is not aromatic;

The term "substituted cycloalkyl" means a cycloalkyl group having 1–3 substituents independently selected from halogen, $-R^9$, $-OR^9$, $-S(O)_mR^9$, $-NR^9R^{10}$, $-C(O)R^9$, $C(S)R^9$, $-CN$, $-C(O)NR^9R^{10}$, $-C(S)NR^9R^{10}$, $-NR^9C(O)R^9$, $-NR^9C(S)R^9$, $-S(O)_nNR^9R^9$, $-NR^9S(O)_nR^{10}$, and $-NO_2$, $-C(O)OR^9$, $-C(S)OR^9$, $-OC(O)R^9$, $-OC(S)R^9$, and Ar, provided that a halogen or halogens may not be the only substituent(s) on the alkyl group;

The term "heterocycloalkyl" means a 3- to 8-membered mono-carboxylic ring or bicyclic ring, wherein at least one carbon atom is replaced with a heteromember selected from oxygen, $-N=$, $-NH-$ and $-NR^9-$, or $-S(O)_m-$, optionally containing from one to three double bonds;

The term "substituted heterocycloalkyl" means a heterocycloalkyl group having 1–3 substituents independently selected from halogen, $-R^9$, $-OR^9$, $-S(O)_mR^9$, $-NR^9R^{10}$, $-C(O)R^9$, $C(S)R^9$, $-CN$, $-C(O)NR^9R^{10}$, $-C(S)NR^9R^{10}$, $-NR^9C(O)R^{10}$, $-NR^9C(S)R^{10}$, $-S(O)_nNR^9R^9$, $-NR^9S(O)_nR^{10}$, and $-NO_2$, $-C(O)OR^9$, $-C(S)OR^9$, $-OC(O)R^9$, $-OC(S)R^9$, and Ar, provided that a halogen or halogens may not be the only substituent(s) on the alkyl group;

The term "aryl" means a monocyclic or bicyclic aromatic group having 6 to 10 carbon atoms;

The term "substituted aryl" means an aryl group having 1–5 substituents independently selected from halogen, $-NO_2$, $-CN$, $-R^9$, $-OR^9$, $-S(O)_mR^9$, $-NR^9R^{10}$, $-C(O)NR^9R^{10}$, $-C(S)NR^9R^{10}$ $-S(O)_nNR^9R^{10}$, $-NR^9S(O)_nR^{10}$, $-NR^9C(O)OR^{10}$, $-NR^9C(S)OR^{10}$, $-OC(O)NR^9R^{10}$, $-OC(S)NR^9R^{10}$, $-NR^9C(O)NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

The term "heteroaryl" means a radical attached via a ring carbon or nitrogen atom of a monocyclic aromatic ring containing five or six ring atoms consisting of carbon and 1, 2, 3, or 4 heteroatoms each selected from the group consisting of non-peroxide O, S, N, with appropriate bonding to satisfy valence requirements. The term also means a radical (attachment at either carbon or nitrogen) of a fused bicyclic heteroaromatic of about seven to ten ring atoms. Examples of heteroaryl includes, but not limited to, radicals such as thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl;

The term "substituted heteroaryl" means a heteroaryl group having 1–5 substituents independently selected from halogen, $-NO_2$, $-CN$, $-R^9$, $-OR^9$, $-S(O)_mR^9$, $-NR^9R^{10}$, $-C(O)NR^9R^{10}$, $-C(S)NR^9R^{10}-S(O)_nNR^9R^{10}$, $-NR^9S(O)_nR^{10}$, $-NR^9C(O)OR^{10}$, $-NR^9C(S)OR^{10}$, $-OC(O)NR^9R^{10}$, $-OC(S)NR^9R^{10}$, $-NR^9C(O)$ $NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

The term "aryl cycloalkyl" means a bicyclic ring system containing 8 to 14 carbon atoms wherein one ring is aryl and the other ring is fused to the aryl ring and may be fully or partially saturated in the portion of the ring not fused to the aryl ring, and wherein either ring may act as a point of attachment;

The term "substituted aryl cycloalkyl" means an aryl cycloalkyl group having 1–3 substituents independently selected from halogen, $-NO_2$, $-CN$, $-R^9$, $-OR^9$, $-S(O)_m R^9$, $-NR^9R^{10}$, $-C(O)NR^9R^{10}$, $-C(S)NR^9R^{10}$—$S(O)_n$ $NR^9R^{10}$, $-NR^9S(O)_n R^{10}$, $-NR^9C(O)OR^{10}$, $-NR^9C(S)OR^{10}$, $-OC(O)NR^9R^{10}$, $-OC(S)NR^9R^{10}$, $-NR^9C(O)NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

The term "heteroaryl cycloalkyl" means a bicyclic ring system containing 7 to 14 atoms, wherein one ring is heteroaryl and the other ring is fused to the heteroaryl ring and may be fully or partially saturated in the portion of the ring fused to the heteroaryl ring, and wherein either ring may act as a point of attachment;

The term "substituted heteroaryl cycloalkyl" means a heteroaryl cycloalkyl group having 1–5 substituents independently selected from halogen, $-NO_2$, $-CN$, $-R^9$, $-OR^9$, $-S(O)_m R^9$, $-NR^9R^{10}$, $-C(O)NR^9R^{10}$, $-C(S)NR^9R^{10}$—$S(O)_n NR^9R^{10}$, $-NR^9S(O)_n R^{10}$, $-NR^9C(O)OR^{10}$, $-NR^9C(S)OR^{10}$, $-OC(O)NR^9R^{10}$, $-OC(S)NR^9R^{10}$, $-NR^9C(O)NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

The term "aryl heterocycloalkyl" means a bicyclic ring system containing 8 to 14 atoms, wherein one ring is aryl and the other ring is heterocloalkyl, and wherein either ring may act as a point of attachment;

The term "substituted aryl heterocycloalkyl" means an aryl heterocycloalkyl having 1–3 substituents independently selected from halogen, $-NO_2$, $-CN$, $-R^9$, $-OR^9$, $-S(O)_m R^9$, $-NR^9R^{10}$, $-C(O)NR^9R^{10}$, $-C(S)NR^9R^{10}$—$S(O)_n$ $NR^9R^{10}$, $-NR^9S(O)_n R^{10}$, $-NR^9C(O)OR^{10}$, $-NR^9C(S)OR^{10}$, $-OC(O)NR^9R^{10}$, $-OC(S)NR^9R^{10}$, $-NR^9C(O)NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

The term "heteroaryl heterocycloalkyl" means a bicyclic ring system containing 7 to 14 atoms, wherein one ring is heteroaryl and the other ring is heterocycloalkyl, and wherein either ring may act as a point of attachment;

The term "substituted heteroaryl heterocycloalkyl" means an heteroaryl heterocycloalkyl having 1–3 substituents independently selected from halogen, $-NO_2$, $-CN$, $-R^9$, $-OR^9$, $-S(O)_m R^9$, $-NR^9R^{10}$, $-C(O)NR^9R^{10}$, $-C(S)NR^9R^{10}$—$S(O)_n NR^9R^{10}$, $-NR^9S(O)_n R^{10}$, $-NR^9C(O)OR^{10}$, $-NR^9C(S)OR^{10}$, $-OC(O)NR^9R^{10}$, $-OC(S)NR^9R^{10}$, $-NR^9C(O)NR^9R^{10}$, $-NR^9C(S)NR^9R^{10}$, $-C(O)OR^9$, $-C(S)OR^9$, $-OC(O)R^9$, $-OC(S)R^9$ and $-OC(O)OR^9$;

$R^9$ and $R^{10}$ can be the same or different and are independently selected from $-H$, alkyl, substituted alkyl, cycloalkyl, substituted cycloalkyl, and Ar;

Ar is selected from aryl, substituted aryl, heteroaryl, and substituted heteroaryl;

Halogen is a group selected from $-F$, $-Cl$, $-Br$, $-I$;

m is 0, 1 or 2; and n is 1 or 2.

The term "pharmaceutically acceptable salt" refers to a salt which retains the biological effectiveness and properties of the compounds of this invention and which is not biologically or otherwise undesirable. Typical pharmaceutically acceptable salts include those salts prepared by reaction of the compounds of the present invention with a pharmaceutically acceptable mineral or organic acid or an organic or inorganic base. Such salts are known as acid addition and base addition salts.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "prodrug" means compounds that are transformed in vivo to yield a compound of Formula I. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "therapeutically effective amount," "effective amount," "therapeutic amount," or "effective dose" is meant that amount sufficient to elicit the desired pharmacological or therapeutic effects, thus resulting in effective prevention or treatment of the disease.

The term "pharmaceutically acceptable" refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The phrases "a compound of the invention," "a compound of the present invention," "compounds of the present invention," or "a compound in accordance with Formula I" and the like, refer to compounds of formula I, or stereoisomers thereof, pharmaceutically acceptable salts thereof, or prodrugs thereof, or pharmaceutically acceptable salts of a prodrug of compounds of formula I.

The terms "treatment," "treat," "treating," and the like, are meant to include both slowing or reversing the progression of a disorder, as well as curing the disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

EXAMPLES

Without further elaboration, it is believed that one skilled in the art can, using the preceding description, practice the present invention to its fullest extent. The following examples are provided to describe the invention in further detail. They are intended to illustrate and not to limit the invention in any way whatsoever. Examples 1–40 provide exemplary compounds and illustrate the preparation thereof. Examples A–D illustrate various biological assays that can be used for determining the biological properties of the compounds of the inventions. Those skilled in the art will promptly recognize appropriate variations from the procedures described in the examples.

Example 1

7-(2,4-dichlorophenyl)-N,N-diethylpyrazolo[1,5-a]pyridin-3-amine

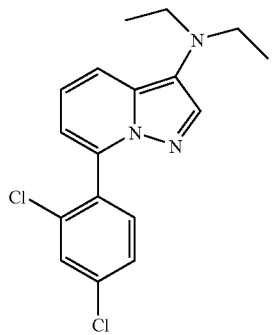

Step 1

Preparation of 3-nitropyrazolo[1,5-a]pyridine

To a solution of pyrazolo[1,5-a]pyridine (2.36 g, 20.0 mmol) (Lober, S. et al *J. Med. Chem.* 2001, 44, 2691) in concentrated sulfuric acid (20.0 mL) was added the freshly prepared solution of ammonium nitrate (1.84 g, 23.0 mmol) in concentrated sulfuric acid (25.0 mL) dropwise at −5° C. The resulting mixture was stirred at 0° C. for 2 h and added dropwise to a solution of 4 N sodium hydroxide (200 mL) at 0° C. followed by the addition of sodium bicarbonate (60.0 g). Water and ether were added and separated. The aqueous solution was extracted with dichloromethane (2×). The combined organic solution was dried ($MgSO_4$) and filtered. The filtrate was concentrated in vacuo to dryness to give 2.49 g (76%) of beige solid as the title compound: mp 179–182° C. ($CH_2Cl_2$/hexanes); $^1H$ NMR (400 MHz, $CDCl_3$) δ 8.68 (s, 1H), 8.63 (dd, J=2.0, 6.9 Hz, 1H), 8.41 (dd, J=2.3, 8.9 Hz, 1H), 7.74 (dd, J=7.0, 8.9 Hz, 1H), 7.21 (dd, J=7.0, 7.0 Hz, 1H); IR (diffuse reflectance) 2480, 2465, 2417, 2392, 2350, 1636, 1512, 1479, 1464, 1408, 1288, 1252, 1194, 882, 773 $cm^{-1}$; MS (EI) m/z 163 ($M^+$); HRMS (FAB) calcd for $C_7H_5N_3O_2$+H 164.0460. found 164.0459; Anal. Calcd for $C_7H_5N_3O_2$: C, 51.54; H, 3.09; N, 25.76. Found: C, 51.42; H, 2.95; N, 25.71.

Step 2

Preparation of pyrazolo[1,5-a]pyridin-3-amine

To a mixture of 3-nitropyrazolo[1,5-a]pyridine (2.35 g, 14.4 mmol) and zinc (28.2 g, 432 mmol) in 78% ethanol (75.0 mL) was added a solution of calcium chloride (0.8 g, 7.2 mmol) in a minimum amount of water. The resulting mixture was refluxed for 2 h and filtered in hot and washed with hot ethanol. The filtrate was concentrated in vacuo to dryness and the residue was subjected to column chromatography (EtOAc) to give an orangish solid as the desired product (1.48 g, 77%): $^1H$ NMR (400 MHz, $CDCl_3$) δ 8.31 (d, J=7.0 Hz, 1H), 7.69 (s, 1H), 7.44 (d, J=9.0 Hz, 1H), 7.01–6.96 (m, 1H), 6.68–6.64 (m, 1H), 2.90 (br, 2H); MS (EI) m/z 134 ($M^++H$).

Step 3

Preparation of N,N-diethylpyrazolo[1,5-a]pyridin-3-amine

A solution of 3-aminopyrazolo[1,5-a]pyridine (0.74 g, 5.55 mmol) in acetonitrile (15.0 mL) was treated with acetaldehyde (6.2 mL, 4.89 g, 111 mmol) and $NaCNBH_3$ (0.84 g, 13.3 mmol) and stirred at room temperature for 3 days. The reaction was concentrated in vacuo and the residue partitioned between ethyl acetate and saturated $NaHCO_3$ solution. The layers were separated and the aqueous layer was extracted with ethyl acetate (2×). The organic layers were combined, washed with brine, dried over $MgSO_4$ and concentrated in vacuo to dryness. The residue was subjected to column chromatography (15% ethyl acetate/hexane) to give 0.61 g (58%) of a yellow oil as the title compound: MS (EI) m/z 190 ($M^++H$).

Step 4

Preparation of N,N-diethyl-7-iodopyrazolo[1,5-a]pyridin-3-amine

A solution of 3-diethylaminopyrazolo[1,5-a]pyridine (0.57 g, 3.00 mmol) in THF (5.00 mL) was cooled to −78° C. and treated with a solution of n-butyl lithium (1.20 M in hexanes, 3.25 mL, 3.90 mmol). The reaction was stirred for 30 minutes then treated with a solution of 1,2-diiodoethane (1.01 g, 3.60 mmol) in THF (10 mL). The reaction was stirred at −78° C. for 3 hours then quenched with saturated $NaHCO_3$ at −78° C. and warmed to room temperature. The reaction was diluted with water and extracted twice with methylene chloride, dried over $MgSO_4$ and concentrated in vacuo to give a dark green oil which was subjected to column chromatography (5% ethyl acetate/hexane) to give 0.59 g (63%) of a yellow oil as the title compound: $^1H$ NMR (400 MHz, $CDCl_3$) δ 7.92 (s, 1H), 7.58 (dd, J=8.8, 1.2 Hz, 1H), 7.31 (d, J=8.0 Hz, 1H), 6.81–6.76 (m, 1H), 3.13 (q, J=7.1 Hz, 4H), 1.06 (t, J=7.1 Hz, 6H); MS (EI) m/z 316.14 ($M^++H$).

Step 5

Preparation of 7-(2,4-dichlorophenyl)-N,N-diethylpyrazolo[1,5-a]pyridin-3-amine

A solution of 3-diethylamino-7-iodopyrazolo[1,5-a]pyridine (0.20 g, 0.63 mmol) and Pd(PPh$_3$)$_4$ (0.037 g, 0.03 mmol) in DME (5.0 mL) was stirred at room temperature for 10 minutes then treated with 2,4-dichlorophenylboronic acid (0.19 g, 1.27 mmol) and 2M Na$_2$CO$_3$ (3.0 mL). The reaction was heated at 80° C. for 16 hours and cooled down to room temperature. Additional Pd(PPh$_3$)$_4$ (0.037 mg, 0.03 mmol) and 2,4-dichlorophenylboronic acid (0.19 g, 1.27 mmol) were added and heating was continued at 80° C. for 2 hours. The reaction was partitioned between ethyl acetate and water. The aqueous layer was extracted with ethyl acetate (2×). The combined organic solutions was washed with brine, dried over MgSO$_4$, and concentrated in vacuo to dryness. The residue was subjected to column chromatography (5% ethyl acetate/hexane) to give 0.17 g (79%) of a light yellow oil as the title compound: $^1$H NMR (400 MHz, CDCl$_3$) δ 7.81 (s, 1H), 7.66–7.63 (m, 2H), 7.50 (d, J=8.2 Hz, 1H), 7.44 (d, J=8.2 Hz, 1H), 7.14–7.09 (m, 1H), 6.71 (d, J=6.7 Hz, 1H), 3.15 (q, J=7.1 Hz, 4H), 1.09 (t, J=7.1 Hz, 6H); IR (diffuse reflectance) 2968, 2935, 2814, 1487, 1461, 1377, 1334, 1314, 1149, 1096, 921, 881, 867, 827, 791 cm$^{-1}$; MS (EI) m/z 333 (M$^+$); Anal. Calcd for C$_{17}$H$_{17}$Cl$_2$N$_3$: C, 61.09; H, 5.13; N, 12.57. Found: C, 60.97; H, 5.02; N, 12.54.

Example 2

7-(2,4-dichlorophenyl)-N,N-dipropylpyrazolo[1,5-a]pyridin-3-amine

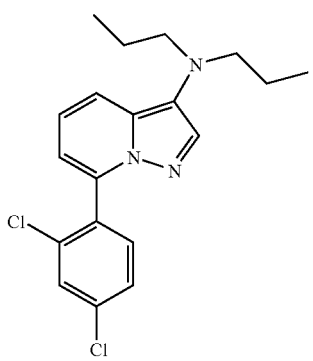

Step 1

Preparation of N,N-dipropylpyrazolo[1,5-a]pyridin-3-amine

Following the general procedure of EXAMPLE 1 (Step 3) and making non-critical variations, the title compound was prepared as a yellow oil (76%): $^1$H NMR (400 MHz, CDCl$_3$) δ 8.34 (d, J=7.0 Hz, 1H), 7.81 (s, 1H), 7.54 (d, J=8.9 Hz, 1H), 7.00 (dd, J=7.0, 8.5 Hz, 1H), 6.69 (dd, J=6.7, 6.6 Hz, 1H), 3.00 (t, J=7.4 Hz, 4H), 1.52–1.43 (m, 4H), 0.92 (t, J=7.4 Hz, 6H); $^{13}$C NMR (100 MHz, CDCl$_3$) δ 136.1, 135.4, 129.0, 125.7, 121.7, 117.6, 111.8, 58.6, 21.3, 12.1; IR (diffuse reflectance) 2959, 2934, 2873, 2815, 2430, 2313, 1996, 1913, 1474, 1467, 1357, 1331, 1084, 752, 735 cm$^{-1}$; MS (EI) m/z 217 (M$^+$); HRMS (FAB) calcd for C$_{13}$H$_{19}$N$_3$+H 218.1657. found 218.1654.

Step 2

Preparation of N,N-dipropyl-7-iodopyrazolo[1,5-a]pyridin-3-amine

Following the general procedure of EXAMPLE 1 (Step 4) and making non-critical variations, the title compound was prepared as a yellow oil (61%): $^1$H NMR (400 MHz, CDCl$_3$) δ 7.92 (s, 1H), 7.58 (d, J=8.7 Hz, 1H), 7.29 (d, J=7.2 Hz, 1H), 6.77 (dd, J=7.2, 8.6 Hz, 1H), 3.00 (t, J=7.4 Hz, 4H), 1.52–1.43 (m, 4H), 0.91 (t, J=7.4 Hz, 6H); IR (diffuse reflectance) 2958, 2932, 2871, 2815, 2405, 2049, 1905, 1513, 1454, 1336, 1295, 1196, 1096, 894, 772 cm$^{-1}$; MS (EI) m/z 343 (M$^+$); HRMS (FAB) calcd for C$_{13}$H$_{18}$IN$_3$+H 344.0625. found 344.0616.

Step 3

Preparation of 7-(2,4-dichlorophenyl)-N,N-dipropylpyrazolo[1,5-a]pyridin-3-amine Following the general procedure of EXAMPLE 1 (Step 5) and making non-critical variations, the title compound was prepared as a yellow oil (39%): $^1$H NMR (400 MHz, CDCl$_3$) δ 7.80 (s, 1H), 7.65–7.61 (m, 2H), 7.50 (d, J=8.2 Hz, 1H), 7.43 (dd, J=8.2, 2.0 Hz, 1H), 7.12–7.09 (m, 1H), 6.70 (d, J=6.4 Hz, 1H), 3.03 (t, J=7.0 Hz, 4H), 1.54–1.48 (m, 4H), 0.92 (t, J=7.3 Hz, 6H); $^{13}$C NMR (100 MHz, CDCl$_3$) δ 136.9, 136.4, 135.9, 135.7, 135.5, 132.8, 132.0, 130.4, 127.8, 126.4, 121.2, 117.8, 113.7, 58.5, 21.4, 12.1; IR (diffuse reflectance) 2959, 2933, 2872, 2815, 2398, 1902, 1591, 1534, 1486, 1463, 1339, 1314, 1101, 820, 786 cm$^{-1}$; MS (EI) m/z 361 (M$^+$); HRMS (FAB) calcd for C$_{19}$H$_{21}$Cl$_2$N$_3$+H 362.1190. found 362.1186.

Example 3

N-(Cyclopropylmethyl)-N-ethyl-7-(2,4-dichlorophenyl)pyrazolo[1,5-a]pyridin-3-amine

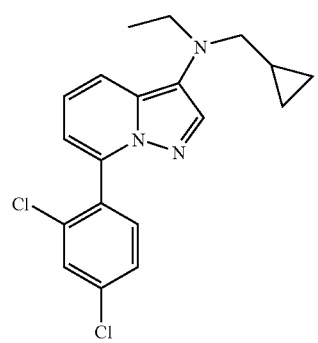

Step 1

Preparation of N-pyrazolo[1,5-a]pyridin-3-ylcyclopropanecarboxamide

To a solution of 3-aminopyrazolo[1,5-a]pyridine (0.74 g, 5.55 mmol) and triethylamine (1.0 ml, 6.95 mmol) in EtOAc (15.0 mL) was added cyclopropanecarbonyl chloride (0.63 mL, 6.95 mmol). The resulting mixture was stirred at room temperature for 48 h and diluted with saturated NaHCO$_3$ solution. More EtOAc and H$_2$O were added and separated. The EtOAc solution was concentrated in vacuo to dryness. The residue was recrystalized from EtOAc to give 0.86 g (77%) of light brown solid as the title compound: mp 159–162° C.; IR (diffuse reflectance) 3207, 3085, 3073, 3044, 2998, 1645, 1596, 1477, 1401, 1356, 1330, 1218, 950, 738, 727 cm$^{-1}$; MS (EI) m/z 201 (M$^+$); Anal. Calcd for C$_{11}$H$_{11}$N$_3$O: C, 65.66; H, 5.51; N, 20.88. Found: C, 65.52; H, 5.48; N, 20.82.

Step 2

Preparation of N-ethyl-N-pyrazolo[1,5-a]pyridin-3-ylcyclopropanecarboxamide

To a suspension of NaH (0.23 g, 60% in mineral oil, 5.74 mmol) in THF (15.0 mL) was added a solution of N-pyrazolo[1,5-a]pyridin-3-ylcyclopropanecarboxamide (0.77 g, 3.83 mmol) in THF (5.0 mL) at room temperature, After 15 min, iodoethane (0.52 mL, 6.5 mmol) was added. The resulting mixture was stirred for 16 h and diluted with NH$_4$Cl solution. EtOAc and H$_2$O were added and separated. The aqueous layer was extracted with EtOAc (2×). The combined EtOAc solution was concentrated in vacuo to dryness and the residue was subjected to column chromatography (E:H=1:4). The product was recrystalized from EtOAc/hexane to give 0.61 g (70%) of colorless solid as the title compound: mp 83–86° C.; $^1$H NMR (400 MHz, CDCl$_3$) δ 8.50 (d, J=7.0 Hz, 1H), 7.95 (s, 1H), 7.47 (d, J=8.9 Hz, 1H), 7.26–7.21 (m, 1H), 6.87 (t, J=5.9 Hz, 1H), 3.77 (q, J=7.2 Hz, 2H), 1.40–1.33 (m, 1H), 1.12 (t, J=7.1 Hz, 3H), 1.00–0.96 (m, 2H), 0.59–0.53 (m, 2H); $^{13}$C NMR (100 MHz, CDCl$_3$) δ 174.4, 139.6, 136.7, 129.0, 124.7, 115.9, 114.8, 112.7, 44.4, 31.6, 13.5, 11.9, 8.2; IR (diffuse reflectance) 2970, 1639, 1476, 1444, 1417, 1375, 1340, 1261, 1221, 1111, 1084, 941, 881, 773, 762 cm$^{-1}$; MS (EI) m/z 229 (M$^+$), 230, 229, 161, 160, 146, 133, 118, 105, 78, 69; Anal. Calcd for C$_{13}$H$_{15}$N$_3$O: C, 68.10; H, 6.59; N, 18.33. Found: C, 68.02; H, 6.64; N, 18.28.

Step 3

Preparation of N-(cyclopropylmethyl)-N-ethylpyrazolo[1,5-a]pyridin-3-amine

To a suspension of LiAlH$_4$ (0.70 g, 18.5 mmol) in THF (2.0 mL) was added a solution of N-ethyl-N-pyrazolo[1,5-a]pyridin-3-ylcyclopropanecarboxamide (0.77 g, 3.36 mmol) in THF (5.0 mL) at room temperature and stirred for 16 h. H$_2$O (0.70 mL), 15% NaOH (0.70 mL) and H$_2$O (2.1 mL) were added sequentially. Celite was added and filtered. The filtrate was concentrated in vacuo to dryness and the residue was subjected to column chromatography (E:H=1:4) to give 0.30 g (42%) of yellow oil as the title compound: $^1$H NMR (400 MHz, CDCl$_3$) δ 8.35 (d, J=7.0 Hz, 1H), 7.82 (s, 1H), 7.56 (d, J=9.0 Hz, 1H), 7.02–6.98 (m, 1H), 6.70–6.66 (m, 1H), 3.21 (q, J=7.1 Hz, 2H), 2.92 (d, J=6.6 Hz, 2H), 1.06 (t, J=7.1 Hz, 3H), 0.92–0.88 (m, 1H), 0.46–0.41 (m, 2H), 0.11–0.08 (m, 2H); MS (EI) m/z 216.19 (M$^+$+H).

Step 4

Preparation of N-(cyclopropylmethyl)-N-ethyl-7-iodopyrazolo[1,5-a]pyridin-3-amine Following the general procedure of EXAMPLE 1 (Step 4) and making non-critical variations, the title compound was prepared as a yellow oil (81%): $^1$H NMR (400 MHz, CDCl$_3$) δ 7.95 (s, 1H), 7.62 (d, J=8.8 Hz, 1H), 7.32–7.30 (m, 1H), 6.79 (d, J=7.0 Hz, 1H), 3.22 (q, J=7.1 Hz, 2H), 2.94 (d, J=6.6 Hz, 2H), 1.06 (t, J=7.1 Hz, 3H), 0.92–0.88 (m, 1H), 0.47–0.43 (m, 2H), 0.13–0.11 (m, 2H); MS (EI) m/z 342 (M$^+$+H).

Step 5

Preparation of N-(cyclopropylmethyl)-N-ethyl-7-(2,4-dichlorophenyl)pyrazolo[1,5-a]pyridin-3-amine Following the general procedure of EXAMPLE 1 (Step 5) and making non-critical variations, the title compound was prepared as a yellow oil (86%): $^1$H NMR (400 MHz, CDCl$_3$) δ 7.83 (s, 1H), 7.67 (d, J=8.9 Hz, 1H), 7.61 (s, 1H), 7.50 (d, J=8.2 Hz, 1H), 7.13–7.09 (m, 1H), 6.70 (d, J=6.7 Hz, 1H), 3.24 (q, J=7.1 Hz, 2H), 2.96 (d, J=6.6 Hz, 2H), 1.10 (t, J=7.1 Hz, 3H), 0.90–0.88 (m, 1H), 0.48–0.43 (m, 2H), 0.13–0.09 (m, 2H); MS (EI) m/z 360.17 (M$^+$+H); Anal. Calcd for C$_{19}$H$_{19}$Cl$_2$N$_3$: C, 63.34; H, 5.32; N, 11.66. Found: C, 63.32; H, 5.33; N, 11.58.

Example 4

7-(2,4-dichlorophenyl)-N,N-diethyl-2-methylpyrazolo[1,5-a]pyridin-3-amine

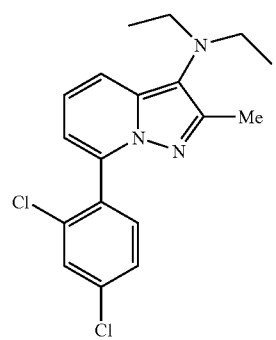

Step 1

Preparation of
2-methyl-3-nitropyrazolo[1,5-a]pyridine

Following the general procedure of EXAMPLE 1 (Step 1) and making non-critical variations, the title compound was prepared as a brownish solid (50%): $^1$H NMR (400 MHz, CDCl$_3$) δ 8.48 (dd, J=5.8, 0.9 Hz, 1H), 8.33 (dd, J=7.9, 1.0 Hz, 1H), 7.67–7.62 (m, 1H), 7.13–7.09 (m, 1H), 2.78 (s, 3H); $^{13}$C NMR (100 MHz, CDCl$_3$) δ 151.8, 137.6, 130.7, 129.2, 123.2, 118.5, 115.4, 14.5; IR (diffuse reflectance) 1528, 1483, 1465, 1443, 1404, 1390, 1363, 1346, 1305, 1259, 1199, 1153, 1137, 770, 751 cm$^{-1}$; MS (EI) m/z 177 (M$^+$); HRMS (FAB) calcd for C$_8$H$_7$N$_3$O$_2$+H 178.0616. found 178.0607. Anal. Calcd for C$_8$H$_7$N$_3$O$_2$: C, 54.24; H, 3.98; N, 23.72. Found: C, 54.02; H, 3.89; N, 23.70.

Step 2

Preparation of
2-methylpyrazolo[1,5-a]pyridin-3-amine

Following the general procedure of EXAMPLE 1 (Step 2) and making non-critical variations, the title compound was prepared as a brown solid (99%): $^1$H NMR (400 MHz, CDCl$_3$) δ 8.24 (d, J=7.0 Hz, 1H), 7.34 (d, J=8.9 Hz, 1H), 6.96 (t, J=7.0 Hz, 1H), 6.58 (t, J=6.4 Hz, 1H), 2.85 (br, 2H), 2.46 (s, 3H); HRMS (FAB) calcd for C$_8$H$_9$N$_3$+H 148.0875. found 148.0873.

Step 3

Preparation of
N,N-diethyl-2-methylpyrazolo[1,5-a]pyridin-3-amine

Following the general procedure of EXAMPLE 1 (Step 3) and making non-critical variations, the title compound was prepared as a yellow oil (41%): $^1$H NMR (400 MHz, CDCl$_3$) δ 8.29 (d, J=7.0 Hz, 1H), 7.46 (d, J=8.9 Hz, 1H), 7.01–6.98 (m, 1H), 6.62 (t, J=6.8 Hz, 1H), 3.14 (q, J=7.1 Hz, 4H), 2.45 (s, 3H), 1.00 (t, J=7.1 Hz, 6H); MS (EI) m/z 204.22 (M$^+$+H).

Step 4

Preparation of N,N-diethyl-7-iodo-2-methylpyrazolo[1,5-a]pyridin-3-amine

Following the general procedure of EXAMPLE 1 (Step 4) and making non-critical variations, the title compound was prepared as a light yellow solid (67%): $^1$H NMR (400 MHz, CDCl$_3$) δ 7.49 (d, J=8.8 Hz, 1H), 7.23 (d, J=7.0 Hz, 1H), 6.75 (dd, J=8.8, 7.0 Hz, 1H), 3.14 (q, J=7.1 Hz, 4H), 2.51 (s, 3H), 0.97 (t, J=7.1 Hz, 6H); MS (EI) m/z 330.20 (M$^+$+H).

Step 5

Preparation of 7-(2,4-dichlorophenyl)-N,N-diethyl-2-methylpyrazolo[1,5-a]pyridin-3-amine Following the general procedure of EXAMPLE 1 (Step 5) and making non-critical variations, the title compound was prepared as a brown solid (41%): $^1$H NMR (400 MHz, CDCl$_3$) δ 7.59 (d, J=2.0 Hz, 1H), 7.56–7.52 (m, 2H), 7.42 (dd, J=8.3, 2.1 Hz, 1H), 7.09–7.05 (m, 1H), 6.61 (d, J=6.8 Hz, 1H), 3.17 (q, J=7.1 Hz, 4H), 2.40 (s, 3H), 1.01 (t, J=7.1 Hz, 6H); MS (EI) m/z 348 (M$^+$+H).

Example 5

7-(2,4-dichlorophenyl)-2-methyl-N,N-dipropylpyrazolo[1,5-a]pyridin-3-amine

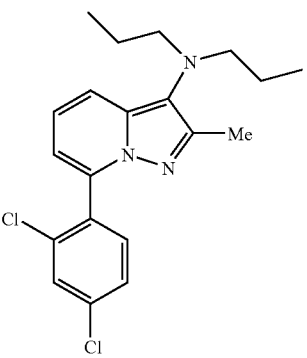

Step 1

Preparation of 2-methyl-N,N-dipropylpyrazolo[1,5-a]pyridin-3-amine

Following the general procedure of EXAMPLE 1 (Step 3) and making non-critical variations, the title compound was prepared as a brown oil (9.5%): $^1$H NMR (400 MHz, CDCl$_3$) δ 8.28 (d, J=7.0 Hz, 1H), 7.46 (d, J=8.9 Hz, 1H), 7.01–6.97 (m, 1H), 6.61 (t, J=6.8 Hz, 1H), 3.03 (t, J=7.2 Hz, 4H), 2.45 (s, 3H), 1.44–1.35 (m, 4H), 0.90 (t, J=7.3 Hz, 6H); MS (EI) m/z 232.28 (M$^+$+H).

Step 2

Preparation of 7-iodo-2-methyl-N,N-dipropylpyrazolo[1,5-a]pyridin-3-amine

Following the general procedure of EXAMPLE 1 (Step 4) and making non-critical variations, the title compound was prepared as a yellow oil (67%): $^1$H NMR (400 MHz, CDCl$_3$) δ 7.49 (d, J=8.8 Hz, 1H), 7.22 (d, J=7.0 Hz, 1H), 6.77–6.73 (m, 1H), 3.03 (t, J=7.2 Hz, 4H), 2.52 (s, 3H), 1.43–1.33 (m, 4H), 0.89 (t, J=7.3 Hz, 6H); HRMS (FAB) calcd for C$_{14}$H$_{20}$IN$_3$+H 358.0782. found 358.0763.

Step 3

Preparation of 7-(2,4-dichlorophenyl)-2-methyl-N,N-dipropylpyrazolo[1,5-a]pyridin-3-amine Following the general procedure of EXAMPLE 1 (Step 5) and making non-critical variations, the title compound was prepared as a yellow oil (78%): $^1$H NMR (400 MHz, CDCl$_3$) δ 7.59 (d, J=2.0 Hz, 1H), 7.56–7.52 (m, 2H), 7.41 (dd, J=8.2, 2.0 Hz, 1H), 7.09–7.04 (m, 1H), 6.60 (dd, J=6.8, 1.3 Hz, 1H), 3.05 (t, J=7.3 Hz, 4H), 2.40 (s, 3H), 1.47–1.37 (m, 4H), 0.92 (t, J=7.3 Hz, 6H); HRMS (FAB) calcd for C$_{20}$H$_{23}$Cl$_2$N$_3$+H 376.1347. found 376.1362.

Example 6

7-(2,4-dichlorophenyl)-N,N,2-triethylpyrazolo[1,5-a]pyridin-3-amine

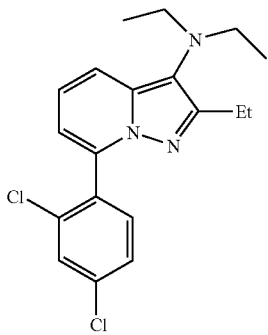

Step 1

Preparation of 2-ethyl-3-nitropyrazolo[1,5-a]pyridine

Following the general procedure of EXAMPLE 1 (Step 1) and making non-critical variations, the title compound was prepared as a light brown solid (78%): mp 118–121° C. (hexanes/CH$_2$Cl$_2$); $^1$H NMR (400 MHz, CDCl$_3$) δ 8.54 (d, J=6.8 Hz, 1H), 8.40 (d, J=7.8 Hz, 1H), 7.71–7.66 (m, 1H), 7.17–7.13 (m, 1H), 3.28 (q, J=7.5 Hz, 2H), 1.46–1.43 (t, J=7.5 Hz, 3H); MS (FAB) m/z 191 (M$^+$); Anal. Calcd for C$_9$H$_9$N$_3$O$_2$: C, 56.54; H, 4.74; N, 21.98. Found: C, 56.63; H, 4.76; N, 22.10.

Step 2

Preparation of 2-ethylpyrazolo[1,5-a]pyridin-3-amine

Following the general procedure of EXAMPLE 1 (Step 2) and making non-critical variations, the title compound was prepared as a light brown oil (99%): $^1$H NMR (400 MHz, CDCl$_3$) δ 8.24 (d, J=7.0 Hz, 1H), 7.32 (d, J=8.9 Hz, 1H), 6.95–6.91 (m, 1H), 6.57–6.54 (m, 1H), 2.87 (br, 2H), 2.83 (q, J=7.6 Hz, 2H), 1.38 (t, J=7.6 Hz, 3H); MS (EI) m/z 162 (M$^+$+H).

Step 3

Preparation of N,N,2-triethylpyrazolo[1,5-a]pyridin-3-amine

Following the general procedure of EXAMPLE 1 (Step 3) and making non-critical variations, the title compound was prepared as a light yellow oil (86%): $^1$H NMR (400 MHz, CDCl$_3$) δ 8.33 (d, J=7.0 Hz, 1H), 7.47 (d, J=8.9 Hz, 1H), 6.98 (dd, J=7.0, 8.9 Hz, 1H), 6.62 (dd, J=7.0, 7.0 Hz, 1H), 3.14 (q, J=7.2 Hz, 4H), 2.84 (q, J=7.6 Hz, 2H), 1.42 (t, J=7.6 Hz, 3H), 0.99 (t, J=7.2 Hz, 6H); $^{13}$C NMR (100 MHz, CDCl$_3$) δ 155.6, 137.6, 129.1, 122.2, 118.9, 117.3, 110.7, 50.3, 20.1, 14.4, 14.2; IR (diffuse reflectance) 3079, 3035, 2970, 2933, 2897, 2870, 2817, 1630, 1533, 1530, 1495, 1445, 1379, 1368, 1347, 759, 735 cm$^{-1}$; MS (EI) m/z 218 (M$^+$+H); HRMS (FAB) calcd for C$_{13}$H$_{19}$N$_3$+H 218.1657. found 218.1664.

Step 4

Preparation of N,N,2-triethyl-7-iodopyrazolo[1,5-a]pyridin-3-amine

Following the general procedure of EXAMPLE 1 (Step 4) and making non-critical variations, the title compound was prepared as a light yellow solid (62%): $^1$H NMR (400 MHz, CDCl$_3$) δ 7.49 (d, J=8.8 Hz, 1H), 7.22 (d, J=7.0 Hz, 1H), 6.73 (dd, J=7.0, 8.8 Hz, 1H), 3.14 (q, J=7.1 Hz, 4H), 2.90 (q, J=7.6 Hz, 2H), 1.39 (t, J=7.6 Hz, 3H), 2.90 (q, J=7.1 Hz, 6H); $^{13}$C NMR (100 MHz, CDCl$_3$) δ 155.7, 138.5, 122.7, 122.6, 121.2, 117.1, 93.3, 50.2, 20.4, 14.4; MS (EI) m/z 344 (M$^+$+H).

Step 5

Preparation of 7-(2,4-dichlorophenyl)-N,N,2-triethylpyrazolo[1,5-a]pyridin-3-amine Following the general procedure of EXAMPLE 1 (Step 5) and making non-critical variations, the title compound was prepared as a light yellow oil (79%): $^1$H NMR (400 MHz, CDCl$_3$) δ 7.59 (d, J=2.0 Hz, 1H), 7.56–7.53 (m, 2H), 7.41 (dd, J=2.0, 8.3 Hz, 1H), 7.06 (dd, J=6.9, 8.9 Hz, 1H), 6.61 (dd, J=1.3, 6.8 Hz, 1H), 3.17 (q, J=7.1 Hz, 4H), 2.79 (q, J=7.6 Hz, 2H), 1.28 (t, J=7.6 Hz, 3H), 1.02 (t, J=7.1 Hz, 6H); $^{13}$C NMR (100 MHz, CDCl$_3$) δ 155.5, 138.0, 136.9, 136.0, 135.6, 132.9, 132.2, 130.3, 127.5, 121.4, 119.5, 117.2, 112.7, 50.3, 20.2, 14.7, 14.4; IR (diffuse reflectance) 2969, 2933, 2877, 2870, 2815, 1629, 1590, 1552, 1524, 1501, 1491, 1473, 1457, 817, 781, 725 cm$^{-1}$; MS (EI) m/z 362 (M$^+$+H), 364 (M$^+$+H); HRMS (FAB) calcd for C$_{19}$H$_{21}$Cl$_2$N$_3$+H 362.1190. found 362.1192.

Example 7

7-(2-Methyl-4-chlorophenyl)-N,N,2-triethylpyrazolo[1,5-a]pyridin-3-amine

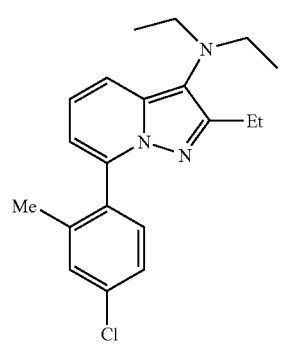

Following the general procedure of EXAMPLE 1 (Step 5) and making non-critical variations, the title compound was prepared as a light yellow oil (60%): $^1$H NMR (400 MHz, CDCl$_3$) δ 7.54 (dd, J=1.3, 8.9 Hz, 1H), 7.39–7.30 (m, 3H), 7.41 (dd, J=6.8, 8.9 Hz, 1H), 6.53 (dd, J=1.3, 8.9 Hz, 1H), 3.18 (q, J=7.1 Hz, 4H), 2.80 (q, J=7.6 Hz, 2H), 2.13 (s, 3H), 1.28 (t, J=7.6 Hz, 3H), 1.02 (t, J=7.1 Hz, 6H); $^{13}$C NMR (100 MHz, CDCl$_3$) δ 155.6, 140.5, 139.9, 138.0, 135.3, 133.0, 131.7, 130.5, 126.4, 121.7, 119.3, 116.5, 112.1, 50.3, 20.2, 20.0, 14.7, 14.4; IR (diffuse reflectance) 2969, 2932, 2897, 2870, 2816, 1627, 1596, 1566, 1551, 1524, 1500, 1451, 1446, 1395, 1375, 1340, 1065, 818, 782 cm$^{-1}$; MS (EI) m/z 342 (M$^+$+H), 344 (M$^+$+H); HRMS (FAB) calcd for C$_{20}$H$_{24}$ClN$_3$+H 342.1737. found 342.1728.

Example 8

7-(2-Chloro-4-trifluoromethylphenyl)-N,N,2-triethylpyrazolo[1.5-a]pyridin-3-amine

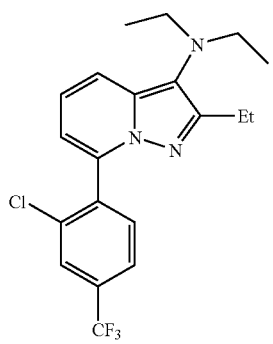

Following the general procedure of EXAMPLE 1 (Step 5) and making non-critical variations, the title compound was prepared as a light yellow oil (45%): $^1$H NMR (400 MHz, CDCl$_3$) δ 7.73 (s, 1H), 7.63 (d, J=8.0 Hz, 1H), 7.57 (d, J=8.0 Hz, 1H), 7.46 (dd, J=1.2, 8.9 Hz, 1H), 6.97 (dd, J=6.8, 8.9 Hz, 1H), 6.52 (dd, J=1.2, 6.8 Hz, 1H), 3.07 (q, J=7.1 Hz, 4H), 2.67 (q, J=7.6 Hz, 2H), 1.16 (t, J=7.6 Hz, 3H), 0.91 (t, J=7.1 Hz, 6H); $^{13}$C NMR (100 MHz, CDCl$_3$) δ 155.6, 137.9, 137.2, 136.6, 135.5, 132.9, 130.0, 127.5, 127.4, 125.0, 124.1, 121.4, 119.7, 117.6, 112.8, 50.3, 20.2, 14.7, 14.5; IR (diffuse reflectance) 2971, 2934, 2899, 2872, 2817, 2783, 1631, 1614, 1554, 1526, 1504, 1489, 1475, 1447, 1324, 1174, 1134, 832, 781, 712 cm$^{-1}$; MS (EI) m/z 396 (M$^+$+H), 398 (M$^+$+H); HRMS (FAB) calcd for C$_{20}$H$_{21}$ClF$_3$N$_3$+H 396.1454. found 396.1447.

Example 9

7-(2,4,6-Trimethylphenyl)-N,N,2-triethylpyrazolo[1,5-a]pyridin-3-amine

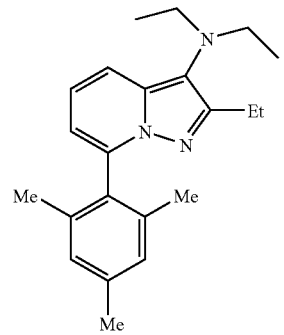

A mixture of 3-diethylamino-7-iodopyrazolo[1,5-a]pyridine (0.074 g, 0.217 mmol), 2,4,6-trimethylphenylboronic acid (0.053 g, 0.325 mmol), potassium phosphate (0.138 g, 0.650 mmol), dicyclohexyl[2-(9-phenanthryl)phenyl]phosphine (0.012 g, 0.026 mmol) and Pd$_2$(dba)$_3$ (0.004 g, 0.004 mmol) in toluene (2.2 mL) was refluxed for 72 h. Additional Pd$_2$(dba)$_3$ (0.004 g, 0.004 mmol) and 2,4,6-trimethylphenylboronic acid (0.053 g, 0.325 mmol) were added and reflux was continued for 42 h. The reaction mixture was diluted with CH$_2$Cl$_2$ and filtered through a bed of celite. The filtrate was concentrated in vacuo to dryness. The residue was subjected to preparative thin layer chromatography (5% ethyl acetate/hexane) to give 0.048 g (66%) of a light yellow oil as the title compound: $^1$H NMR (400 MHz, CDCl$_3$) δ 7.37 (d, J=8.9 Hz, 1H), 6.95–6.90 (m, 3H), 6.35 (d, J=6.7 Hz, 1H), 3.07 (q, J=7.1 Hz, 4H), 2.66 (q, J=7.6 Hz, 2H), 2.28 (s, 3H), 1.92 (s, 6H), 1.10 (t, J=7.6 Hz, 3H), 0.90 (t, J=7.1 Hz, 6H); $^{13}$C NMR (100 MHz, CDCl$_3$) δ 155.6, 137.9, 137.2, 136.6, 135.5, 132.9, 130.0, 127.5, 127.4, 125.0, 124.1, 121.4, 119.7, 117.6, 112.8, 50.3, 20.2, 14.7, 14.5; IR (diffuse reflectance) 2969, 2931, 2898, 2869, 2815, 1627, 1613, 1552, 1524, 1498, 1475, 1456, 1445, 1339, 1306, 1228, 1217, 848, 782 cm$^{-1}$; MS (EI) m/z 336 (M$^+$+H); HRMS (FAB) calcd for C$_{22}$H$_{29}$N$_3$+H 336.2440. found 336.2421.

Example 10

7-(2,4-Dichlorophenyl)-2-ethyl-N,N-dipropylpyrazolo[1,5-a]pyridin-3-amine

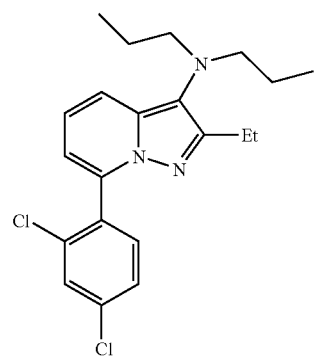

Step 1

Preparation of
2-Ethyl-N,N-dipropylpyrazolo[1,5-a]pyridin-3-amine

Following the general procedure of EXAMPLE 1 (Step 3) and making non-critical variations, the title compound was prepared as a yellow oil (58%): $^1$H NMR (400 MHz, CDCl$_3$) δ 8.30 (d, J=7.0 Hz, 1H), 7.45 (d, J=8.9 Hz, 1H), 6.98–6.94 (m, 1H), 6.61–6.58 (m, 1H), 3.02 (t, J=7.4 Hz, 4H), 2.84 (q, J=7.6 Hz, 2H), 1.44–1.35 (m, 7H), 0.89 (t, J=7.4 Hz, 6H); MS (EI) m/z 246 (M$^+$+H).

Step 2

Preparation of 2-Ethyl-7-iodo-N,N-dipropylpyrazolo[1,5-a]pyridin-3-amine

Following the general procedure of EXAMPLE 1 (Step 4) and making non-critical variations, the title compound was prepared as a light yellow oil (62%): $^1$H NMR (400 MHz, CDCl$_3$) δ 7.48 (d, J=8.8 Hz, 1H), 7.21 (d, J=7.0 Hz, 1H), 6.75–6.71 (m, 1H), 3.03 (t, J=7.3 Hz, 4H), 2.90 (q, J=7.6 Hz, 2H), 1.45–1.36 (m, 7H), 0.89 (t, J=7.3 Hz, 6H); $^{13}$C NMR (100 MHz, CDCl$_3$) δ 155.6, 138.8, 123.2, 123.0, 122.9, 117.5, 93.6, 58.9, 22.7, 20.8, 14.8, 12.5; HRMS (FAB) calcd for C$_{15}$H$_{22}$IN$_3$+H 372.0938. found 372.0930.

Step 3

Preparation of 7-(2,4-dichlorophenyl)-2-ethyl-N,N-dipropylpyrazolo[1,5-a]pyridin-3-amine Following the general procedure of EXAMPLE 1 (Step 5) and making non-critical variations, the title compound was prepared as a light yellow oil (75%): $^1$H NMR (400 MHz, CDCl$_3$) δ 7.59 (d, J=2.0 Hz, 1H), 7.57–7.51 (m, 2H), 7.43 (dd, J=8.2, 2.0 Hz, 1H), 7.03–6.99 (m, 1H), 6.58 (d, J=6.6 Hz, 1H), 3.02 (t, J=7.3 Hz, 4H), 2.75 (q, J=7.2 Hz, 2H), 1.42–1.37 (m, 4H), 1.23 (t, J=7.5 Hz, 3H), 0.88 (t, J=7.3 Hz, 6H); $^{13}$C NMR (100 MHz, CDCl$_3$) δ 154.6, 137.5, 136.4, 135.6, 135.2, 132.6, 131.8, 129.9, 127.1, 120.9, 120.8, 116.8, 112.3, 58.2, 22.1, 19.9, 14.2, 11.7; HRMS (FAB) calcd for C$_{21}$H$_{25}$Cl$_2$N$_3$+H 390.1504. found 390.1511.

Example 11

7-(2,4-Dichlorophenyl)-2-ethyl-N,N-dipropylpyrazolo[1,5-a]pyridin-3-amine maleic acid salt

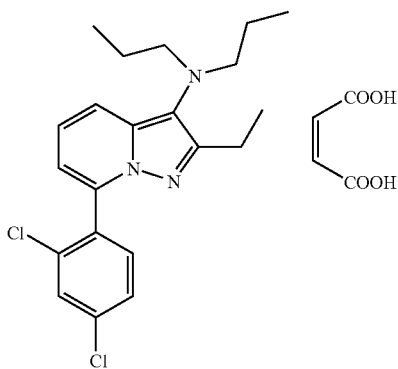

A solution of 7-(2,4-dichlorophenyl)-2-ethyl-N,N-dipropylpyrazolo[1,5-a]pyridin-3-amine (530 mg, 1.4 mmol) in ethyl acetate (20 mL) was treated with maleic acid (169 mg, 1.4 mmol) dissolved in CH$_3$OH (1.5 mL). The solution was stirred at room temperature for 1.5 hours then concentrated in vacuo to give a yellow oil. Trituration with Et$_2$O and hexane gave 560 mg (81%) of a brown solid as the title compound: mp 106–112° C.; $^1$H NMR (400 MHz, DMSO-d$_6$) δ 7.82 (d, J=1.9 Hz, 1H), 7.68–7.57 (m, 3H), 7.20–7.16 (m, 1H), 6.78 (d, J=6.4 Hz, 1H), 6.26 (s, 1H), 3.03 (t, J=7.0 Hz, 4H), 2.65 (q, J=7.5 Hz, 2H), 1.36–1.27 (m, 4H), 1.13 (t, J=7.5 Hz, 3H), 0.85 (t, J=7.3 Hz, 6H); $^{13}$C NMR (100 MHz, DMSO-d$_6$) δ 166.6, 153.2, 136.3, 135.9, 134.6, 134.4, 133.2, 131.8, 130.5, 128.9, 127.4, 121.9, 116.6, 112.5, 57.4, 21.2, 19.0, 13.9, 11.4; IR (diffuse reflectance) 2975, 2965, 2940, 2491, 2353, 2335, 1983, 1948, 1586, 1552, 1547, 1485, 1470, 1455, 1354 cm$^{-1}$; HRMS (FAB) calcd for C$_{21}$H$_{25}$Cl$_2$N$_3$+H 390.1504. found 390.1501; Anal. Calcd for C$_{21}$H$_{25}$Cl$_2$N$_3$·C$_4$H$_4$O$_4$: C, 59.29; H, 5.77; N, 8.30. Found: C, 59.40; H, 5.78; N, 8.14.

Example 12

2-Ethyl-7-(4-methoxy-2-methylphenyl)-N,N-dipropylpyrazolo[1,5-a]pyridin-3-amine

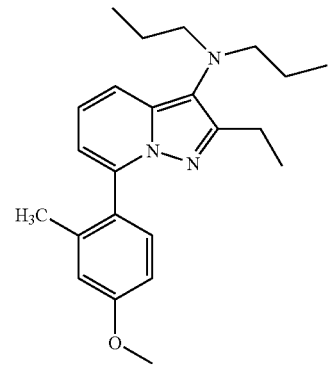

Following the general procedure of EXAMPLE 1 (Step 5) and making non-critical variations, the title compound was prepared as a light yellow solid (48%): mp 76.0–79.0° C.; $^1$H NMR (400 MHz, Acetone-d$_6$) δ 7.49 (d, J=8.8 Hz, 1H), 7.36 (d, J=8.3 Hz, 1H), 7.06–7.02 (m, 1H), 6.90 (d, J=2.5 Hz, 1H), 6.89 (dd, J=8.3, 2.5 Hz, 1H), 6.54 (d, J=6.7 Hz, 1H), 3.90 (s, 3H), 3.06 (t, J=7.3 Hz, 4H), 2.79 (q, J=7.6 Hz, 2H), 2.14 (s, 3H), 1.48–1.39 (m, 4H), 1.27 (t, J=7.5 Hz, 3H), 0.92 (t, J=7.5 Hz, 3H); IR (diffuse reflectance) 2960, 2931, 2871, 2426, 2353, 2160, 2067, 1603, 1492, 1466, 1313, 1240, 1036, 786 cm$^{-1}$; HRMS (FAB) calcd for C$_{23}$H$_{31}$N$_3$O+H 366.2545. found 366.2551; Anal. Calcd for C$_{23}$H$_{31}$N$_3$O·0.1H$_2$O: C, 75.21; H, 8.56; N, 11.44. Found: C, 75.24; H, 8.55; N, 11.31.

Example 13

7-(2-Chloro-4-methoxyphenyl)-2-ethyl-N,N-dipropylpyrazolo[1,5-a]pyridin-3-amine

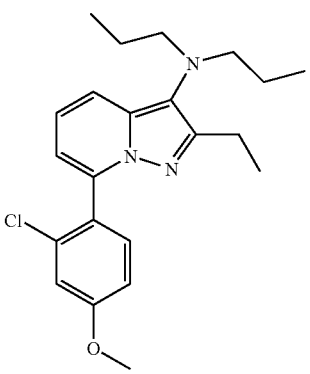

Following the general procedure of EXAMPLE 1 (Step 5) and making non-critical variations, the title compound was prepared as a light yellow solid (70%): mp 73.6–76.0° C.; $^1$H NMR (400 MHz, CDCl$_3$) δ 7.53 (m, 2H), 7.11 (d, J=2.5 Hz, 1H), 7.06–7.04 (m, 1H), 6.98 (dd, J=8.6, 2.5 Hz, 1H), 6.62 (d, J=6.8 Hz, 1H), 3.91 (s, 3H), 3.06 (t, J=7.4 Hz, 4H), 2.80 (q, J=7.5 Hz, 2H), 1.49–1.39 (m, 4H), 1.28 (t, J=7.5 Hz, 3H), 0.92 (t, J=7.3 Hz, 6H); IR (diffuse reflectance) 2961, 2931, 2478, 2350, 2340, 2286, 2176, 1601, 1490, 1301, 1282, 1232, 1029, 844, 785 cm$^{-1}$; HRMS (FAB) calcd for C$_{22}$H$_{28}$ClN$_3$O+H 386.1999. found 386.2011; Anal. Calcd for C$_{22}$H$_{28}$ClN$_3$O: C, 68.47; H, 7.31; N, 10.89. Found: C, 68.51; H, 7.35; N, 10.75.

Example 14

7-[4-(Dimethylamino)-2-(trifluoromethyl)phenyl]-2-ethyl-N,N-dipropylpyrazolo[1,5-a]pyridin-3-amine

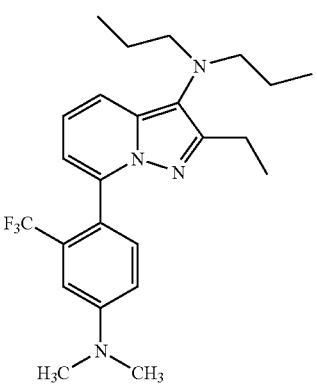

Following the general procedure of EXAMPLE 1 (Step 5) and making non-critical variations, the title compound was prepared as a light yellow solid (70%): mp 69.1–79.8° C.; $^1$H NMR (400 MHz, CDCl$_3$) δ 7.50 (d, J=8.8 Hz, 1H), 7.44 (d, J=8.6 Hz, 1H), 7.09 (d, J=2.6 Hz, 1H), 7.05–7.01 (m, 1H), 6.98 (dd, J=8.6, 2.6 Hz, 1H), 6.57 (d, J=5.9 Hz, 1H), 3.11–3.06 (m, 1.0H), 2.80 (q, J=7.3 Hz, 2H), 1.45 (m, 4H), 1.27 (t, J=7.6 Hz, 3H), 0.94 (t, J=7.3 Hz, 6H); IR (diffuse reflectance) 2958, 2933, 2873, 2473, 2350, 1912, 1616, 1520, 1376, 1298, 1239, 1184, 1166, 1125, 1105 cm$^{-1}$; HRMS (FAB) calcd for C$_{24}$H$_{31}$F$_3$N$_4$+H 433.2579. found 433.2575; Anal. Calcd for C$_{24}$H$_{31}$F$_3$N$_4$: C, 66.65; H, 7.22; N, 12.95. Found: C, 66.29; H, 7.18; N, 12.7.

Eaxmple 15

2-Ethyl-7-(2-methoxy-4,6-dimethylphenyl)-N,N-dipropylpyrazolo[1,5-a]pyridin-3-amine

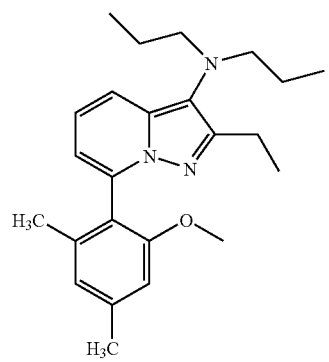

Following the general procedure of EXAMPLE 9 and making non-critical variations, the title compound was prepared as a light yellow solid (4%): mp 72.3–74.6° C.; $^1$H NMR (400 MHz, CDCl$_3$) δ 7.48 (d, J=8.8 Hz, 1H), 7.06–7.02 (m, 1H), 6.81 (s, 1H), 6.73 (s, 1H), 6.55 (d, J=6.7 Hz, 1H), 3.73 (s, 3H), 3.06 (t, J=7.3 Hz, 4H), 2.77 (q, J=7.5 Hz, 2H), 2.43 (s, 3H), 2.02 (s, 3H), 1.48–1.39 (m, 4H), 1.23 (t, J=7.5 Hz, 3H), 0.92 (t, J=7.3 Hz, 6H); $^{13}$C NMR (100 MHz, CDCl$_3$) δ 158.0, 154.7, 140.3, 139.5, 137.9, 137.0, 123.7, 121.5, 120.7, 120.4, 115.8, 112.9, 110.3, 58.7, 56.3, 22.5, 22.2, 20.1, 19.8, 15.0, 12.2; HRMS (FAB) calcd for C$_{24}$H$_{33}$N$_3$O+H 380.2702. found 380.2712; Anal. Calcd for C$_{24}$H$_{33}$N$_3$O: C, 75.95; H, 8.76; N, 11.07. Found: C, 75.79; H, 8.72; N, 10.91.

Example 16

7-[2-Chloro-4-(dimethylamino)phenyl]-2-ethyl-N,N-dipropylpyrazolo[1,5-a]pyridin-3-amine Following the general procedure of EXAMPLE 1 (Step 5) and making non-critical

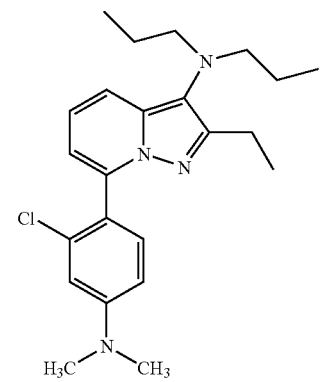

variations, the title compound was prepared as a light yellow solid (44%): mp 132.8–134.3° C.; $^1$H NMR (400 MHz, CDCl$_3$) δ 7.50–7.46 (m, 2H), 7.05–7.01 (m, 1H), 6.85 (d, J=2.6 Hz, 1H), 6.74 (dd, J=8.7, 2.6 Hz, 1H), 6.63 (d, J=6.8 Hz, 1H), 3.07–3.04 (m, 10H), 2.80 (q, J=7.6 Hz, 2H), 1.49–1.39 (m, 4H), 1.29 (t, J=7.5 Hz, 3H), 0.92 (t, J=7.3 Hz, 6H); IR (diffuse reflectance) 2958, 2933, 2872, 2470, 2350, 2341, 2193, 2054, 1607, 1520, 1447, 1372, 1311, 810, 781 cm$^{-1}$; HRMS (FAB) calcd for C$_{23}$H$_{31}$ClN$_4$+H 399.2315. found 399.2314; Anal. Calcd for C$_{23}$H$_{31}$ClN$_4$: C, 69.24; H, 7.83; N, 14.04. Found: C, 69.17; H, 7.96; N, 14.01.

Example 17

7-(2,4-Dimethoxyphenyl)-2-ethyl-N,N-diproylpyrazolo[1,5-a]pyridin-3-amine

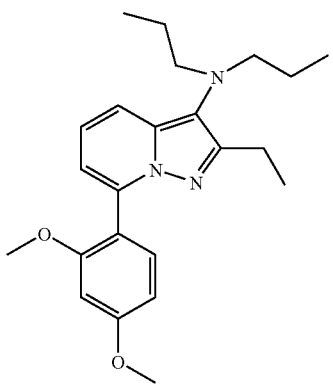

Following the general procedure of EXAMPLE 1 (Step 5) and making non-critical variations, the title compound was prepared as a yellow oil (36%): $^1$H NMR (400 MHz, CDCl$_3$) δ 7.53 (d, J=9.0 Hz, 1H), 7.46 (dd, J=8.8, 1.3 Hz, 1H), 7.04–7.00 (m, 1H), 6.66–6.64 (m, 3H), 3.91 (s, 3H), 3.80 (s, 3H), 3.06 (t, J=7.3 Hz, 4H), 2.79 (q, J=7.6 Hz, 2H), 1.48–1.39 (m, 4H), 1.28 (t, J=7.6 Hz, 3H), 0.91 (t, J=7.3 Hz, 6H); HRMS (FAB) calcd for C$_{23}$H$_{31}$N$_3$O$_2$+H 382.2494. found 382.2483.

Example 18

7-[6-(Dimethylamino)-4-methylpyridin-3-yl]-2-ethyl-N,N-dipropylpyrazolo[1,5-a]pyridin-3-amine

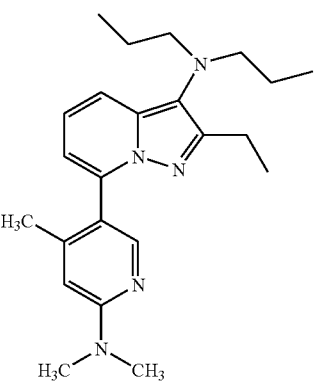

Following the general procedure of EXAMPLE 1 (Step 5) and making non-critical variations, the title compound was prepared as a light yellow solid (58%): mp 98.5–100.3° C.; $^1$H NMR (400 MHz, CDCl$_3$) δ 8.21 (s, 1H), 7.49 (d, J=8.6 Hz, 1H), 7.06–7.02 (m, 1H), 6.57 (d, J=6.4 Hz, 1H), 6.51 (s, 1H), 3.19 (s, 6H), 3.06 (t, J=7.1 Hz, 4H), 2.80 (q, J=7.5 Hz, 2H), 2.13 (s, 3H), 1.46–1.40 (m, 4H), 1.29 (t, J=7.5 Hz, 3H), 0.92 (t, J=7.3 Hz, 6H); IR (diffuse reflectance) 2965, 2953, 2931, 2926, 2869, 2459, 2426, 2350, 2341, 2297, 1607, 1524, 1500, 1404, 1340 cm$^{-1}$; HRMS (FAB) calcd for C$_{23}$H$_{33}$N$_5$+H 380.2814. found 380.2810; Anal. Calcd for C$_{23}$H$_{33}$N$_5$: C, 72.78; H, 8.76; N, 18.45. Found: C, 72.96; H, 8.87; N, 18.52.

Example 19

7-(2-Chloro-4-methoxyphenyl)-2-ethyl-N-(3-fluoropropyl)-N-(2-methoxyethyl)pyrazolo[1,5-a]pyridin-3-amine

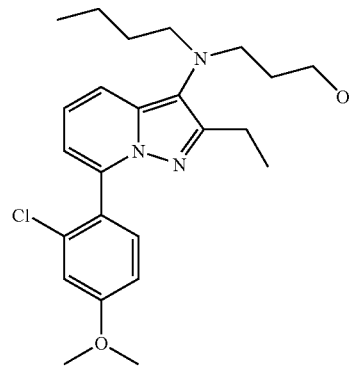

Step 1

Preparation of N-(2-ethylpyrazolo[1,5-a]pyridin-3-yl)-2-methoxyacetamide

Following the general procedure of EXAMPLE 3 (Step 1) and making non-critical variations, the title compound was prepared as a white solid (100%): mp 106.1–107.6° C.; $^1$H NMR (400 MHz, DMSO-d$_6$) δ 69.35 (s, 1H), 8.51 (d, J=6.8 Hz, 1H), 7.30 (d, J=8.7 Hz, 1H), 7.15–7.11 (m, 1H), 6.80–6.76 (m, 1H), 4.05 (s, 2H), 3.42 (s, 3H), 2.64 (q, J=7.6 Hz, 2H), 1.21 (t, J=7.6 Hz, 3H); $^{13}$C NMR (100 MHz, DMSO-d$_6$) δ 168.8, 151.5, 135.4, 128.3, 122.8, 116.1, 111.0, 105.9, 71.5, 58.6, 19.0, 12.8; IR (diffuse reflectance) 3236, 3222, 2434, 2089, 1950, 1660, 1638, 1566, 1529, 1485, 1364, 1199, 1128, 974, 756 cm$^{-1}$; HRMS (FAB) calcd for C$_{12}$H$_{15}$N$_3$O$_2$+H 234.1242. found 234.1236; Anal. Calcd for C$_{12}$H$_{15}$N$_3$O$_2$: C, 61.79; H, 6.48; N, 18.01. Found: C, 61.78; H, 6.63; N, 17.98.

Step 2

Preparation of N-(2-ethylpyrazolo[1,5-a]pyridin-3-yl)-N-(3-fluoropropyl)-2-methoxyacetamide Following the general procedure of EXAMPLE 3 (Step 2) and making non-critical variations, the title compound was prepared as a light yellow solid (50%): mp 59.9–63.9° C.; $^1$H NMR (400 MHz, DMSO-$d_6$) δ 8.64 (d, J=7.0 Hz, 1H), 7.53 (d, J=8.9 Hz, 1H), 7.32–7.28 (m, 1H), 6.93–6.90 (m, 1H), 4.52 (dt, J=47.3, 5.3 Hz, 2H), 4.02–3.95 (m, 1H), 3.62 (d, J=15.2 Hz, 1H), 3.58 (d, J=15.2 Hz, 1H), 3.54–3.35 (m, 1H), 3.16 (s, 3H), 2.72–2.62 (m, 2H), 1.91–1.68 (m, 2H), 1.28 (t, J=7.6 Hz, 3H); $^{13}$C NMR (100 MHz, DMSO-$d_6$) δ 169.6, 152.4, 136.4, 129.0, 125.2, 114.7, 112.2, 109.0, 82.6 (d, J=161.6 Hz), 69.3, 58.2, 45.1 (d, J=5.5 Hz), 28.7 (d, J=19.3 Hz), 18.4, 12.4; $^{19}$F NMR (376 MHz, DMSO-$d_6$) −219.0 (m); IR (diffuse reflectance) 2970, 2486, 2420, 2350, 2338, 2262, 1676, 1498, 1452, 1193, 1129, 948, 930, 758, 743 cm$^{-1}$; HRMS (FAB) calcd for $C_{15}H_{20}FN_3O_2$+H 294.1618. found 294.1605; Anal. Calcd for $C_{15}H_{20}FN_3O_2$: C, 61.42; H, 6.87; N, 14.32. Found: C, 61.42; H, 6.94; N, 14.29.

Step 3

Preparation of 2-ethyl-N-(3-fluoropropyl)-N-(2-methoxyethyl)pyrazolo[1,5-a]pyridin-3-amine A 0° C. solution of N-(2-ethylpyrazolo[1,5-a]pyridin-3-yl)-N-(3-fluoropropyl)-2-methoxyacetamide (1.62 g, 5.5 mmol) in THF (25 mL) was treated with borane dimethyl sulfide complex (1.1 mL, 11.0 mmol). The reaction was stirred at room temperature for 5.5 hours. The reaction was quenched with 2N HCl then made basic with 4N NaOH. The mixture was extracted twice with ethyl acetate. The combined organic layers was washed with brine, dried over MgSO$_4$ and concentrated in vacuo to give a yellow oil which was subjected to column chromatography (40% ethyl acetate/hexane) to give 0.313 g (20%) of yellow oil as the title compound: $^1$H NMR (400 MHz, CDCl$_3$) δ 8.99 (d, J=7.2 Hz, 1H), 7.68 (d, J=8.8 Hz, 1H), 7.41–7.37 (m, 1H), 7.10–7.07 (m, 1H), 4.62 (dt, J=47.2, 5.7 Hz, 2H), 3.39–3.29 (m, 9H), 3.05 (q, J=7.5 Hz, 2H), 1.86–1.73 (m, 2H), 1.35 (t, J=7.5 Hz, 3H); MS (EI) m/z 280.24 (M$^+$+H).

Step 4

Preparation of 2-ethyl-N-(3-fluoropropyl)-7-iodo-N-(2-methoxyethyl)pyrazolo[1,5-a]pyridin-3-amine Following the general procedure of EXAMPLE 1 (Step 4) and making non-critical variations, the title compound was prepared as a yellow oil (67%): $^1$H NMR (400 MHz, CDCl$_3$) δ 7.49 (d, J=8.5 Hz, 1H), 7.25 (d, J=7.0 Hz, 1H), 6.81–6.77 (m, 1H), 4.60 (dt, J=47.3, 5.8 Hz, 2H), 3.38–3.28 (m, 9H), 2.89 (q, J=7.6 Hz, 2H), 1.83–1.70 (m, 2H), 1.40 (t, J=7.6 Hz, 3H); MS (EI) m/z 406.17 (M$^+$+H).

Step 5

Preparation of 7-(2-chloro-4-methoxyphenyl)-2-ethyl-N-(3-fluoropropyl)-N-(2-methoxyethyl)pyrazolo[1,5-a]pyridin-3-amine Following the general procedure of EXAMPLE 1 (Step 5) and making non-critical variations, the title compound was prepared as a green oil (46%): $^1$H NMR (400 MHz, DMSO-$d_6$) δ 7.60 (d, J=8.9 Hz, 1H), 7.48 (d, J=8.6 Hz, 1H), 7.20 (d, J=2.5 Hz, 1H), 7.19–7.15 (m, 1H), 7.07 (dd, J=8.6, 2.5 Hz, 1H), 6.72 (d, J=6.9 Hz, 1H), 4.57 (dt, J=47.5, 5.9 Hz, 2H), 3.87 (s, 3H), 3.29–3.27 (m, 2H), 3.22–3.19 (m, 7H), 2.63 (q, J=7.5 Hz, 2H), 1.71–1.61 (m, 2H), 1.14 (t, J=7.5 Hz, 3H); $^{13}$C NMR (100 MHz, DMSO-$d_6$) δ 160.4, 153.2, 136.9, 136.6, 134.0, 132.6, 124.9, 122.0, 119.1, 115.8, 114.6, 113.0, 112.6, 81.0 (d, J=161.0 Hz), 70.8, 57.9, 55.6, 54.8, 51.3 (d, J=5.2 Hz), 29.5 (d, J=19.3 Hz), 18.9, 13.8; $^{19}$F NMR (376 MHz, DMSO-$d_6$) −219.0 (m); HRMS (FAB) calcd for $C_{22}H_{27}ClFN_3O_2$+H 420.1854. found 420.1871.

Example 20

7-(2,4-Dimethoxyphenyl)-2-ethyl-N-(3-fluoropropyl)-N-(2-methoxyethyl)pyrazolo[1,5-a]pyridin-3-amine

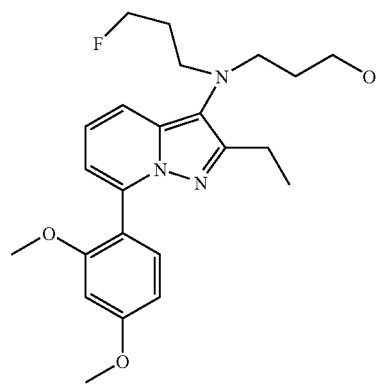

Following the general procedure of EXAMPLE 1 (Step 5) and making non-critical variations, the title compound was prepared as a light yellow oil (49%): $^1$H NMR (400 MHz, DMSO-$d_6$) δ 7.51 (d, J=9.0 Hz, 1H), 7.32 (d, J=8.5 Hz, 1H), 7.14–7.10 (m, 1H), 6.72 (d, J=2.3 Hz, 1H), 6.65–6.63 (m, 2H), 4.45 (dt, J=47.5, 5.9 Hz, 2H), 3.85 (s, 3H), 3.69 (s, 3H), 3.30–3.27 (m, 2H), 3.21–3.18 (m, 7H), 2.63 (q, J=7.6 Hz, 2H), 1.71–1.61 (m, 2H), 1.15 (t, J=7.6 Hz, 3H); $^{13}$C NMR (100 MHz, DMSO-$d_6$) δ 161.3, 158.5, 152.7, 137.3, 136.7, 131.6, 122.0, 118.7, 115.2, 114.8, 112.2, 104.8, 98.8, 81.0 (d, J=161.0 Hz), 70.9, 57.9, 55.5, 55.3, 54.8, 51.2 (d, J=5.3 Hz), 29.4 (d, J=19.3 Hz), 18.9, 13.8; $^{19}$F NMR (376 MHz, DMSO-$d_6$) −219.0 (m); HRMS (FAB) calcd for $C_{23}H_{30}FN_3O_3$+H 416.2349. found 416.2355.

Example 21

7-(2-Chloro-4-methoxyphenyl)-N,2-diethyl-N-(3-fluoropropyl)pyrazolo[1,5-a]pyridin-3-amine

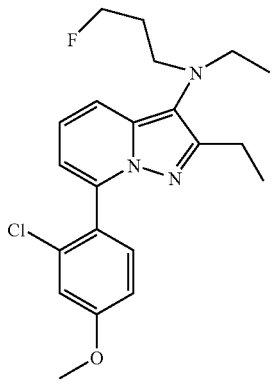

Step 1

Preparatin of N-(2-ethylpyrazolo[1,5-a]pyridin-3-yl)acetamide

Following the general procedure of EXAMPLE 3 (Step 1) and making non-critical variations, the title compound was prepared as a white solid (77%): mp 183.6–187.6° C.; $^1$H NMR (400 MHz, DMSO-$d_6$) δ 9.30 (s, 1H), 8.49 (d, J=7.0 Hz, 1H), 7.31 (d, J=9.0 Hz, 1H), 7.14–7.09 (m, 1H), 6.78–6.75 (m, 1H), 2.64 (q, J=7.6 Hz, 2H), 2.06 (s, 3H), 1.21 (t, J=7.6 Hz, 3H); $^{13}$C NMR (100 MHz, DMSO-$d_6$) δ 168.7, 151.1, 135.1, 128.2, 122.6, 116.3, 111.0, 106.9, 22.5, 18.9, 12.9; IR (diffuse reflectance) 3261, 2340, 1927, 1903, 1646, 1571, 1526, 1486, 1442, 1377, 1362, 757, 750, 726, 612 cm$^{-1}$; HRMS (FAB) calcd for $C_{11}H_{13}N_3O$+H 204.1137. found 204.1139; Anal. Calcd for $C_{11}H_{13}N_3O\cdot 0.05H_2O$: C, 64.72; H, 6.47; N, 20.58. Found: C, 64.55; H, 6.41; N, 20.58.

Step 2

Preparatin of N-(2-ethylpyrazolo[1,5-a]pyridin-3-yl)-N-(3-fluoropropyl)acetamide Following the general procedure of EXAMPLE 3 (Step 2) and making non-critical variations, the title compound was prepared as a white solid (44%): mp 76.6–79.6° C.; $^1$H NMR (400 MHz, DMSO-$d_6$) δ 8.65 (d, J=7.0 Hz, 1H), 7.51 (d, J=8.9 Hz, 1H), 7.31–7.27 (m, 1H), 6.92–6.88 (m, 1H), 4.51 (dt, J=47.3, 5.7 Hz, 2H), 4.00–3.93 (m, 1H), 3.43–3.36 (m, 1H), 2.67 (q, J=7.6 Hz, 2H), 1.90–1.71 (m, 2H), 1.67 (s, 3H), 1.28 (t, J=7.6 Hz, 3H); $^{13}$C NMR (100 MHz, DMSO-$d_6$) δ 170.8, 152.2, 136.3, 128.9, 124.9, 114.7, 112.0, 111.6, 81.0 (d, J=161.6 Hz), 44.7 (d, J=5.4 Hz), 29.0 (d, J=19.4 Hz), 21.3, 18.5, 12.6; $^{19}$F NMR (376 MHz, DMSO-$d_6$) −219.0 (m); IR (diffuse reflectance) 2977, 2431, 2367, 2343, 2261, 2059, 1655, 1641, 1499, 1454, 1397, 1383, 1365, 766, 751 cm$^{-1}$; HRMS (FAB) calcd for $C_{14}H_{18}FN_3O$+H 264.1512. found 264.1514; Anal. Calcd for $C_{14}H_{18}FN_3O$: C, 63.86; H, 6.89; N, 15.96. Found: C, 63.89; H, 6.99; N, 15.79.

Step 3

Preparatin of N,2-diethyl-N-(3-fluoropropyl)pyrazolo[1,5-a]pyridin-3-amine

Following the general procedure of EXAMPLE 19 (Step 3) and making non-critical variations, the title compound was prepared as a yellow oil (65%): $^1$H NMR (400 MHz, DMSO-$d_6$) δ 8.47 (d, J=7.0 Hz, 1H), 7.53 (d, J=8.8 Hz, 1H), 7.09–7.05 (m, 1H), 6.74–6.71 (m, 1H), 4.42 (dt, J=47.5, 5.9 Hz, 2H), 3.13 (t, J=7.0 Hz, 2H), 3.03 (q, J=7.1 Hz, 2H), 2.70 (q, J=7.6 Hz, 2H), 1.67 (m, 2H), 1.24 (t, J=7.6 Hz, 3H), 0.88 (t, J=7.0 Hz, 3H); $^{13}$C NMR (100 MHz, DMSO-$d_6$) δ 153.6, 136.1, 128.7, 122.3, 117.9, 116.3, 110.6, 82.7 (d, J=161.1 Hz), 50.6 (d, J=5.1 Hz), 49.4, 29.3 (d, J=19.2 Hz), 18.9, 13.6, 13.4; $^{19}$F NMR (376 MHz, DMSO-$d_6$) −218.9 (m); HRMS (FAB) calcd for $C_{14}H_{20}FN_3$+H 250.1719. found 250.1711.

Step 4

Preparatin of N,2-diethyl-N-(3-fluoropropyl)-7-iodopyrazolo[1,5-a]pyridin-3-amine Following the general procedure of EXAMPLE 1 (Step 4) and making non-critical variations, the title compound was prepared as a yellow oil (76%): $^1$H NMR (400 MHz, DMSO-$d_6$) δ 7.59 (d, J=9.0 Hz, 1H), 7.33 (d, J=7.0 Hz, 1H), 6.87–6.83 (m, 1H), 4.41 (dt, J=47.5, 5.9 Hz, 2H), 3.14 (t, J=7.0 Hz, 2H), 3.04 (q, J=7.1 Hz, 2H), 2.74 (q, J=7.6 Hz, 2H), 1.70–1.57 (m, 2H), 1.26 (t, J=7.6 Hz, 3H), 0.88 (t, J=7.1 Hz, 3H); $^{13}$C NMR (100 MHz, DMSO-$d_6$) δ 153.5, 136.9, 122.9, 122.2, 120.1, 116.1, 95.1, 82.6 (d, J=161.3 Hz), 50.5 (d, J=5.2 Hz), 49.3, 29.1 (d, J=19.3 Hz), 19.0, 13.6; $^{19}$F NMR (376 MHz, DMSO-$d_6$) −219.0 (m); HRMS (FAB) calcd for $C_{14}H_{19}FIN_3$+H 376.0688. found 376.0696.

Step 5

Preparatin of 7-(2-chloro-4-methoxyphenyl)-N,2-diethyl-N-(3-fluoropropyl)pyrazolo[1,5-a]pyridin-3-amine Following the general procedure of EXAMPLE 1 (Step 5) and making non-critical variations, the title compound was prepared as a brown oil (83%): $^1$H NMR (400 MHz, DMSO-$d_6$) δ 7.60 (d, J=8.7 Hz, 1H), 7.48 (d, J=8.5 Hz, 1H), 7.20 (d, J=2.5 Hz, 1H), 7.17–7.13 (m, 1H), 7.07 (dd, J=8.5, 2.5 Hz, 1H), 6.70 (d, J=6.7 Hz, 1H), 4.56 (dt, J=47.5, 5.9 Hz, 2H), 3.87 (s, 3H), 3.17 (t, J=7.0 Hz, 2H), 3.06 (q, J=7.1 Hz, 2H), 2.63 (q, J=7.6 Hz, 2H), 1.74–1.61 (m, 2H), 1.14 (t, J=7.6, Hz 3H), 0.91 (t, J=7.1 Hz, 3H); $^{13}$C NMR (100 MHz, DMSO-$d_6$) δ 160.4, 153.3, 137.0, 136.6, 134.0, 132.6, 125.0, 121.8, 118.6, 116.0, 114.6, 113.0, 112.4, 82.7 (d, J=161.1 Hz), 55.6, 50.6 (d, J=5.2 Hz), 49.4, 29.2 (d, 19.3 Hz), 19.0, 13.9, 13.7; IR (diffuse reflectance) 2968, 2932, 2910, 2477, 2362, 2338, 2286, 2176, 1601, 1490, 1440, 1300, 1232, 1044, 1028 cm$^{-1}$; HRMS (FAB) calcd for $C_{21}H_{25}ClFN_3O$+H 390.1748. found 390.1753; Anal. Calcd for $C_{21}H_{25}ClFN_3O$: C, 64.69; H, 6.46; N, 10.78. Found: C, 64.37; H, 6.52; N, 10.41.

Example 22

7-(2,4-Dimethoxyphenyl)-N,2-diethyl-N-(3-fluoropropyl)pyrazolo[1,5-a]pyridin-3-amine

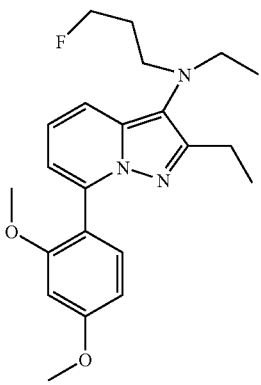

Following the general procedure of EXAMPLE 1 (Step 5) and making non-critical variations, the title compound was prepared as a yellow oil (67%): $^1$H NMR (400 MHz, CDCl$_3$) δ 7.52 (d, J=6.9 Hz, 1H), 7.44 (d, J=8.8 Hz, 1H), 7.07–7.03 (m, 1H), 6.68–6.64 (m, 3H), 4.63 (dt, J=47.4, 5.9 Hz, 2H), 3.92 (s, 3H), 3.80 (s, 3H), 3.28 (t, J=6.9 Hz, 2H), 3.15 (q, J=7.1 Hz, 2H), 2.78 (q, J=7.1 Hz, 2H), 1.86–1.73 (m, 2H), 1.29 (t, J=7.6 Hz, 3H), 1.03 (t, J=7.1 Hz, 3H); HRMS (FAB) calcd for C$_{22}$H$_{28}$FN$_3$O$_2$+H 386.2244. found 386.2260.

Example 23

7-(2-Chloro-4-methoxyphenyl)-2-ethyl-N-(3-fluoropropyl)-N-methylpyrazolo[1,5-a]pyridin-3-amine

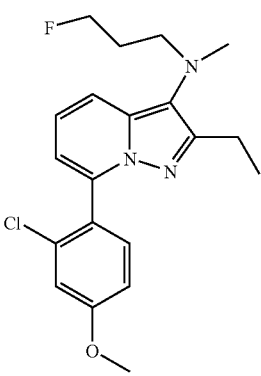

Step 1

Preparatin of 2-ethyl-N-(3-fluoropropyl)pyrazolo[1,5-a]pyridin-3-amine

A solution of N-(2-ethylpyrazolo[1,5-a]pyridin-3-yl)-N-(3-fluoropropyl)-2-methoxyacetamide (1.00 g, 3.39 mmol) in THF (12 mL) was added to a slurry of LAH (1.05 g, 27.7 mmol) in THF (6 mL) and the reaction was stirred at room temperature for 3.25 hours. The reaction was cooled to 0° C. and quenched with water (1 mL), 15% NaOH (3 mL) and water (3 mL). The mixture was filtered through diatomaceous earth and the filtrate was extracted with CH$_2$Cl$_2$, dried over MgSO$_4$ and concentrated in vacuo to give a brown oil which was subjected to column chromatography (50% ethyl acetate/hexane) to give 0.568 g (75%) of yellow oil as the title compound: $^1$H NMR (400 MHz, DMSO-d$_6$) δ 8.38 (d, J=7.0 Hz, 1H), 7.49 (d, J=9.0 Hz, 1H), 6.98–6.94 (m, 1H), 6.63–6.60 (m, 1H), 4.52 (dt, J=47.5, 5.9 Hz, 2H), 4.10 (br, 1H), 3.04 (t, J=6.9 Hz, 2H), 2.70 (q, J=7.6 Hz, 2H), 1.89–1.76 (m, 2H), 1.24 (t, J=7.6 Hz, 3H); $^{13}$C NMR (100 MHz, DMSO-d$_6$) δ 148.8, 133.1, 128.1, 120.7, 118.5, 116.0, 110.1, 81.1 (d, J=160.6 Hz), 45.6 (d, J=5.2 Hz), 30.8 (d, J=19.2 Hz), 18.6, 13.4; $^{19}$F NMR (376 MHz, DMSO-d$_6$) −219.0 (m); HRMS (FAB) calcd for C$_{12}$H$_{16}$FN$_3$+H 222.1406. found 222.1403.

Step 2

Preparatin of 2-ethyl-N-(3-fluoropropyl)-N-methylpyrazolo[1,5-a]pyridin-3-amine A solution of 2-ethyl-N-(3-fluoropropyl)pyrazolo[1,5-a]pyridin-3-amine (0.301 g, 1.36 mmol) in DMF (4 mL) was treated with K$_2$CO$_3$ (0.200 g, 1.45 mmol) and methyl iodide (0.06 mL, 0.96 mmol). The reaction was stirred at room temperature for 22 hours then concentrated in vacuo. The residue was partitioned between CH$_2$Cl$_2$ and water. The aqueous layer was extracted with CH$_2$Cl$_2$ and the combined organics was dried over MgSO$_4$, concentrated in vacuo to give 0.190 g (84%) of a brown oil as the title compound: $^1$H NMR (400 MHz, DMSO-d$_6$) δ 8.46 (d, J=6.9 Hz, 1H), 7.57 (d, J=8.9 Hz, 1H), 7.08–7.05 (m, 1H), 6.73–6.70 (m, 1H), 4.56 (dt, J=47.5, 5.9 Hz, 2H), 3.09 (t, J=7.0 Hz, 2H), 2.78 (s, 3H), 2.71 (q, J=7.6 Hz, 2H), 1.77–1.64 (m, 2H), 1.24 (t, J=7.6, Hz 3H); $^{13}$C NMR (100 MHz, DMSO-d$_6$) δ 152.3, 135.2, 128.7, 122.1, 120.9, 116.4, 110.6, 82.6 (d, J=161.4 Hz), 52.4 (d, J=5.2 Hz), 43.6, 29.0 (d, J=19.3 Hz), 19.0, 13.5; $^{19}$F NMR (376 MHz, DMSO-d$_6$) −219.0 (m); HRMS (FAB) calcd for C$_{13}$H$_{18}$FN$_3$+H 236.1563. found 236.1573.

Step 3

Preparatin of 2-ethyl-N-(3-fluoropropyl)-7-iodo-N-methylpyrazolo[1,5-a]pyridin-3-amine Following the general procedure of EXAMPLE 1 (Step 4) and making non-critical variations, the title compound was prepared as a yellow oil (44%): $^1$H NMR (400 MHz, DMSO-d$_6$) δ 7.62 (d, J=9.0 Hz, 1H), 7.32 (d, J=7.0 Hz, 1H), 6.86–6.82 (m, 1H), 4.44 (dt, J=47.5, 5.9 Hz, 2H), 3.10 (t, J=7.0 Hz, 2H), 2.78 (s, 3H), 2.75 (q, J=7.6 Hz, 2H), 1.77–1.65 (m, 2H), 1.26 (t, J=7.6, Hz 3H); $^{13}$C NMR (100 MHz, DMSO-d$_6$) δ 152.3, 136.0, 122.9, 122.7, 122.1, 116.2, 95.0, 82.6 (d, J=161.2 Hz), 52.3 (d, J=5.2 Hz), 43.4, 28.8 (d, J=19.5 Hz), 19.2, 13.7; $^{19}$F NMR (376 MHz, DMSO-d$_6$) −219.0 (m); HRMS (FAB) calcd for C$_{13}$H$_{17}$FIN$_3$+H 362.0531. found 362.0524.

Step 4

Preparatin of 7-(2-chloro-4-methoxyphenyl)-2-ethyl-N-(3-fluoropropyl)-N-methylpyrazolo[1,5-a]pyridin-3-amine Following the general procedure of EXAMPLE 1 (Step 5) and making non-critical variations, the title compound was prepared as a yellow oil (87%): $^1$H NMR (400 MHz, DMSO-d$_6$) δ 7.64 (d, J=8.8 Hz, 1H), 7.45 (d, J=8.6 Hz, 1H), 7.20 (d, J=2.4 Hz, 1H), 7.17–7.13 (m, 1H), 7.06 (dd, J=8.6, 2.4 Hz, 1H), 6.60 (d, J=6.7 Hz, 1H), 4.58 (dt, J=47.5, 5.9 Hz, 2H), 3.86 (s, 3H), 3.13 (t, J=7.0 Hz, 2H), 2.81 (s, 3H), 2.64 (q, J=7.5 Hz, 2H), 1.79–1.69 (m, 2H), 1.14 (t, J=7.5, Hz 3H); $^{13}$C NMR (100 MHz, DMSO-d$_6$) δ 160.4, 152.1, 136.9, 135.8, 134.0, 132.6, 125.0, 121.7, 121.5, 116.1, 114.6, 113.1, 112.4, 81.0 (d, J=161.1 Hz), 55.6, 52.5 (d, J=5.3 Hz), 29.0(d, 19.3 Hz), 19.1, 14.0; $^{19}$F NMR (376 MHz, DMSO-d$_6$) –219.0 (m); HRMS (FAB) calcd for C$_{20}$H$_{23}$ClFN$_3$O+H 376.1592. found 376.1589.

Example 24

7-(2,4-Dimethoxyphenyl)-N,2-diethyl-N-(2-fluoroethyl)pyrazolo[1,5-a]pyridin-3-amine

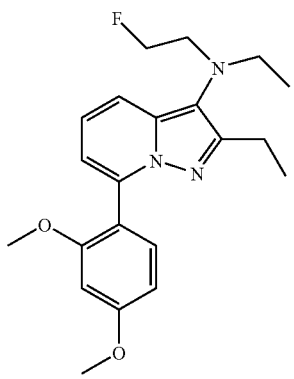

Step 1

Preparatin of N-(2-ethylpyrazolo[1,5-a]pyridin-3-yl)-N-(2-fluoroethyl)acetamide Following the general procedure of EXAMPLE 3 (Step 2) and making non-critical variations, the title compound was prepared as a brown oil (27%): $^1$H NMR (400 MHz, DMSO-d$_6$) δ 8.62 (d, J=6.8 Hz, 1H), 7.47 (d, J=8.8 Hz, 1H), 7.31–7.27 (m, 1H), 6.92–6.88 (m, 1H), 4.59–4.34 (m, 2H), 4.19–4.06 (m, 1H), 3.72–3.59 (m, 1H), 2.67 (q, J=7.6 Hz, 2H), 1.69 (s, 3H), 1.27 (t, J=7.6, Hz 3H); $^{13}$C NMR (100 MHz, DMSO-d$_6$) δ 171.3, 152.3, 136.3, 128.8, 124.8, 114.8, 112.0, 111.5, 82.1 (d, J=166.5 Hz), 48.1 (d, J=20.1 Hz), 21.3, 18.3, 12.5; $^{19}$F NMR (376 MHz, DMSO-d$_6$) –222.5 (m); HRMS (FAB) calcd for C$_{13}$H$_{16}$FN$_3$O+H 250.1356. found 250.1355.

Step 2

Preparatin of N,2-diethyl-N-(2-fluoroethyl)pyrazolo[1,5-a]pyridin-3-amine

Following the general procedure of EXAMPLE 19 (Step 3) and making non-critical variations, the title compound was prepared as a yellow oil (46%): $^1$H NMR (400 MHz, DMSO-d$_6$) δ 8.48 (d, J=7.0 Hz, 1H), 7.53 (d, J=9.0 Hz, 1H), 7.10–7.06 (m, 1H), 6.75–6.71 (m, 1H), 4.39 (dt, J=47.7, 5.0 Hz, 2H), 3.35 (dt, J=26.8, 5.1 Hz, 2H), 3.10 (q, J=7.1 Hz, 2H), 2.70 (q, J=7.6 Hz, 2H), 1.24 (t, J=7.6 Hz, 3H), 0.88 (t, J=7.1, Hz 3H); $^{13}$C NMR (100 MHz, DMSO-d$_6$) δ 153.8, 136.1, 128.7, 122.4, 117.7, 116.2, 110.7, 81.4 (d, J=166.4 Hz), 55.3 (d, J=19.9 Hz), 49.4, 18.8, 13.7, 13.4; $^{19}$F NMR (376 MHz, DMSO-d$_6$) –220.2 (m); HRMS (FAB) calcd for C$_{13}$H$_{18}$FN$_3$+H 236.1563. found 236.1570.

Step 3

Preparatin of N,2-diethyl-N-(2-fluoroethyl)-7-iodopyrazolo[1,5-a]pyridin-3-amine Following the general procedure of EXAMPLE 1 (Step 4) and making non-critical variations, the title compound was prepared as a white solid (88%): mp 51.2–53.6° C.; $^1$H NMR (400 MHz, DMSO-d$_6$) δ 7.57 (d, J=8.7 Hz, 1H), 7.35 (d, J=7.0 Hz, 1H), 6.88–6.84 (m, 1H), 4.28 (dt, J=47.8, 5.0 Hz, 2H), 3.36 (dt, J=27.0, 5.0 Hz, 2H), 3.11 (q, J=7.1 Hz, 2H), 2.74 (q, J=7.6 Hz, 2H), 1.26 (t, J=7.6 Hz, 3H), 0.88 (t, J=7.6 Hz, 3H); $^{13}$C NMR (100 MHz, DMSO-d$_6$) δ 153.8, 137.0, 122.9, 122.2, 119.9, 116.0, 95.1, 83.1 (d, J=166.3 Hz), 55.0 (d, J=20.0 Hz), 49.3, 18.9, 13.7, 13.5; $^{19}$F NMR (376 MHz, DMSO-d$_6$) –220.2 (m); IR (diffuse reflectance) 2966, 2931, 2455, 2362, 2327, 2266, 2229, 1520, 1483, 1334, 1306, 1182, 1065, 1031, 775 cm$^{-1}$; HRMS (FAB) calcd for C$_{13}$H$_{17}$FIN$_3$+H 362.0531. found 362.0537; Anal. Calcd for C$_{13}$H$_{17}$FIN$_3$.0.15H$_2$O: C, 42.91; H, 4.79; N, 11.55. Found: C, 42.86; H, 4.77; N, 11.47.

Step 4

Preparatin of 7-(2,4-dimethoxyphenyl)-N,2-diethyl-N-(2-fluoroethyl)pyrazolo[1,5-a]pyridin-3-amine Following the general procedure of EXAMPLE 1 (Step 5) and making non-critical variations, the title compound was prepared as a yellow oil (33%): $^1$H NMR (400 MHz, DMSO-d$_6$) δ 7.50 (d, J=8.9 Hz, 1H), 7.33 (d, J=8.5 Hz, 1H), 7.13–7.09 (m, 1H), 6.72 (d, J=2.3 Hz, 1H), 6.65–6.63 (m, 2H), 4.42 (dt, J=47.8, 5.0 Hz, 2H), 3.85 (s, 3H), 3.69 (s, 3H), 3.38 (dt, J=26.6, 5.0 Hz, 2H), 3.12 (q, J=7.1 Hz, 2H), 2.63 (q, J=7.6 Hz, 2H), 1.15 (t, J=7.6 Hz, 3H), 0.91 (t, J=7.1, Hz 3H); $^{13}$C NMR (100 MHz, DMSO-d$_6$) δ 161.3, 158.5, 153.0, 137.3, 136.7, 131.6, 121.9, 118.0, 115.3, 114.9, 112.2, 104.8, 98.8, 83.1 (d, J=166.4 Hz), 55.7, 55.3, 55.1, 49.5, 18.9, 13.9; $^{19}$F NMR (376 MHz, DMSO-d$_6$) –220.1 (m); HRMS (FAB) calcd for C$_{21}$H$_{26}$FN$_3$O$_2$+H 372.2087. found 372.2079.

Example 25

7-(2-Chloro-4-methoxyphenyl)-2-ethyl-N-(2-fluoroethyl)-N-(2-methoxyethyl)pyrazolo[1,5-a]pyridin-3-amine

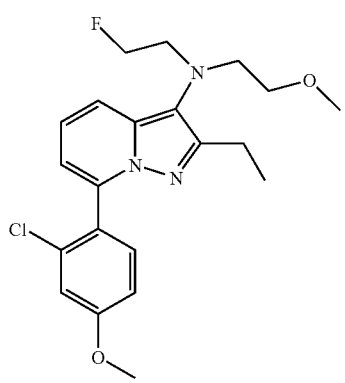

Step 1

Preparatin of N-(2-ethylpyrazolo[1,5-a]pyridin-3-yl)-N-(2-fluoroethyl)-2-methoxyacetamide Following the general procedure of EXAMPLE 3 (Step 2) and making non-critical variations, the title compound was prepared as a white solid (62%): mp 66.9–70.6° C.; $^1$H NMR (400 MHz, DMSO-d$_6$) δ 8.64 (d, J=6.8 Hz, 1H), 7.48 (d, J=8.8 Hz, 1H), 7.33–7.28 (m, 1H), 6.93–6.90 (m, 1H), 4.60–4.35 (m, 2H), 4.21–4.08 (m, 1H), 3.72–3.61 (m, 1H), 3.65 (d, J=15.4 Hz, 1H), 3.59 (d, J=15.4 Hz, 1H), 3.16 (s, 3H), 2.67 (q, J=7.6 Hz, 2H), 1.28 (t, J=7.6 Hz, 3H); $^{13}$C NMR (100 MHz, DMSO-d$_6$) δ 170.1, 152.5, 136.4, 128.9, 125.1, 114.7, 112.2, 108.8, 81.9 (d, J=166.5 Hz), 69.2, 58.2, 48.5 (d, J=20.0 Hz), 18.3, 12.4; $^{19}$F NMR (376 MHz, DMSO-d$_6$) –222.6 (m); IR (diffuse reflectance) 2971, 2958, 2488, 2432, 2350, 2339, 2253, 1681, 1497, 1451, 1415, 1397, 1135, 1102, 765 cm$^{-1}$; HRMS (FAB) calcd for $C_{14}H_{18}FN_3O_2$+H 280.1461. found 280.1469; Anal. Calcd for $C_{14}H_{18}FN_3O_2$: C, 60.20; H. 6.50; N, 15.04. Found: C, 60.18; H, 6.52; N, 15.01.

Step 2

Preparatin of 2-ethyl-N-(2-fluoroethyl)-N-(2-methoxyethyl)pyrazolo[1,5-a]pyridin-3-amine Following the general procedure of EXAMPLE 19 (Step 3) and making non-critical variations, the title compound was prepared as a yellow oil (37%): $^1$H NMR (400 MHz, DMSO-d$_6$) δ 8.48 (d, J=8.0 Hz, 1H), 7.52 (d, J=8.9 Hz, 1H), 7.12–7.08 (m, 1H), 6.76–6.72 (m, 1H), 4.38 (dt, J=47.7, 5.0 Hz, 2H), 3.33 (dt, J=31.7, 5.0 Hz, 2H), 3.28–3.21 (m, 4H), 3.17 (s, 3H), 2.70 (q, J=7.6 Hz, 2H), 1.24 (t, J=7.6 Hz 3H); $^3$C NMR (100 MHz, DMSO-d$_6$) δ 153.7, 136.2, 128.7, 122.5, 118.2, 116.0, 110.7, 83.1 (d, J=166.4 Hz), 70.9, 57.9, 55.8 (d, J=19.9 Hz), 54.9, 18.6, 13.3; $^{19}$F NMR (376 MHz, DMSO-d$_6$) –220.6 (m); HRMS (FAB) calcd for $C_{14}H_{20}FN_3O$+H 266.1669. found 266.1664.

Step 3

Preparatin of 2-ethyl-N-(2-fluoroethyl)-7-iodo-N-(2-methoxyethyl)pyrazolo[1,5-a]pyridin-3-amine Following the general procedure of EXAMPLE 1 (Step 4) and making non-critical variations, the title compound was prepared as a yellow oil (86%): $^1$H NMR (400 MHz, DMSO-d$_6$) δ 7.57 (d, J=8.7 Hz, 1H), 7.34 (d, J=7.0 Hz, 1H), 6.90–6.86 (m, 1H), 4.27 (dt, J=47.7, 5.0 Hz, 2H), 3.41 (dt, J=26.3, 5.0 Hz, 2H), 3.27–3.22 (m, 4H), 3.17 (s, 3H), 2.74 (q, J=7.6 Hz, 2H), 1.26 (t, J=7.6, Hz 3H); $^{13}$C NMR (100 MHz, DMSO-d$_6$) δ 153.6, 137.1, 123.0, 122.3, 120.4, 115.8, 95.1, 83.2 (d, J=163.4 Hz), 70.8, 57.9, 55.5 (d, J=19.8 Hz), 54.8, 18.8, 13.4; $^{19}$F NMR (376 MHz, DMSO-d$_6$) –220.6 (m); HRMS (FAB) calcd for $C_{14}H_{19}FIN_3O$+H 392.0637. found 392.0635.

Step 4

Preparatin of 7-(2-chloro-4-methoxyphenyl)-2-ethyl-N-(2-fluoroethyl)-N-(2-methoxyethyl)pyrazolo[1,5-a]pyridin-3-amine Following the general procedure of EXAMPLE 1 (Step 5) and making non-critical variations, the title compound was prepared as a yellow solid (63%): mp 45.8–52.8° C.; $^1$H NMR (400 MHz, DMSO-d$_6$) δ 7.59 (d, J=9.0 Hz, 1H), 7.47 (d, J=8.6 Hz, 1H), 7.21 (d, J=2.6 Hz, 1H), 7.19–7.16 (m, 1H), 7.07 (dd, J=8.6, 2.6 Hz, 1H), 6.72 (d, J=7.0 Hz, 1H), 4.29 (dt, J=47.8, 5.0 Hz, 2H), 3.87 (s, 3H), 3.37 (dt, J=26.5, 5.0 Hz, 2H), 3.30–3.25 (m, 4H), 3.19 (s, 3H), 2.64 (q, J=7.6 Hz, 2H), 1.14 (t, J=7.6, Hz 3H); $^{13}$C NMR (100 MHz, DMSO-d$_6$) δ 160.4, 153.4, 136.9, 136.7, 134.0, 132.6, 124.9, 122.1, 118.9, 115.7, 114.6, 113.1, 112.6, 83.2 (d, J=166.5 Hz), 71.0, 57.9, 55.9, 55.6, 54.9, 18.7, 13.8; $^{19}$F NMR (376 MHz, DMSO-d$_6$) –220.4 (m); IR (diffuse reflectance) 2961, 2941, 2461, 2367, 2280, 2176, 2107, 1491, 1302, 1232, 1048, 1034, 1008, 845, 782 cm$^{-1}$; HRMS (FAB) calcd for $C_{21}H_{25}ClFN_3O_2$+H 406.1698. found 406.1680; Anal. Calcd for $C_{21}H_{25}ClFN_3O_2$: C, 62.14; H, 6.21; N, 10.35. Found: C, 62.10; H, 6.19; N, 10.18.

Example 26

7-(2,4-Dimethoxyphenyl)-2-ethyl-N-(2-fluoroethyl)-N-(2-methoxyethyl)pyrazolo[1,5-a]pyridin-3-amine

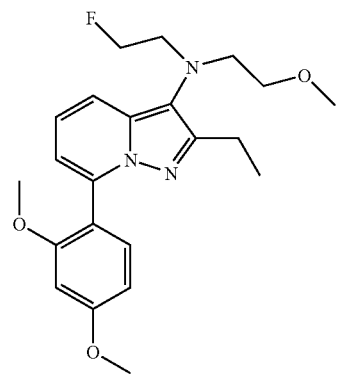

Following the general procedure of EXAMPLE 1 (Step 5) and making non-critical variations, the title compound was prepared as a yellow oil (75%): $^1$H NMR (400 MHz, DMSO-$d_6$) δ 7.50 (d, J=8.7 Hz, 1H), 7.32 (d, J=8.3 Hz, 1H), 7.15–7.11 (m, 1H), 6.72 (d, J=2.4 Hz, 1H), 6.66–6.63 (m, 2H), 4.29 (dt, J=47.8, 5.1 Hz, 2H), 3.85 (s, 3H), 3.69 (s, 3H), 3.42 (dt, J=26.5, 5.1 Hz, 2H), 3.31–3.26 (m, 4H), 3.20 (s, 3H), 2.63 (q, J=7.6 Hz, 2H), 1.15 (t, J=7.6 Hz, 3H); $^{13}$C NMR (100 MHz, DMSO-$d_6$) δ 161.4, 158.5, 152.9, 137.3, 136.8, 131.6, 122.1, 118.6, 115.2, 114.7, 112.3, 104.8, 98.8, 83.2 (d, J=166.4 Hz), 71.0, 57.9, 55.9, 55.7, 55.5, 55.3, 55.0, 18.7, 13.8; $^{19}$F NMR (376 MHz, DMSO-$d_6$) −220.5 (m); HRMS (FAB) calcd for $C_{22}H_{28}FN_3O_3$+H 402.2193. found 402.2187.

Example 27

N-(Cyclopropylmethyl)-7-(2,4-dichlorophenyl)-N,2-diethylpyrazolo[1,5-a]pyridin-3-amine

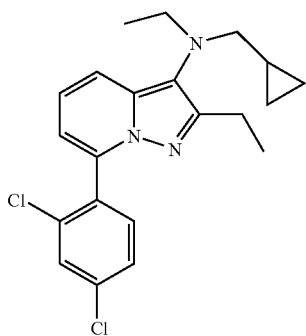

Step 1

Preparatin of N-(2-ethylpyrazolo[1,5-a]pyridin-3-yl) cyclopropanecarboxamide

Following the general procedure of EXAMPLE 3 (Step 1) and making non-critical variations, the title compound was prepared as a white solid (85%): IR (diffuse reflectance) 3256, 2965, 1640, 1569, 1550, 1527, 1487, 1441, 1400, 1365, 1317, 1226, 964, 748, 700 cm$^{-1}$; MS (EI) m/z 230 (M$^+$), 229 (M$^+$), 161, 160, 106, 105, 104, 79, 78, 69; Anal. Calcd for $C_{13}H_{15}N_3O$: C, 68.10; H, 6.59; N, 18.33. Found: C, 68.01; H, 6.76; N, 18.42.

Step 2

Preparatin of N-ethyl-N-(2-ethylpyrazolo[1,5-a]pyridin-3-yl)cyclopropanecarboxamide Following the general procedure of EXAMPLE 3 (Step 2) and making non-critical variations, the title compound was prepared as a clear oil (92%): $^1$H NMR (400 MHz, CDCl$_3$) δ 8.42 (d, J=7.0 Hz, 1H), 7.39 (d, J=8.9 Hz, 1H), 7.22–7.17 (m, 1H), 6.82–6.78 (m, 1H), 4.06–3.97 (m, 1H), 3.62–3.53 (m, 1H), 2.82 (q, J=7.6 Hz, 2H), 1.42–1.34 (m, 4H), 1.14 (t, J=7.2 Hz, 3H), 1.02–0.98 (m, 2H), 0.64–0.53 (m, 2H); IR (diffuse reflectance) 2980, 2968, 2935, 1646, 1494, 1448, 1411, 1371, 1311, 1261, 1128, 1115, 939, 761, 740 cm$^{-1}$; Anal. Calcd for $C_{15}H_{19}N_3O$: C, 70.01; H, 7.44; N, 16.33. Found: C, 69.88; H, 7.42; N, 16.31.

Step 3

Preparatin of N-(cyclopropylmethyl)-N,2-diethylpyrazolo[1,5-a]pyridin-3-amine

Following the general procedure of EXAMPLE 3 (Step 3) and making non-critical variations, the title compound was prepared as a yellow oil (70%): $^1$H NMR (400 MHz, CDCl$_3$) δ 8.32 (d, J=7.0 Hz, 1H), 7.47 (d, J=8.9 Hz, 1H), 6.98 (t, J=7.6 Hz, 1H), 6.62 (t, J=6.9 Hz, 1H), 3.19 (q, J=7.1 Hz, 2H), 2.94 (d, J=6.7 Hz, 2H), 2.87 (q, J=7.6 Hz, 2H), 1.37 (t, J=7.6 Hz, 3H), 0.99 (t, J=7.1 Hz, 3H), 0.87–0.78 (m, 1H), 0.40–0.35 (m, 2H), 0.06–0.03 (m, 2H); MS (EI) m/z 244.29 (M$^+$+H).

Step 4

Preparatin of N-(cyclopropylmethyl)-N,2-diethyl-7-iodopyrazolo[1,5-a]pyridin-3-amine Following the general procedure of EXAMPLE 1 (Step 4) and making non-critical variations, the title compound was prepared as a pale yellow oil (81%): $^1$H NMR (400 MHz, CDCl$_3$) δ 7.47 (dd, J=1, 9 Hz, 1H), 7.18 (dd, J=1, 7 Hz, 1H), 6.71–6.67 (m, 1H), 3.15 (q, J=7 Hz, 2H), 2.92–2.85 (m, 4H), 1.36 (t, J=8 Hz, 3H), 0.95 (t, J=7 Hz, 3H), 0.81–0.75 (m, 1H), 0.37–0.32 (m, 2H), 0.03–0.01 (m, 2H); MS (EI) m/z 370.2 (M$^+$+H).

Step 5

Preparatin of N-(cyclopropylmethyl)-7-(2,4-dichlorophenyl)-N,2-diethylpyrazolo[1,5-a]pyridin-3-amine Following the general procedure of EXAMPLE 1 (Step 5) and making non-critical variations, the title compound was prepared as a yellow oil (22%): $^1$H NMR (400 MHz, CDCl$_3$) δ 7.54–7.49 (m, 3H), 7.39–7.35 (m, 1H), 7.03–6.98 (m, 1H), 6.56 (d, J=7 Hz, 1H), 3.19 (q, J=7 Hz, 2H), 2.94 (d, J=7 Hz, 2H), 2.77 (q, J=8 Hz, 2H), 1.24 (t, J=8 Hz, 3H), 0.98 (t, J=7 Hz, 3H), 0.89–0.78 (m, 1H), 0.37–0.32 (m, 2H), 0.03–0.00 (m, 2H); HRMS (EI) calcd for $C_{21}H_{23}CL_2N_3$+H 388.1347. found 388.1354.

Example 28

7-(2-Chloro-4-methoxyphenyl)-N-(cyclopropylmethyl)-N,2-diethylpyrazolo[1,5-a]pyridin-3-amine

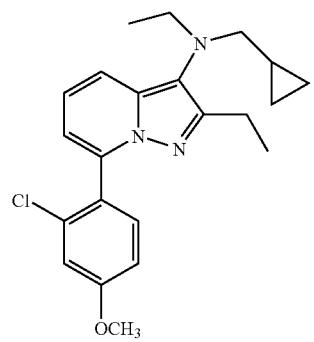

Following the general procedure of EXAMPLE 1 (Step 5) and making non-critical variations, the title compound was prepared as a yellow oil (72%): $^1$H NMR (400 MHz, CDCl$_3$) δ 7.50–7.47 (m, 2H), 7.08–7.06 (m, 1H), 7.02–6.98 (m, 1H), 6.95–6.90 (m, 1H), 6.56 (d, J=6 Hz, 1H), 3.87 (s, 3H), 3.19 (q, J=7 Hz, 2H), 2.94 (d, J=7 Hz, 2H), 2.78 (q, J=8 Hz, 2H), 1.23 (t, J=7 Hz, 3H), 0.98 (t, J=7 Hz, 3H), 0.94–0.79 (m, 1H), 0.37–0.33 (m, 2H), 0.24–0.01 (m, 2H); MS (EI) m/z 384.3 (M$^+$+H); HRMS (EI) calcd for C$_{22}$H$_{26}$ClN$_3$O+H 384.1842. found 384.1842.

Example 29

N-(Cyclopropylmethyl)-7-(2,4-dichlorophenyl)-2-ethyl-N-propylpyrazolo[1,5-a]pyridin-3-amine

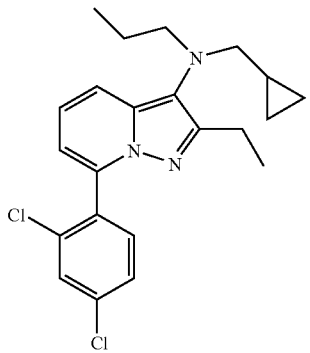

Step 1

Preparatin of N-(2-ethylpyrazolo[1,5-a]pyridin-3-yl)-N-propylcyclopropanecarboxamide Following the general procedure of EXAMPLE 3 (Step 2) and making non-critical variations, the title compound was prepared as a white solid (73%): $^1$H NMR (400 MHz, CDCl$_3$) δ 8.41 (d, J=7.0 Hz, 1H), 7.39 (d, J=8.9 Hz, 1H), 7.22–7.17 (m, 1H), 6.82–6.78 (m, 1H), 3.96–3.88 (m, 1H), 3.46–3.39 (m, 1H), 2.82 (q, J=7.6 Hz, 2H), 1.61–1.51 (m, 2H), 1.40 (t, J=7.6 Hz, 3H), 1.38–1.34 (m, 1H), 1.01–0.99 (m, 2H), 0.91 (t, J=7.4 Hz, 3H), 0.62–0.55 (m, 2H); IR (diffuse reflectance) 2962, 2956, 2931, 1654, 1639, 1498, 1445, 1408, 1379, 1368, 1244, 1134, 946, 755, 740 cm$^{-1}$; HRMS (FAB) calcd for C$_{16}$H$_{21}$N$_3$O+H 272.1763. found 272.1767; Anal. Calcd for C$_{16}$H$_{21}$N$_3$O: C, 70.82; H, 7.80; N, 15.48. Found: C, 70.79; H, 7.82; N, 15.52.

Step 2

Preparatin of N-(cyclopropylmethyl)-2-ethyl-N-propylpyrazolo[1,5-a]pyridin-3-amine Following the general procedure of EXAMPLE 3 (Step 3) and making non-critical variations, the title compound was prepared as a pale yellow oil (68%): $^1$H NMR (400 MHz, CDCl$_3$) δ 8.31 (d, J=7.0 Hz, 1H), 7.48 (d, J=7.7 Hz, 1H), 7.02–6.95 (m, 1H), 6.63–6.59 (m, 1H), 3.10 (t, J=7.2 Hz, 2H), 2.92 (d, J=6.8 Hz, 2H), 2.87 (q, J=7.6 Hz, 2H), 1.45–1.35 (m, 5H), 0.91 (t, J=7.4 Hz, 3H), 0.85–0.81 (m, 1H), 0.40–0.35 (m, 2H), 0.06–0.02 (m, 2H); MS (EI) m/z 258.2 (M$^+$+H).

Step 3

Preparatin of N-(cyclopropylmethyl)-2-ethyl-7-iodo-N-propylpyrazolo[1,5-a]pyridin-3-amine Following the general procedure of EXAMPLE 1 (Step 4) and making non-critical variations, the title compound was prepared as a yellow oil (86%): $^1$H NMR (400 MHz, CDCl$_3$) δ 7.48 (dd, J=1, 9 Hz, 1H), 7.17 (dd, J=1, 7 Hz, 1H), 6.71–6.67 (m, 1H), 3.07 (t, J=7 Hz, 2H), 2.88 (q, J=8 Hz, 4H), 1.39–1.33 (m, 5H), 0.86 (t, J=7 Hz, 3H), 0.85–0.77 (m, 1H), 0.37–0.33 (m, 2H), 0.02–0.01 (m, 2H); MS (EI) m/z 384.3 (M$^+$+H).

Step 4

Preparatin of N-(cyclopropylmethyl)-7-(2,4-dichlorophenyl)-2-ethyl-N-propylpyrazolo[1,5-a]pyridin-3-amine Following the general procedure of EXAMPLE 1 (Step 5) and making non-critical variations, the title compound was prepared as a yellow oil (88%): $^1$H NMR (400 MHz, CDCl$_3$) δ 7.55–7.49 (m, 3H), 7.39–7.35 (m, 1H), 7.03–6.98 (m, 1H), 6.56 (d, J=6 Hz, 1H), 3.13–3.07 (m, 2H), 2.91 (d, J=7 Hz, 2H), 2.77 (q, J=8 Hz, 2H), 1.42–1.36 (m, 2H), 1.23 (t, J=8 Hz, 3H), 0.89 (t, J=7 Hz, 3H), 0.87–0.78 (m, 1H), 0.36–0.33 (m, 2H), 0.02–0.00 (m, 2H); MS (EI) m/z 403.3 (M$^+$+H); HRMS (EI) calcd for C$_{22}$H$_{25}$Cl$_2$N$_3$+H 402.1504. found 402.1522.

Example 30

7-(2-Chloro-4-methoxyphenyl)-N-(cyclopropylmethyl)-2-ethyl-N-propylpyrazolo[1,5-a]pyridin-3-amine

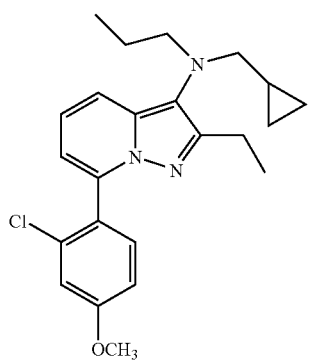

Following the general procedure of EXAMPLE 1 (Step 5) and making non-critical variations, the title compound was prepared as a yellow oil (85%): $^1$H NMR (400 MHz, CDCl$_3$) δ 7.49–7.46 (m, 2H), 7.06 (d, J=3 Hz, 1H), 7.02–6.97 (m, 1H), 6.94–6.90 (m, 1H), 6.56 (d, J=5 Hz, 1H), 3.87 (s, 3H), 3.10 (t, J=7 Hz, 2H), 2.91 (d, J=7 Hz, 2H), 2.78 (q, J=8 Hz, 2H), 1.43–1.38 (m, 2H), 1.24 (t, J=8 Hz, 3H), 0.89 (t, J=7 Hz, 3H), 0.87–0.75 (m, 1H), 0.36–0.33 (m, 2H), 0.02–0.01 (m, 2H); HRMS (EI) calcd for $C_{23}H_{28}ClN_3O+H$ 398.1999. found 398.2011.

Example 31

7-(2,4-Dichlorophenyl)-N-(1-ethylpropyl)-2-methylpyrazolo[1,5-a]pyridin-3-amine

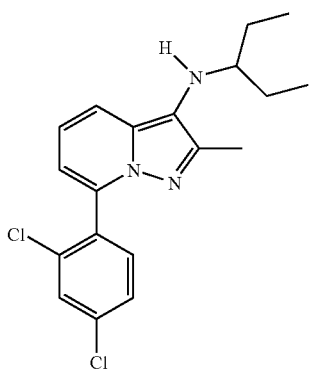

Step 1

Preparatin of N-(1-ethylpropyl)-2-methylpyrazolo[1,5-a]pyridin-3-amine

To a suspension of 2-methyl-3-amino-pyrazolo[1,5-a]pyridine (0.158 g, 1.07 mmol) and 3-pentanone (0.11 g, 0.14 mL, 1.29 mmol) in methanol (5.0 mL) was added $NaCNBH_3$ (0.095 g, 1.5 mmol) and a drop of acetic acid. The mixture was stirred at room temperature for 18 h. The reaction was partitioned between $CH_2Cl_2$ and $H_2O$. The layers were separated and the aqueous layer was extracted with $CH_2Cl_2$ (2×). The organic layers were combined and dried over $MgSO_4$ and filtered. The filtrate was concentrated in vacuo to dryness. The residue was subjected to column chromatography (15% ethyl acetate/hexane) to give 0.196 g (85%) of a yellow oil as the title compound: $^1H$ NMR (400 MHz, $CDCl_3$) δ 8.25 (d, J=7.0 Hz, 1H), 7.37 (d, J=8.9 Hz, 1H), 6.99–6.95 (m, 1H), 6.59 (t, J=6.8 Hz, 1H), 2.87 (quintet, J=5.9 Hz, 1H), 2.44 (s, 3H), 1.57–1.47 (m, 4H), 1.01 (t, J=7.4 Hz, 6H); HRMS (FAB) calcd for $C_{13}H_{19}N_3+H$ 218.1657. found 218.1647.

Step 2

Preparatin of N-(1-ethylpropyl)-7-iodo-2-methylpyrazolo[1,5-a]pyridin-3-amine

Following the general procedure of EXAMPLE 1 (Step 4) and making non-critical variations, the title compound was prepared as a yellow oil (11%): $^1H$ NMR (400 MHz, $CDCl_3$) δ 7.40 (d, J=8.8 Hz, 1H), 7.19 (d, J=7.0 Hz, 1H), 6.75–6.71 (m, 1H), 2.88 (quintet, J=5.9 Hz, 1H), 2.51 (s, 3H), 1.56–1.45 (m, 4H), 1.00 (t, J=7.4 Hz, 6H); MS (EI) m/z 344.2 ($M^++H$).

Step 3

Preparatin of 7-(2,4-dichlorophenyl)-N-(1-ethylpropyl)-2-methylpyrazolo[1,5-a]pyridin-3-amine Following the general procedure of EXAMPLE 1 (Step 5) and making non-critical variations, the title compound was prepared as a colorless solid (69%): $^1H$ NMR (400 MHz, $CDCl_3$) δ 7.59 (d, J=2.0 Hz, 1H), 7.51 (d, J=8.2 Hz, 1H), 7.45 (d, J=8.9 Hz, 1H), 7.41 (dd, J=8.2, 2.0 Hz, 1H), 7.07–7.03 (m, 1H), 6.57 (d, J=6.8 Hz, 1H), 2.91 (quintet, J=5.9 Hz, 1H), 3.00 (s, 3H), 1.58–1.50 (m, 4H), 1.03 (t, J=7.3 Hz, 6H); HRMS (FAB) calcd for $C_{19}H_{21}Cl_2N_3+H$ 362.1190. found 362.1175.

Example 32

7-(2,4-Dichlorophenyl)-N-[2-methoxy-1-(methoxymethyl)ethyl]-2-methylpyrazolo[1,5-a]pyridin-3-amine

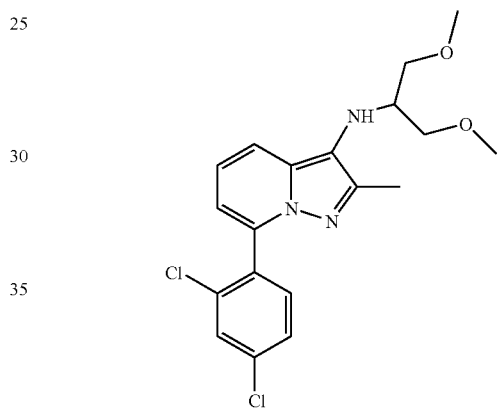

Step 1

Preparatin of 7-iodo-2-methylpyrazolo[1,5-a]pyridine

Following the general procedure of EXAMPLE 1 (Step 4) and making non-critical variations, the title compound was prepared as a yellow oil (66%): $^1H$ NMR (400 MHz, $CDCl_3$) δ 7.43–7.40 (m, 11H), 7.22 (dd, J=1, 7 Hz, 1H), 6.80–6.76 (m, 1H), 6.52 (s, 1H), 2.55 (s, 3H); MS (EI) m/z 259.0 ($M^++H$).

Step 2

Preparatin of 7-(2,4-dichlorophenyl)-2-methylpyrazolo[1,5-a]pyridine

Following the general procedure of EXAMPLE 1 (Step 5) and making non-critical variations, the title compound was prepared as a yellow solid (42%): mp 86.9–90.0° C.; $^1H$ NMR (400 MHz, DMSO-$d_6$) δ 7.83 (s, 1H), 7.65 (d, J=8.8 Hz, 1H), 7.59 (br, 2H), 7.27–7.23 (m, 11H), 6.81 (d, J=6.7 Hz, 11H), 6.49 (s, 11H), 2.31 (s, 3H); $^{13}C$ NMR (100 MHz, DMSO-$d_6$) δ 150.5, 140.8, 135.5, 134.7, 134.3, 133.0, 132.1, 129.0, 127.5, 123.0, 117.3, 112.5, 96.6, 13.7; IR (diffuse reflectance) 2489, 2437, 2348, 2289, 2069, 1532, 1480, 1302, 1057, 863, 811, 799, 785, 727, 716 cm$^{-1}$; HRMS (FAB) calcd for $C_{14}H_{10}Cl_2N_2$+H 277.0299. found 277.0292; Anal. Calcd for $C_{14}H_{10}Cl_2N_2$: C, 60.67; H, 3.64; N, 10.11. Found: C, 60.43; H, 3.50; N, 10.00.

Step 3

Preparatin of 7-(2,4-dichlorophenyl)-2-methyl-3-nitropyrazolo[1,5-a]pyridine

Following the general procedure of EXAMPLE 1 (Step 1) and making non-critical variations, the title compound was prepared as a yellow solid (35%): mp 146.5–150.5° C.; $^1$H NMR (400 MHz, DMSO-$d_6$) δ 8.35 (d, J=8.7 Hz, 11H), 8.00–7.96 (m, 1H), 7.91 (d, J=1.3 Hz, 11H), 7.70–7.65 (m, 2H), 7.44 (d, J=7.2 Hz, 11H), 2.61 (s, 31H); $^{13}$C NMR (100 MHz, DMSO-$d_6$) δ 150.5, 137.3, 137.1, 135.7, 134.2, 133.2, 132.1, 130.0, 129.1, 127.7, 122.6, 118.0, 117.6, 14.2; IR (diffuse reflectance) 2499, 2435, 2399, 2351, 2316, 1541, 1472, 1414, 1355, 1338, 1299, 1164, 1146, 811, 792 cm$^{-1}$; HRMS (FAB) calcd for $C_{14}H_9Cl_2N_3O_2$+H 322.0150. found 322.0152; Anal. Calcd for $C_{14}H_9Cl_2N_3O_2$: C, 52.20; H, 2.82; N, 13.04. Found: C, 51.35; H, 2.81; N, 13.07.

Step 4

Preparatin of 7-(2,4-dichlorophenyl)-2-methylpyrazolo[1,5-a]pyridin-3-amine

Following the general procedure of EXAMPLE 1 (Step 2) and making non-critical variations, the title compound was prepared as a yellow solid (73%): $^1$H NMR (400 MHz, DMSO-$d_6$) δ 7.79 (d, J=2.0 Hz, 1H), 7.60–7.52 (m, 3H), 6.94–6.91 (m, 1H), 6.53 (d, J=6.6 Hz, 1H), 4.18 (br, 2H), 2.18 (s, 3H); HRMS (FAB) calcd for $C_{14}H_{11}Cl_2N_3$+H 292.0408. found 292.0400.

Step 5

Preparatin of 7-(2,4-dichlorophenyl)-N-[2-methoxy-1-(methoxymethyl)ethyl]-2-methylpyrazolo[1,5-a]pyridin-3-amine Following the general procedure of EXAMPLE 31 (Step 1) and making non-critical variations, the title compound was prepared as a yellow oil (96%): $^1$H NMR (400 MHz, DMSO-$d_6$) δ 7.81 (s, 1H), 7.58–7.57 (m, 2H), 7.55 (d, J=8.8 Hz, 1H), 7.13–7.09 (m, 1H), 6.68 (d, J=6.6 Hz, 1H), 3.75 (br, 1H), 3.36 (d, J=5.4 Hz, 4H), 3.27 (s, 6H), 3.14 (br, 1H), 2.22 (s, 3H); $^{13}$C NMR (100 MHz, DMSO-$d_6$) δ 144.8, 135.1, 134.6, 134.5, 134.4, 133.1, 131.9, 128.9, 127.4, 120.8, 119.5, 116.0, 111.9, 73.8, 72.2, 59.0, 58.3, 58.2, 11.0; HRMS (FAB) calcd for $C_{19}H_{21}Cl_2N_3O_2$+H 394.1089. found 394.1074.

Example 33

7-(2,4-Dichlorophenyl)-2-ethyl-N-(1-ethylpropyl)pyrazolo[1,5-a]pyridin-3-amine

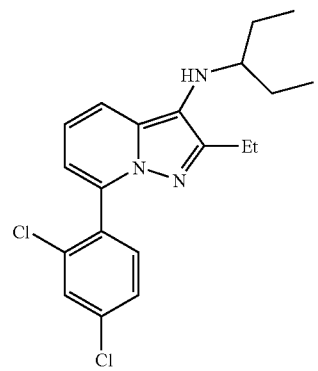

Step 1

Preparation of 7-(2,4-dichlorophenyl)-2-ethylpyrazolo[1,5-a]pyridine

Following the general procedure of EXAMPLE 1 (Step 5) and making non-critical variations, the title compound was prepared as a light yellow solid (40%): $^1$H NMR (400 MHz, CDCl$_3$) δ 7.59 (d, J=2.0 Hz, 1H), 7.57–7.52 (m, 2H), 7.42 (dd, J=2.0, 8.2 Hz, 1H), 7.16 (dd, J=6.9, 8.9 Hz, 1H), 6.67 (dd, J=1.3, 6.9 Hz, 1H), 6.46 (s, 1H), 2.85 (q, J=7.6 Hz, 2H), 1.34 (t, J=7.6 Hz, 3H); MS (EI) m/z 291 (M$^+$+H), 293 (M$^+$+H).

Step 2

Preparation of 7-(2,4-dichlorophenyl)-2-ethyl-3-nitropyrazolo[1,5-a]pyridine

Following the general procedure of EXAMPLE 1 (Step 1) and making non-critical variations, the title compound was prepared as a light yellow solid (47%): mp 147–149° C. (CH$_2$Cl$_2$/heptane); $^1$H NMR (400 MHz, CDCl$_3$) δ 8.46 (dd, J=1.3, 8.9 Hz, 1H), 7.75 (dd, J=7.2, 8.9 Hz, 1H), 7.63 (s, 1H), 7.50–7.45 (m, 2H), 7.12 (dd, J=1.3, 7.2 Hz, 1H), 3.18 (q, J=7.5 Hz, 2H), 1.33 (t, J=7.5 Hz, 3H); $^{13}$C NMR (100 MHz, CDCl$_3$) δ 156.7, 138.6, 138.5, 137.3, 135.6, 132.8, 130.8, 130.4, 130.2, 127.9, 123.4, 118.9, 117.7, 22.3, 12.7; IR (diffuse reflectance) 3090, 3081, 3067, 2984, 1632, 1587, 1555, 1536, 1473, 1443, 1364, 1307, 1297, 1157, 1146, 808, 803 cm$^{-1}$; MS (EI) m/z 336 (M$^+$+H), 338 (M$^+$+H); HRMS (FAB) calcd for $C_{15}H_{11}Cl_2N_3O_2$+H 336.0306. found 336.0309; Anal. Calcd for $C_{15}H_{11}Cl_2N_3O_2$: C, 53.59; H, 3.30; N, 12.50. Found: C, 53.68; H, 3.29; N, 12.41.

Step 3

Preparation of 7-(2,4-dichlorophenyl)-2-ethylpyrazolo[1,5-a]pyridin-3-amine

Following the general procedure of EXAMPLE 1 (Step 2) and making non-critical variations, the title compound was prepared as a yellow solid (99%): $^1$H NMR (400 MHz, CDCl$_3$) δ 7.46 (d, J=2.0 Hz, 1H), 7.39 (d, J=8.2 Hz, 1H), 7.33–7.28 (m, 2H), 6.94–6.90 (m, 1H), 6.45 (d, J=6.4 Hz, 1H), 2.70 (q, J=7.6 Hz, 2H), 1.19 (t, J=7.6 Hz, 3H); MS (EI) m/z 306 (M$^+$+H), 308 (M$^+$+H).

Step 4

Preparation of 7-(2,4-dichlorophenyl)-2-ethyl-N-(1-ethylpropyl)pyrazolo[1,5-a]pyridin-3-amine Following the general procedure of EXAMPLE 31 (Step 1) and making non-critical variations, the title compound was prepared as a yellow oil (62%): $^1$H NMR (400 MHz, CDCl$_3$) δ 7.58 (d, J=2.0 Hz, TH), 7.53 (d, J=8.2, Hz, 1H), 7.46 (dd, J=1.2, 8.9 Hz, 1H), 7.41 (dd, J=2.0, 8.2 Hz, 1H), 7.03 (dd, J=6.8, 8.9 Hz, 1H), 6.58 (d, J=1.2, 6.8 Hz, 1H), 2.97–2.91 (m, 1H), 2.82 (q, J=7.6 Hz, 2H), 1.62–1.51 (m, 4H), 1.30 (t, J=7.6 Hz, 3H), 1.04 (t, J=7.4 Hz, 6H); IR (liq.) 2964, 2933, 2874, 1996, 1632, 1589, 1555, 1508, 1474, 1459, 1307, 1200, 1100, 820, 777 cm$^{-1}$; MS (EI) m/z 376 (M$^+$+H), 378 (M$^+$+H); HRMS (FAB) calcd for C$_{19}$H$_{21}$Cl$_2$N$_3$+H 362.1347. found 362.1343.

Example 34

7-(2,4-Dichlorophenyl)-2-ethyl-N-12-methoxy-1-(methoxymethyl)ethyl]pyrazolo[1,5-a]pyridin-3-amine

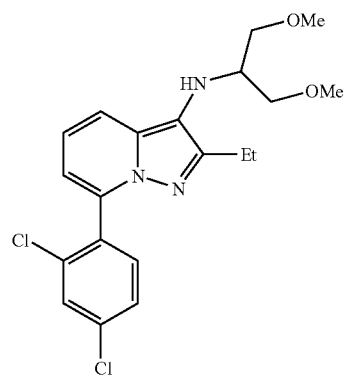

Following the general procedure of EXAMPLE 31 (Step 1) and making non-critical variations, the title compound was prepared as a yellow oil (41%): $^1$H NMR (400 MHz, CDCl$_3$) δ 7.47 (d, J=2.0 Hz, 1H), 7.43–7.41 (m, 2H), 7.29 (dd, J=2.0, 8.3 Hz, 1H), 6.96 (dd, J=6.8, 8.9 Hz, 1H), 6.50 (dd, J=1.3, 6.8 Hz, 1H), 3.41 (d, J=5.2 Hz, 4H), 3.32 (s, 6H), 3.22–3.14 (m, 1H), 2.69 (q, J=7.6 Hz, 2H), 1.18 (t, J=7.6 Hz, 3H); $^{13}$C NMR (100 MHz, CDCl$_3$) δ 150.2, 135.0, 134.7, 134.5, 134.0, 131.4, 130.5, 129.0, 128.7, 126.0, 121.2, 119.8, 116.0, 115.0, 114.7, 112.1, 111.4, 71.3, 58.3, 58.1, 17.9, 13.0; IR (liq.) 2977, 2929, 2891, 2878, 2820, 2068, 1996, 1590, 1511, 1475, 1458, 1199, 1114, 1102, 1056 cm$^1$; MS (EI) m/z 408 (M$^+$+H), 410 (M$^+$+H); HRMS (FAB) calcd for C$_{20}$H$_{23}$Cl$_2$N$_3$O$_2$+H 408.1245. found 408.1227.

Example 35

N-(sec-Butyl)-7-(2-chloro-4-methoxyphenyl)-2,6-dimethylpyrazolo[1,5-a]pyridin-3-amine

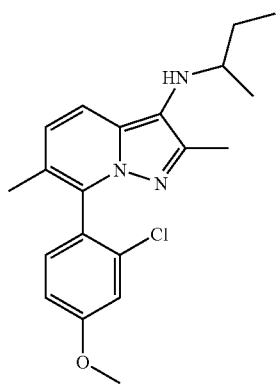

Step 1

Preparation of 2-(2-chloro-4-methoxyphenyl)-3-methylpyridine

Following the general procedure of EXAMPLE 1 (Step 5) and making non-critical variations, the title compound was prepared as a yellow oil (73%): $^1$H NMR (400 MHz, DMSO-d$_6$) δ 8.44 (d, J=4.6 Hz, 1H), 7.71 (d, J=7.5 Hz, 1H), 7.34–7.31 (m, 1H), 7.25 (d, J=8.5 Hz, 1H), 7.14 (d, J=2.4 Hz, 1H), 7.02 (d, J=8.5, 2.4 Hz, 1H), 3.84 (s, 3H), 2.08 (s, 3H); $^{13}$C NMR (100 MHz, DMSO-d$_6$) δ 159.4, 156.3, 146.4, 137.6, 132.2, 131.7, 131.5, 131.2, 122.8, 114.1, 113.3, 55.5, 18.3; HRMS (FAB) calcd for C$_{13}$H$_{12}$ClNO+H 234.0686. found 234.0687.

Step 2

Preparation of 1-amino-2-(2-chloro-4-methoxyphenyl)-3-methylpyridinium 2,4,6-trimethylbenzenesulfonate A 0° C. solution of ethyl O-mesitylsulfonylacetohydroxamate (4.68 g, 16.4 mmol) in dioxane (10 mL) was treated with HClO$_4$ (1.8 mL, 20.8 mmol) dropwise over 25 minutes. The reaction was stirred at 0° C. for two hours then poured into ice H$_2$O and stirred vigorously for 30 minutes. The mixture was filtered and the filter cake dissolved in CH$_2$Cl$_2$. The CH$_2$Cl$_2$ solution was washed with cold H$_2$O and passed through a plug of anhydrous K$_2$CO$_3$ directly into a flask containing a 0° C. solution of 2-(2-chloro-4-methoxyphenyl)-3-methylpyridine (1.37 g, 5.9 mmol) in CH$_2$Cl$_2$ (15 mL). The reaction was allowed to stir overnight at room temperature. Diethyl ether was added to the reaction and it was concentrated in vacuo to give a white foam (3.66 g) which was used as is in the next step: MS m/z 249.16 (M$^+$+H).

Step 3

Preparation of ethyl 7-(2-chloro-4-methoxyphenyl)-2,6-dimethylpyrazolo[1,5-a]pyridine-3-carboxylate A solution of crude 1-amino-2-(2-chloro-4-methoxyphenyl)-3-methylpyridinium 2,4,6-trimethylbenzenesulfonate (2.63 g, 5.9 mmol) in DMF (15 mL) was treated with $K_2CO_3$ (4.05 g, 29.3 mmol). A solution of ethyl but-2-ynoate (0.77 g, 6.9 mmol) in DMF (2 mL) was added and the reaction was stirred at ambient temperature for 16 hours then quenched with water and filtered to give a waxy yellow solid which was dissolved in $CH_2Cl_2$. The solution was washed with $H_2O$, dried over $MgSO_4$, and filtered. The filtrate was concentrated in vacuo to give a yellow oil (1.02 g). The original aqueous filtrate from the reaction was concentrated in vacuo to remove DMF and partitioned between $CH_2Cl_2$ and water. The aqueous layer was extracted with $CH_2Cl_2$ and the combined organic layers was dried over $MgSO_4$, concentrated in vacuo, combined with the yellow oil and subjected to column chromatography (30% ethyl acetate/heptane) to give 0.89 g (42%) of a yellow oil as the title compound: $^1H$ NMR (400 MHz, $CDCl_3$) δ 8.09 (d, J=9.0 Hz, 1H), 7.38 (d, J=9.0 Hz, 1H), 7.28 (d, J=8.5 Hz, 1H), 7.15 (d, J=2.5 Hz, 1H), 7.04 (dd, J=8.5, 2.5 Hz, 1H), 4.42 (q, J=7.1 Hz, 2H), 3.92 (s, 3H), 2.63 (s, 3H), 2.17 (s, 3H), 1.46 (t, J=7.1 Hz, 3H); MS m/z 359.39 ($M^+$+H).

Step 4

Preparation of 7-(2-chloro-4-methoxyphenyl)-2,6-dimethylpyrazolo[1,5-a]pyridine-3-carboxylic acid A solution of ethyl 7-(2-chloro-4-methoxyphenyl)-2,6-dimethylpyrazolo[1,5-a]pyridine-3-carboxylate (0.82 g, 2.3 mmol) in ethanol (14 mL), THF (8 mL) and $H_2O$ (8 mL) was treated with KOH (3.12 g, 55.6 mmol) and stirred at room temperature for 8 days adding more KOH periodically. The reaction was concentrated in vacuo and the residue partitioned between $Et_2O$ and $H_2O$. The aqueous layer was acidified with concentrated HCl, extracted with ethyl aceatate, washed with brine, dried over $MgSO_4$ and filtered. The filtrate was concentrated in vacuo to give a brown solid (0.60 g, 79%) as the title compound: $^1H$ NMR (400 MHz, $CDCl_3$) δ 8.18 (d, J=9.0 Hz, 1H), 7.43 (d, J=9.0 Hz, 1H), 7.30 (d, J=8.5 Hz, 1H), 7.16 (d, J=2.5 Hz, 1H), 7.04 (dd, J=8.5, 2.5 Hz, 1H), 3.93 (s, 3H), 2.67 (s, 3H), 2.19 (s, 3H); HRMS (FAB) calcd for $C_{17}H_{15}N_2O_3Cl$+H 331.0849. found 331.0853.

Step 5

Preparation of 7-(2-chloro-4-methoxyphenyl)-2,6-dimethylpyrazolo[1,5-a]pyridin-3-amine A 0° C. solution of 7-(2-chloro-4-methoxyphenyl)-2,6-dimethylpyrazolo[1,5-a]pyridine-3-carboxylic acid (0.58 g, 1.8 mmol) and triethylamine (0.30 mL, 2.2 mmol) in toluene (10 mL) was treated with diphenylphosphoryl azide (0.40 mL, 1.8 mmol) and stirred for 2.5 hours at 0° C. The reaction mixture was poured into $H_2O$, extracted with $Et_2O$, washed with brine, dried over $MgSO_4$, and filtered. The filtrate was concentrated in vacuo to remove the $Et_2O$. Toluene (20 mL) was added and the reaction was heated to reflux for 3 hours. The reaction was treated with 2N HCl (5 mL) and stirred at reflux for 1 hour then cooled to room temperature. The layers were separated and the aqueous layer was basified with solid $K_2CO_3$. The residue was extracted with $CH_2Cl_2$, dried over $MgSO_4$ and filtered. The filtrate was concentrated in vacuo to give 0.046 g (9%) of a yellow oily solid as the title compound: $^1H$ NMR (400 MHz, $CDCl_3$) δ 7.42 (d, J=7.1 Hz, 1H), 7.35 (d, J=9.3 Hz, 1H), 7.13 (d, J=2.5 Hz, 1H), 7.01 (dd, J=8.5, 2.5 Hz, 1H), 6.96 (d, J=8.8 Hz, 1H), 3.90 (s, 3H), 2.38 (s, 3H), 2.08 (s, 3H); MS (EI) m/z 302.18 ($M^+$+H).

Step 6

Preparation of N-(sec-butyl)-7-(2-chloro-4-methoxyphenyl)-2,6-dimethylpyrazolo[1,5-a]pyridin-3-amine Following the general procedure of EXAMPLE 31 (Step 1) and making non-critical variations, the title compound was prepared as a brown oil (52%): $^1H$ NMR (400 MHz, $CDCl_3$) δ 7.37 (d, J=8.9 Hz, 1H), 7.30 (d, J=9.1 Hz, 1H), 7.14 (d, J=2.5 Hz, 1H), 7.02 (dd, J=8.5, 2.5 Hz, 1H), 6.99 (d, J=9.0 Hz, 1H), 3.91 (s, 3H), 3.07–3.02 (m, 1H), 2.42 (br, 1H), 2.36 (s, 3H), 2.08 (s, 3H), 1.69–1.62 (m, 1H), 1.48–1.40 (m, 1H), 1.14 (d, J=6.2 Hz, 3H), 1.03 (t, J=7.4 Hz, 3H); HRMS (FAB) calcd for $C_{20}H_{24}N_3OCl$+H 358.1686. found 358.1675.

Example 36

7-(2,4-Dichlorophenyl)-N-(1-ethylpropyl)-2,6-dimethylpyrazolo[1,5-a]pyridin-3-amine

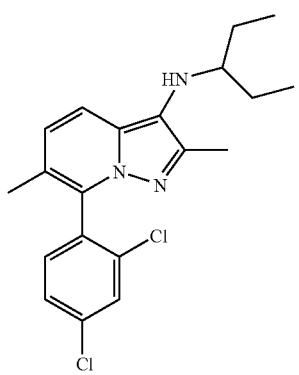

Step 1

Preparation of 2-(2,4-dichlorophenyl)-3-methylpyridine

Following the general procedure of EXAMPLE 1 (Step 5) and making non-critical variations, the title compound was prepared as a yellow solid (63%): mp 38.0–42.8° C.; $^1H$ NMR (400 MHz, DMSO-$d_6$) δ 8.48–8.43 (m, 1H), 7.77–7.75 (m, 2H), 7.53 (dd, J=8.3, 2.1 Hz, 1H), 7.41–7.36

(m, 2H), 2.08 (s, 3H); $^{13}$C NMR (100 MHz, DMSO-d$_6$) δ 155.3, 146.6, 138.1, 137.9, 133.4, 132.7, 131.9, 131.5, 128.7, 127.4, 123.3, 18.1; HRMS (FAB) calcd for C$_{12}$H$_9$Cl$_2$N+H 238.0190. found 238.0177; Anal. Calcd for C$_{12}$H$_9$Cl$_2$N: C, 60.28; H, 4.22; N, 5.86. Found: C, 60.26; H, 3.75; N, 5.82.

Step 2

Preparation of 1-amino-2-(2,4-dichlorophenyl)-3-methylpyridinium 2,4,6-trimethylbenzenesulfonate Following the general procedure of EXAMPLE 35 (Step 2) and making non-critical variations, the title compound was prepared as a white foam and used as is in the next step: MS m/z 255.03 (M$^+$+H).

Step 3

Preparation of ethyl 7-(2,4-dichlorophenyl)-2,6-dimethylpyrazolo[1,5-a]pyridine-3-carboxylate Following the general procedure of EXAMPLE 35 (Step 3) and making non-critical variations, the title compound was prepared as a white solid (41%): mp 119.8–123.7° C.; $^1$H NMR (400 MHz, DMSO-d$_6$) δ 8.02 (d, J=6.9 Hz, 1H), 7.90 (d, J=2.0 Hz, 1H), 7.64 (dd, J=8.2, 2.0 Hz, 1H), 7.61 (d, J=9.0 Hz, 1H), 7.57 (d, J=8.2 Hz, 1H), 4.32 (q, J=7.1 Hz, 2H), 2.45 (s, 3H), 2.08 (s, 3H), 1.35 (t, J=7.1 Hz, 3H); $^{13}$C NMR (100 MHz, DMSO-d$_6$) δ 163.1, 153.8, 140.1, 135.0, 134.2, 134.1, 133.1, 131.0, 130.2, 129.3, 128.0, 122.4, 117.4, 100.3, 59.3, 17.0, 14.3, 13.9; IR (diffuse reflectance) 2471, 2396, 2350, 2326, 2307, 1709, 1531, 1496, 1473, 1280, 1250, 1238, 1141, 1096, 810 cm$^{-1}$; HRMS (FAB) calcd for C$_{18}$H$_{16}$N$_2$O$_2$Cl$_2$+H 363.0667. found 363.0670; Anal. Calcd for C$_{18}$H$_{16}$Cl$_2$N$_2$O$_2$: C, 59.52; H, 4.44; N, 7.71. Found: C, 59.86; H, 4.62; N, 7.66.

Step 4

Preparation of 7-(2,4-dichlorophenyl)-2,6-dimethylpyrazolo[1,5-a]pyridine

Ethyl 7-(2,4-dichlorophenyl)-2,6-dimethylpyrazolo[1,5-a]pyridine-3-carboxylate (930 mg, 2.56 mmol) was treated with 50% H$_2$SO$_4$ (10 mL) and heated to 150° C. for 2.5 hours. The reaction was cooled in an ice bath and treated with 4N NaOH (19 mL) and NaHCO$_3$ (4.80 g).

The mixture was extracted three times with Et$_2$O and washed with brine, dried over MgSO$_4$ and filtered. The filtrate was concentrated in vacuo to dryness. The residue was subjected to column chromatography (25% ethyl acetate/heptane) to give 0.636 g (85%) of brown solid as the title compound: $^1$H NMR (400 MHz, CDCl$_3$) δ 7.63 (d, J=2.0 Hz, 1H), 7.47–7.44 (m, 2H), 7.37 (d, J=8.2 Hz, 1H), 7.08 (d, J=9.0 Hz, 1H), 6.35 (s, 1H), 2.44 (s, 3H), 2.10 (s, 3H); HRMS (FAB) calcd for C$_{15}$H$_{12}$N$_2$Cl$_2$+H 291.0456. found 291.0449.

Step 5

Preparation of 7-(2,4-dichlorophenyl)-2,6-dimethyl-3-nitropyrazolo[1,5-a]pyridine Following the general procedure of EXAMPLE 1 (Step 1) and making non-critical variations, the title compound was prepared as a yellow solid (5%): $^1$H NMR (400 MHz, CDCl$_3$) δ 8.36 (d, J=9.0 Hz, 1H), 7.67 (d, J=2.0 Hz, 1H), 7.65 (d, J=9.0 Hz, 1H), 7.50 (d, J=8.2, 2.0 Hz, 1H), 7.33 (d, J=8.3 Hz, 1H), 2.71 (s, 3H), 2.24 (s, 3H).

Step 6

Preparation of 7-(2,4-dichlorophenyl)-2,6-dimethylpyrazolo[1,5-a]pyridin-3-amine Following the general procedure of EXAMPLE 1 (Step 2) and making non-critical variations, the title compound was prepared as a green solid (84%): $^1$H NMR (400 MHz, CDCl$_3$) δ 7.61 (d, J=1.8 Hz, 1H), 7.43 (d, J=8.2 Hz, 1H), 7.40–7.32 (m, 2H), 7.05–6.95 (m, 1H), 3.40–2.80 (br, 2H), 2.36 (s, 3H), 2.07 (s, 3H); MS (EI) m/z 306.14 (M$^+$+H).

Step 7

Preparation of 7-(2,4-dichlorophenyl)-N-(1-ethylpropyl)-2,6-dimethylpyrazolo[1,5-a]pyridin-3-amine Following the general procedure of EXAMPLE 31 (Step 1) and making non-critical variations, the title compound was prepared as a yellow oil (67%): $^1$H NMR (400 MHz, DMSO-d$_6$) δ 7.84 (d, J=2.0 Hz, 1H), 7.58 (dd, J=8.1 Hz, 2.0 Hz, 1H), 7.50–7.46 (m, 2H), 7.00 (d, J=9.0 Hz, 1H), 3.58 (br, 1H), 2.75 (br, 1H), 2.16 (s, 3H), 1.96 (s, 3H), 1.42–1.38 (m, 3H), 0.92 (t, J=7.1 Hz, 6H); $^{13}$C NMR (100 MHz, DMSO-d$_6$) δ 143.0, 134.5, 134.4, 133.4, 132.7, 132.3, 131.1, 129.1, 127.8, 123.8, 119.3, 118.1, 115.6, 60.7, 26.1, 16.8, 11.4, 10.0; HRMS (FAB) calcd for C$_{20}$H$_{23}$N$_3$Cl$_2$+H 376.1347. found 376.1333.

Example 37

7-{[4-(Benzyloxy)pyridin-2-yl]oxy}-N,N-diethyltyrazolo[1,5-a]pyridin-3-amine

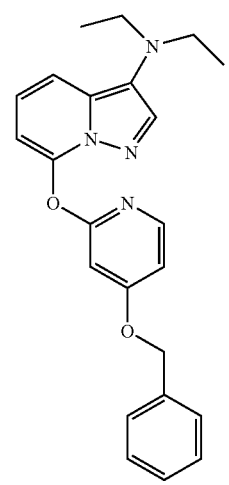

A mixture of N,N-diethyl-7-iodopyrazolo[1,5-a]pyridin-3-amine (0.25 g, 0.79 mmol), 4-benzyloxy-2(1H)-pyridone (0.19 g, 0.94 mmol), copper(1) iodide (0.003 g, 0.016 mmol) and potassium carbonate (0.13 g, 0.94 mmol) in DMF (5.0 mL) was heated at 150° C. for 3 h and cooled down to room temperature. The mixture was partitioned between EtOAc and H$_2$O and separated. The organic layer was concentrated in vacuo to dryness. The residue was subjected to column chromatography (E:H=1:4) to give 0.18 g (60%) of a clear oil as the title compound: $^1$H NMR (400 MHz, CDCl$_3$) δ 7.96 (d, J=5.8 Hz, 1H), 7.81 (s, 1H), 7.48–7.43 (m, 6H), 7.12–7.08 (m, 1H), 6.80 (s, 1H), 6.74 (d, J=5.8 Hz, 1H), 6.59 (d, J=6.4 Hz, 1H), 5.19 (s, 2H), 3.14 (q, J=7.1 Hz, 4H), 1.06 (t, J=7.1 Hz, 6H); MS (EI) m/z 389.25 (M$^+$+H).

Example 38

N,N-Diethyl-2-methyl-7-{[4-(Methylpyridin-2-yl]oxy}pyrazolo[1,5-a]pyridin-3-amine

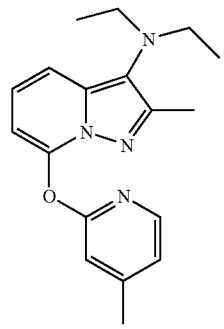

Following the general procedure of EXAMPLE 37 and making non-critical variations, the title compound was prepared as a clear oil (24%): $^1$H NMR (400 MHz, CDCl$_3$) δ 8.07 (d, J=5.1 Hz, 1H), 7.33 (d, J=7.8 Hz, 1H), 7.08–7.02 (m, 2H), 6.96 (d, J=7.2 Hz, 1H), 3.15 (q, J=7.1 Hz, 4H), 2.45 (s, 3H), 2.42 (s, 3H), 0.99 (t, J=7.1 Hz, 6H); HRMS (FAB) calcd for C$_{18}$H$_{22}$N$_4$O+H 311.1872. found 311.1855.

Example 39

3-sec-Butyl-7-(2,4-dichlorophenyl)-2-ethylpyrazolo[1,5-a]pyridine

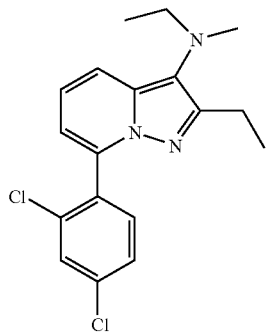

Step 1

Preparation of 1-(2-ethylpyrazolo[1,5-a]pyridin-3-yl)ethanone

Following the general procedure of EXAMPLE 35 (step 3) and making non-critical variations, the title compound was prepared as a tan solid (55%): mp 107.7–111.9° C. (EtoAc/hexanes); $^1$H NMR (400 MHz, CDCl$_3$) δ 8.48 (d, J=7.0 Hz, 1H), 8.19 (d, J=9.0 Hz, 1H), 7.45–7.41 (m, 1H), 6.96–6.93 (m, 1H), 3.15 (q, J=7.5 Hz, 2H), 2.61 (s, 3H), 1.41 (t, J=7.5 Hz, 3H); $^{13}$C NMR (100 MHz, CDCl$_3$) δ 192.1, 159.6, 142.1, 128.8, 128.2, 119.3, 113.7, 110.7, 30.5, 22.5, 13.3; IR (diffuse reflectance) 2963, 2479, 2445, 2429, 2408, 2365, 1645, 1639, 1513, 1455, 1351, 1268, 1207, 970, 751 cm$^{-1}$; HRMS (FAB) calcd for C$_{11}$H$_{12}$N$_2$O+H 189.1028. found 189.1029; Anal. Calcd for C$_{11}$H$_{12}$N$_2$O: C, 70.19; H, 6.43; N, 14.88. Found: C, 70.09; H, 6.47; N, 15.00.

Step 2

Preparation of 3-sec-butyl-2-ethylpyrazolo[1,5-a]pyridine

A 0° C. solution of 1-(2-ethylpyrazolo[1,5-a]pyridin-3-yl)ethanone (1.33 g, 7.1 mmol) in THF (20.0 mL) was treated with 1.0M THF solution of ethyl magnesium bromide (9.0 mL, 9.0 mmol). The reaction was allowed to warm to room temperature and stirred for 2.5 hours. An additional amount of ethyl magnesium bromide (2.0 mL, 2.0 mmol) was added and the reaction stirred for 1.5 hours. The reaction was quenched with 2N HCl then extracted with ethyl acetate, washed with brine, dried over MgSO$_4$ and filtered. The filtrate was concentrated in vacuo to dryness. The residue was subjected to column chromatography (20% ethyl acetate/heptane) to give 0.55 g (39%) of a yellow oil as a 4:1 mixture of the regio-isomers of 2-ethyl-3-[(1Z)-1-methylprop-1-enyl]pyrazolo[1,5-a]pyridine and 2-ethyl-3-(1-ethylvinyl)pyrazolo[1,5-a]pyridine. The mixture (0.22 mg, 1.1 mmol) was placed in a flask with cyclohexene (8.0 mL), 10% palladium on carbon (0.05 g) and AlCl$_3$ (0.016 g) and heated to 85° C. for 39 hours. The reaction was cooled to room temperature and filtered through diatomaceous earth. The filtrate was concentrated in vacuo to dryness. The residue was subjected to column chromatography (20% ethyl acetate/heptane) to give 0.19 g (86%) of a clear oil as the title compound: $^1$H NMR (400 MHz, CDCl$_3$) δ 8.36 (d, J=7.0 Hz, 1H), 7.45 (d, J=9.0 Hz, 1H), 7.00–6.96 (m, 1H), 6.64–6.60 (m, 1H), 2.93–2.82 (m, 3H), 1.83–1.74 (m, 2H), 1.40–1.33 (m, 6H), 0.87 (t, J=7.4 Hz, 3H); MS (EI) m/z 203.1 (M$^+$+H).

Step 3

Preparation of 3-sec-butyl-2-ethyl-7-iodopyrazolo[4,5-a]pyridine

Following the general procedure of EXAMPLE 1 (Step 4) and making non-critical variations, the title compound was prepared as a yellow oil (40%): $^1$H NMR (400 MHz, CDCl$_3$) δ 7.48 (d, J=8.9 Hz, 1H), 7.21 (d, J=7.0 Hz, 1H), 6.77–6.71

(m, 1H), 2.96–2.82 (m, 3H), 1.82–1.75 (m, 2H), 1.40–1.33 (m, 6H), 0.87 (t, J=7.4 Hz, 3H); MS (EI) m/z 329.13 (M⁺+H).

Step 4

Preparation of 3-sec-butyl-7-(2,4-dichlorophenyl)-2-ethylpyrazolo[1,5-a]pyridine Following the general procedure of EXAMPLE 1 (Step 5) and making non-critical variations, the title compound was prepared as a clear oil (46%): $^1$H NMR (400 MHz, CDCl$_3$) δ 7.60 (d, J=2.1 Hz, 1H), 7.59–7.53 (m, 2H), 7.42 (dd, J=8.3, 2.1 Hz, 1H), 7.14–7.08 (m, 1H), 6.68 (d, J=6.8 Hz, 1H), 2.95–2.88 (m, 1H), 2.80 (q, J=7.6 Hz, 2H), 1.86–1.78 (m, 2H), 1.45 (d, J=7.1 Hz, 3H), 1.27 (t, J=7.6 Hz, 3H), 0.91 (t, J=7.4 Hz, 3H);

Example 40

7-(2-Chloro-4-methoxyphenyl)-3-isopropyl-2-methylpyrazolo[1,5-a]pyridine

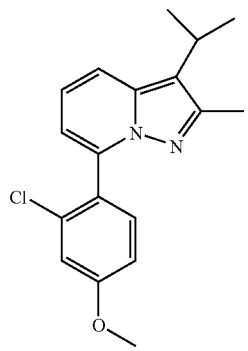

Step 1

Preparation of 1-(2-methylpyrazolo[1,5-a]pyridin-3-yl)ethanone

Following the general procedure of EXAMPLE 35 (Step 3) and making non-critical variations, the title compound was prepared as yellow solid (34%): mp 85.2–88.1° C.; $^1$H NMR (400 MHz, DMSO-d$_6$) δ 8.77 (d, J=6.7 Hz, 1H), 8.15 (d, J=8.8 Hz, 1H), 7.60–7.55 (m, 1H), 7.13–7.09 (m, 1H), 2.63 (s, 3H), 2.53 (s, 3H); $^{13}$C NMR (100 MHz, DMSO-d$_6$) δ 191.5, 153.7, 141.0, 129.1, 128.7, 118.3, 114.1, 110.3, 30.4, 15.1; IR (diffuse reflectance) 2492, 2447, 2428, 2399, 2361, 1644, 1639, 1506, 1439, 1428, 1414, 1376, 773, 750, 735 cm$^{-1}$; HRMS (FAB) calcd for C$_{10}$H$_{10}$N$_2$O+H 175.0871. found 175.0872; Anal. Calcd for C$_{10}$H$_{10}$N$_2$O: C, 68.95; H, 5.79; N, 16.08. Found: C, 68.95; H, 5.82; N, 16.02.

Step 2

Preparation of 3-isopropenyl-2-methylpyrazolo[1,5-a]pyridine

A 0° C. solution of 1-(2-methylpyrazolo[1,5-a]pyridin-3-yl)ethanone (1.05 g, 6.0 mmol) in ether (20 mL) was treated with 3.0 M ether solution of methyl magnesium bromide (4 mL, 12.0 mmol). The reaction was allowed to warm to room temperature and stirred for 7 hours. The reaction was quenched with 2N HCl then extracted with ethyl acetate, washed with brine, dried over MgSO$_4$ and filtered. The filtrate was concentrated in vacuo to dryness. The residue was subjected to column chromatography (50% ethyl acetate/heptane) to give 0.562 g (55%) of brown oil as the title compound: $^1$H NMR (400 MHz, DMSO-d$_6$) δ 8.53 (d, J=7.0 Hz, 1H), 7.61 (d, J=8.0 Hz, 1H), 7.19–7.15 (m, 1H), 6.82–6.78 (m, 1H), 5.20–5.19 (m, 1H), 5.04–5.03 (m, 1H), 2.42 (s, 3H), 2.16 (s, 3H); $^{13}$C NMR (100 MHz, DMSO-d$_6$) δ 148.1, 137.5, 136.1, 128.2, 123.7, 117.0, 113.7, 111.2, 110.7, 23.6, 13.6; HRMS (FAB) calcd for C$_{11}$H$_{12}$N$_2$+H 173.1079. found 173.1076.

Step 3

Preparation of 3-isopropyl-2-methylpyrazolo[1,5-a]pyridine

A solution of 3-isopropenyl-2-methylpyrazolo[1,5-a]pyridine (0.43 g, 2.5 mmol) in CH$_2$Cl$_2$ (30 mL) was treated with triethylsilane (3 mL, 18.8 mmol) and TFA (6 mL). The reaction was stirred at room temperature for 15 hours then quenched with saturated NaHCO$_3$. The layers were separated and the aqueous layer was extracted with CH$_2$Cl$_2$ and the combined organic layers was dried over MgSO$_4$ and filtered. The filtrate was concentrated in vacuo to dryness. The residue was subjected to column chromatography (20% ethyl acetate/heptane) to give 0.19 g (44%) of a yellow oil as the title compound: $^1$H NMR (400 MHz, DMSO-d$_6$) δ 8.45 (d, J=7.0 Hz, 1H), 7.59 (d, J=8.9 Hz, 1H), 7.07–7.03 (m, 1H), 6.71–6.68 (m, 1H), 3.20–3.09 (m, 1H), 2.35 (s, 3H), 1.31 (d, J=7.1 Hz, 6H); $^{13}$CNMR (100 MHz, DMSO-d$_6$) δ 147.5, 137.1, 128.1, 121.9, 116.6, 113.5, 110.2, 23.8, 22.7, 12.4; HRMS (FAB) calcd for C$_{11}$H$_{14}$N$_2$+H 175.1235. found 175.1236.

Step 4

Preparation of 7-iodo-3-isopropyl-2-methylpyrazolo[1,5-a]pyridine

Following the general procedure of EXAMPLE 1 (Step 4) and making non-critical variations, the title compound was prepared as a brown oil (54%): $^1$H NMR (400 MHz, DMSO-d$_6$) δ 7.64 (d, J=8.8 Hz, 1H), 7.29 (d, J=7.0 Hz, 1H), 6.85–6.81 (m, 1H), 3.15–3.11 (m, 1H), 2.40 (s, 3H), 1.30 (d, J=7.1 Hz, 6H); $^{13}$C NMR (100 MHz, DMSO-d$_6$) δ 147.2, 137.3, 122.6, 121.8, 116.4, 115.9, 93.4, 24.2, 22.5, 12.6; HRMS (FAB) calcd for C$_{11}$H$_{13}$IN$_2$+H 301.0203. found 301.0199.

Step 5

Preparation of 7-(2-chloro-4-methoxyphenyl)-3-isopropyl-2-methylpyrazolo[1,5-a]pyridine Following the general procedure of EXAMPLE 1 (Step 5) and making non-critical variations, the title compound was prepared as a yellow solid (54%): mp 111.9–114.9° C.; $^1$H NMR (400 MHz, DMSO-d$_6$) δ 7.66 (d, J=9.0 Hz, 1H), 7.42 (d, J=8.6 Hz, 1H), 7.20 (d, J=2.5 Hz, 1H), 7.16–7.12 (m, 1H), 7.06 (dd, J=8.5, 2.5 Hz, 1H), 6.66 (d, J=6.8 Hz, 1H), 3.86 (s, 3H), 3.21–3.14 (m, 1H), 2.28 (s, 3H), 1.34 (d, J=7.1 Hz, 6H); $^{13}$C NMR (100 MHz, DMSO-d$_6$) δ 160.3, 147.3, 137.6, 136.5, 133.8, 132.5, 125.4, 121.6, 116.3, 114.6, 113.9, 113.1, 112.0, 55.6, 23.8, 22.7, 12.6; IR (diffuse reflectance) 2963, 2459, 2409, 2350, 2283, 2171, 1601, 1489, 1234, 1228, 1026, 872, 854, 818, 790 cm$^{-1}$; HRMS (FAB) calcd for $C_{18}H_{19}ClN_2O$+H 315.1264. found 315.1260; Anal. Calcd for $C_{18}H_{19}ClN_2O \cdot 0.2H_2O$: C, 67.90; H, 6.14; N, 8.80. Found: C, 67.90; H, 6.11; N, 8.56.

Example A

In Vitro CRF$_1$ Receptor Binding Assay for the Evaluation of Biological Activity The following is a description of a standard in vitro binding assay for the evaluation of biological activity of a test compound on CRF$_1$ receptors. It is based on a modified protocol described by De Souza (De Souza, 1987).

The binding assay utilizes brain membranes, commonly from rats. To prepare brain membranes for binding assays, rat frontal cortex is homogenized in 10 mL of ice cold tissue buffer (50 mM HEPES buffer pH 7.0, containing 10 mM MgCl$_2$, 2 mM EGTA, 1 μg/mL aprotinin, 1 μg/mL leupeptin and 1 μg/mL pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 μg/mL.

Binding assays are performed in 96 well plates at a final volume of 300 μL. The assays are initiated by the addition of 150 μL membrane suspension to 150 μL of assay buffer containing $^{125}$I-ovine-CRF (final concentration 150 pM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvestor. Filters are washed three times with ice cold phosphate buffered saline pH 7.0 containing 0.01% Triton X-100. Filters are assessed for radioactivity in a Packard TopCount.

Alternatively, tissues and cells that naturally express CRF receptors, such as IMR-32 human neuroblastoma cells (ATCC; Hogg et al., 1996), can be employed in binding assays analogous to those described above.

A compound is considered to be active if it has an IC$_{50}$ value of less than about 10 μM for the inhibition of CRF. Nonspecific binding is determined in the presence of excess (10 μM) α-helical CRF.

Example B

Ex Vivo CRF$_1$ Receptor Binding Assay for the Evaluation of Biological Activity The following is a description of a typical ex vivo CRF$_1$ receptor binding assay for assessing the biological activity of a test compound on CRF$_1$ receptors.

Fasted, male, Harlen-bred, Sprague-Dawley rats (170–210 g) were orally dosed with test compound or vehicle, via gastric lavage between 12:30 and 2:00 PM. Compounds were prepared in vehicle (usually 10% soybean oil, 5% polysorbate 80, in dH20). Two hours after drug administration, rats were sacrificed by decapitation, frontal cortices were quickly dissected and placed on dry ice, then frozen at −80° C. until assayed; trunk blood was collected in heparinized tubes, plasma separated by centrifugation (2500 RPM's for 20 minutes), and frozen at −20° C.

On the day of the binding assay, tissue samples were weighed and allowed to thaw in ice cold 50 mM Hepes buffer (containing 10 mM MgCl$_2$, 2 mM EGTA, 1 μg/mL aprotinin, 1 μg/mL leupeptin hemisulfate, and 1 μg/mL pepstatin A, 0.15 mM bacitracin, and 0.1% ovalalbumin, pH=7.0 at 23° C.) and then homogenized for 30 sec at setting 5 (Polytron by Kinematica). Homogenates were incubated (two hours, 23° C., in the dark) with [$^{125}$I] CRF (0.15 nM, NEN) in the presence of assay buffer (as described above) or DMP-904 (10 uM). The assay was terminated by filtration (Packard FilterMate, GF/C filter plates); plates were counted in Packard TopCount LSC; total and non-specific fmoles calculated from DPM's. Data are expressed as % of vehicle controls (specific fmoles bound). Statistical significance was determined using student's t-test.

Example C

Inhibition of CRF Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Example D

In Vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). A compound may be tested in any species of rodent or small mammal.

What is claimed is:

1. A compound of formula I:

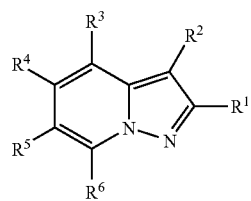

Formula I a stereoisomer thereof, a pharmaceutically acceptable salt thereof, or a prodrug thereof, wherein:

$R^1$ is selected from —H, —$NR^7R^8$, —$OR^7$, —$S(O)_mR^7$, —$C(O)R^7$, —$C(S)R^7$, —$C(O)OR^7$, —$C(S)OR^7$, —$C(O)NR^7R^8$, —$C(S)NR^7R^8$, alkyl, substituted alkyl, cycloalkyl, substituted cycloalkyl, heterocycloalkyl, and substituted heteracycloalkyl;

$R^2$ is selected from —$NR^7R^8$;

$R^3$, $R^4$ and $R^5$ can be the same or different and are independently selected from —H, alkyl, substituted alkyl, $R^6$ is selected from aryl, substituted aryl, heteroaryl, and substituted heteroaryl, and —$NR^{11}R^{12}$;

$R^7$ and $R^8$ (1) can be the same or different and are independently selected from —H, alkyl, substituted alkyl, cycloalkyl, substituted cycloalkyl, aryl, substituted aryl, hereroaryl, and substituted heteroaryl, provided that $R^7$ and $R^8$ are not both H; or (2) when both $R^7$ and $R^8$ are alkyls and attached to a nitrogen, may form, along with the nitrogen, a 3–8 membered mono heterocyclic ring, which may be optionally substituted with 1 to 3 substituents selected from halogen, —$R^9$, —$OR^9$, —$S(O)_mR^9$, —$NR^9R^{10}$, —$C(O)R^9$, —$C(S)R^9$, —CN, —$C(O)NR^9R^{10}$, —$C(S)NR^9R^{10}$, —$NR^9C(O)R^{10}$, —$NR^9C(S)R^{10}$, —$S(O)_nNR^9R^{10}$, —$NR^9S(O)_nR^{10}$, —$NO_2$, —$C(O)OR^9$ and —$C(S)R^9$, or (3) when $R^7$ and $R^8$ are attached to a nitrogen and $R^7$ is alkyl and $R^8$ is either cycloalkyl or aryl, substituted aryl, heteroaryl, and substituted heteroaryl, form a 7–12 meinbered bicyclic heterocyclic ring, which may be optionally substituted with 1 to 3 substituents selected from halogen, —$R^9$, —$OR^9$, —$S(O)_mR^9$, —$NR^9R^{10}$, —$C(O)R^9$, —$C(S)R^9$, —CN, —$C(O)NR^9R^{10}$, —$C(S)NR^9R^{10}$, —$NR^9C(O)R^{10}$, —$NR^9C(S)R^{10}$, —$S(O)_nNR^9R^{10}$, —$NR^9S(O)_nR^{10}$, —$NO_2$, —$C(O)OR^9$ and —$C(S)OR^9$;

$R^9$ and $R^{10}$ can be the same or different and are independently selected from —H, alkyl, substituted alkyl, cycloalkyl, substituted cycloalkyl, and aryl, substituted aryl, heteroaryl, and substituted heteroaryl;

$R^{11}$ and $R^{12}$ (1) can be the same or different and are independently selected from H, cycloalkyl, substituted cycloalkyl, heterocycloalkyl, substituted heterocycloalkyl, aryl, substituted aryl, heteroaryl, and substituted heteroaryl, or (2) can form a 5- or 6-membered monocylic or a 8–10-membered bicyclic heteroaryl ring system, which may optionally contain, in addition to the nitrogen, an additional heteroatom selected from N, S, and O, and which may optionally have an oxo substituent on the ring and also may be optionally substituted with 1 to 3 substituents selected from halogen, —$R^9$, —$OR^9$, —$S(O)_mR^9$, —$NR^9R^{10}$, —$C(O)R^9$, —$C(S)R^9$, —CN, —$C(O)NR^9R^{10}$, —$C(S)NR^9R^{10}$, —$NR^9C(O)R^{10}$, —$NR^9C(S)R^{10}$, —$S(O)_nNR^9R^{10}$, —$NR^9S(O)_nR^{10}$, —$NO_2$, —$C(O)OR^9$ and —$C(S)OR^9$;

m is 0, 1 or 2; and n is 1 or 2.

2. A compound according to claim 1, wherein in formula I, $R^1$ is selected from alkyl, substituted alkyl, cycloalkyl, substituted cycloalkyl, —$NR^7R^8$, —$OR^7$, and —$S(O)_mR^7$;

$R^2$ is selected from heterocycloalkyl, substituted heterocycloalkyl, $R^3$, $R^4$, and $R^5$ can be the same or different and are independently selected from —H, alkyl, substituted alkyl; and $R^6$ is selected from aryl, substituted aryl, heteroaryl, and substituted heteroaryl, and —$NR^{11}R^{12}$.

3. A compound according to claim 2, wherein in formula I, $R^1$ is selected from alkyl, substituted alkyl, —$NR^7R^8$, —$OR^7$, and —$S(O)_mR^7$;

$R^2$ is selected from heterocycloalkyl, substituted heterocycloalkyl;

$R^3$, $R^4$, and $R^5$ can be the same or different and are independently selected from H, alkyl, substituted alkyl; and $R^6$ is selected from aryl, substituted aryl, heteroaryl, and substituted heteroaryl and —$NR^{11}R^{12}$.

4. A compound according to claim 3, wherein in formula I, $R^1$ is selected from alkyl and substituted alkyl;

$R^3$, $R^4$, and $R^5$ each is selected from —H, alkyl, and substituted alkyl.

5. A compound according to claim 4, wherein in formula I, $R^3$, $R^4$, and $R^5$ each is selected from —H.

6. A compound selected from the group consisting of:

7-(2,4-Dichlorophenyl)-N,N-diethylpyrazolo[1,5-a]pyridin-3-amine;

7-(2,4-Dichlorophenyl)-N,N-dipropylpyrazolo[1,5-a]pyridin-3-amine;

N-(Cyclopropylmethyl)-N-ethyl-7-(2,4-dichlorophenyl)pyrazolo[1,5-a]pyridin-3-amine;

7-(2,4-Dichlorophenyl)-N,N-diethyl-2-methylpyrazolo[1,5-a]pyridin-3-amine;

7-(2,4-Dichlorophenyl)-2-methyl-N,N-dipropylpyrazolo[1,5-a]pyridin-3-amine;

7-(2,4-Dichlorophenyl)-N,N,2-triethylpyrazolo[1,5-a]pyridin-3-amine;

7-(2-Methyl-4-chlorophenyl)-N,N,2-triethylpyrazolo[1,5-a]pyridin-3-amine;

7-(2-Chloro-4-trifluoromethylphenyl)-N,N,2-triethylpyrazolo[1,5-a]pyridin-3-amine;

7-(2,4,6-Trimethylphenyl)-N,N,2-triethylpyrazolo[1,5-a]pyridin-3-amine;

7-(2,4-Dichlorophenyl)-2-ethyl-N,N-dipropylpyrazolo[1,5-a]pyridin-3-amine;
2-Ethyl-7-(4-methoxy-2-methylphenyl)-N,N-dipropylpyrazolo[1,5-a]pyridin-3-amine;
7-(2-Chloro-4-methoxyphenyl)-2-ethyl-N,N-dipropylpyrazolo[1,5-a]pyridin-3-amine;
7-[4-(Dimethylamino)-2-(trifluoromethyl)phenyl]-2-ethyl-N,N-dipropylpyrazolo[1,5-a]pyridin-3-amine;
2-Ethyl-7-(2-methoxy-4,6-dimethylphenyl)-N,N-dipropylpyrazolo[1,5-a]pyridin-3-amine;
7-[2-Chloro-4-(dimethylamino)phenyl]-2-ethyl-N,N-dipropylpyrazolo[1,5-a]pyridin-3-amine;
7-(2,4-Dimethoxyphenyl)-2-ethyl-N,N-dipropylpyrazolo[1,5-a]pyridin-3-amine;
7-[6-(Dimethylamino)-4-methylpyridin-3-yl]-2-ethyl-N,N-dipropylpyrazolo[1,5-a]pyridin-3-amine;
7-(2-Chloro-4-methoxyphenyl)-2-ethyl-N-(3-fluoropropyl)-N-(2-methoxyethyl)pyrazolo[1,5-a]pyridin-3-amine;
7-(2,4-Dimethoxyphenyl)-2-ethyl-N-(3-fluoropropyl)-N-(2-methoxyethyl)pyrazolo[1,5-a]pyridin-3-amine;
7-(2-Chloro-4-methoxyphenyl)-N,2-diethyl-N-(3-fluoropropyl)pyrazolo[1,5-a]pyridin-3-amine;
7-(2,4-Dimethoxyphenyl)-N,2-diethyl-N-(3-fluoropropyl)pyrazolo[1,5-a]pyridin-3-amine;
7-(2-Chloro-4-methoxyphenyl)-2-ethyl-N-(3-fluoropropyl)-N-methylpyrazolo[1,5-a]pyridin-3-amine;
7-(2,4-Dimethoxyphenyl)-N,2-diethyl-N-(2-fluoroethyl)pyrazolo[1,5-a]pyridin-3-amine;
7-(2-Chloro-4-methoxyphenyl)-2-ethyl-N-(2-fluoroethyl)-N-(2-methoxyethyl)pyrazolo[1,5-a]pyridin-3-amine;
7-(2,4-Dimethoxyphenyl)-2-ethyl-N-(2-fluoroethyl)-N-(2-methoxyethyl)pyrazolo[1,5-a]pyridin-3-amine;
N-(Cyclopropylmethyl)-7-(2,4-dichlorophenyl)-N,2-diethylpyrazolo[1,5-a]pyridin-3-amine;
7-(2-Chloro-4-methoxyphenyl)-N-(cyclopropylmethyl)-N,2-diethylpyrazolo[1,5-a]pyridin-3-amine;
N-(Cyclopropylmethyl)-7-(2,4-dichlorophenyl)-2-ethyl-N-propylpyrazolo[1,5-a]pyridin-3-amine;
7-(2-Chloro-4-methoxyphenyl)-N-(cyclopropylmethyl)-2-ethyl-N-propylpyrazolo[1,5-a]pyridin-3-amine;
7-(2,4-Dichlorophenyl)-N-(1-ethylpropyl)-2-methylpyrazolo[1,5-a]pyridin-3-amine;
7-(2,4-Dichlorophenyl)-N-[2-methoxy-1-(methoxymethyl)ethyl]-2-methylpyrazolo[1,5-a]pyridin-3-amine;
7-(2,4-Dichlorophenyl)-2-ethyl-N-(1-ethylpropyl)pyrazolo[1,5-a]pyridin-3-amine;
7-(2,4-Dichlorophenyl)-2-ethyl-N-[2-methoxy-1-(methoxymethyl)ethyl]pyrazolo[1,5-a]pyridin-3-amine;
N-(sec-Butyl)-7-(2-chloro-4-methoxyphenyl)-2,6-dimethylpyrazolo[1,5-a]pyridin-3-amine;
7-(2,4-Dichlorophenyl)-N-(1-ethylpropyl)-2,6-dimethylpyrazolo[1,5-a]pyridin-3-amine;
7-{[4-(Benzyloxy)pyridin-2-yl]oxy}-N,N-diethylpyrazolo[1,5-a]pyridin-3-amine;
N,N-Diethyl-2-methyl-7-[(4-methylpyridin-2-yl)oxy]pyrazolo[1,5-a]pyridin-3-amine;
3-sec-Butyl-7-(2,4-dichlorophenyl)-2-ethylpyrazolo[1,5-a]pyridine;
7-(2-Chloro-4-methoxyphenyl)-3-isopropyl-2-methylpyrazolo[1,5-a]pyridine;
1-[7-(2,4-Dichlorophenyl)-2-methylpyrazolo[1,5-a]pyridin-3-yl]-1,2,3,6-tetrahydropyridine-4-carboxamide;
1-[7-(2-Chloro-4-methoxyphenyl)-2-methylpyrazolo[1,5-a]pyridin-3-yl]-1,2,3,6-tetrahydropyridine-4-carboxamide;
1-[7-(6-Methoxy-2-methylpyridin-3-yl)-2-methylpyrazolo[1,5-a]pyridin-3-yl]-1,2,3,6-tetrahydropyridine-4-carboxamide;
1-[7-(2,4-Dichlorophenyl)-2-ethylpyrazolo[1,5-a]pyridin-3-yl]-1,2,3,6-tetrahydropyridine-4-carboxamide;
1-[7-(2-Chloro-4-methoxyphenyl)-2-ethylpyrazolo[1,5-a]pyridin-3-yl]-1,2,3,6-tetrahydropyridine-4-carboxamide;
1-[7-(6-Methoxy-2-methylpyridin-3-yl)-2-ethylpyrazolo[1,5-a]pyridin-3-yl]-1,2,3,6-tetrahydropyridine-4-carboxamide; and
a pharmaceutically acceptable salt of any of said compounds.

7. A compound according to claims 6, which is selected from the group consisting of
3-sec-Butyl-7-(2,4-dichlorophenyl)-2-ethylpyrazolo[1,5-a]pyridine;
7-(2-Chloro-4-methoxyphenyl)-3-isopropyl-2-methylpyrazolo[1,5-a]pyridine;
1-[7-(2,4-Dichlorophenyl)-2-methylpyrazolo[1,5-a]pyridin-3-yl]-1,2,3,6-tetrahydropyridine-4-carboxamide;
1-[7-(2-Chloro-4-methoxyphenyl)-2-methylpyrazolo[1,5-a]pyridin-3-yl]-1,2,3,6-tetrahydropyridine-4-carboxamide;
1-[7-(6-Methoxy-2-methylpyridin-3-yl)-2-methylpyrazolo[1,5-a]pyridin-3-yl]-1,2,3,6-tetrahydropyridine-4-carboxamide;
1-[7-(2,4-Dichlorophenyl)-2-ethylpyrazolo[1,5-a]pyridin-3-yl]-1,2,3,6-tetrahydropyridine-4-carboxamide;
1-[7-(2-Chloro-4-methoxyphenyl)-2-ethylpyrazolo[1,5-a]pyridin-3-yl]-1,2,3,6-tetrahydropyridine-4-carboxamide;
1-[7-(6-Methoxy-2-methylpyridin-3-yl)-2-ethylpyrazolo[1,5-a]pyridin-3-yl]-1,2,3,6-tetrahydropyridine-4-carboxamide; and
a pharmaceutically acceptable salt of any of said compounds.

8. A pharmaceutical composition comprising a compound of claim 1 and optionally a pharmaceutically acceptable carrier.

9. An article of manufacture comprising: a) a packaging material; b) a pharmaceutical agent comprising a compound of claim 1, which pharmaceutical agent is contained within the packaging material, and c) a label or package insert contained within said packaging material indicating that said pharmaceutical agent is for treating, anxiety, or depression.

10. A method of treating a disorder in a human, comprising administering to the human in need thereof an effective amount of a compound of claim 1, wherein the disorder is selected from anxiety; and depression.

* * * * *